(12) United States Patent
Birikh

(10) Patent No.: US 9,896,667 B2
(45) Date of Patent: Feb. 20, 2018

(54) LACCASE VARIANTS WITH IMPROVED PROPERTIES

(71) Applicant: METGEN OY, Kaarina (FI)

(72) Inventor: Klara Birikh, Kaarina (FI)

(73) Assignee: METGEN OY, Kaarina (FI)

( * ) Notice: Subject to any disclaimer, the term of this patent is extended or adjusted under 35 U.S.C. 154(b) by 0 days.

(21) Appl. No.: 15/303,486

(22) PCT Filed: Apr. 11, 2015

(86) PCT No.: PCT/EP2015/057917
§ 371 (c)(1),
(2) Date: Oct. 11, 2016

(87) PCT Pub. No.: WO2015/155363
PCT Pub. Date: Oct. 15, 2015

(65) Prior Publication Data
US 2017/0037384 A1 Feb. 9, 2017

(30) Foreign Application Priority Data

Apr. 11, 2014 (EP) ..................................... 14164498

(51) Int. Cl.
*C12N 9/14* (2006.01)
*C12N 9/02* (2006.01)

(52) U.S. Cl.
CPC .... *C12N 9/0061* (2013.01); *C12Y 110/03002* (2013.01)

(58) Field of Classification Search
CPC .................................................. C12N 9/0061
USPC ....................................................... 435/195
See application file for complete search history.

(56) References Cited

FOREIGN PATENT DOCUMENTS

| WO | 2013038062 A1 | 3/2013 |
|---|---|---|
| WO | 2015144679 A1 | 10/2015 |
| WO | 2015155363 A1 | 10/2015 |
| WO | 2015158803 A1 | 10/2015 |

OTHER PUBLICATIONS

Kumar et al., Combined sequence and structure analysis of the fungal laccase family, Biotechnology and Bioengineering, Aug. 20, 2003, pp. 386-394, vol. 83, No. 4.
Koschorreck et al., Improving the functional expression of a Bacillus licheniformis laccase by random and site-directed mutagenesis, BMC Biotechnology, Feb. 23, 2009, p. 12, vol. 9, No. 1, Biomed Central Ltd., London, GB.
PCT International Search Report, PCT/EP2015/057917 dated Aug. 5, 2015.
PCT International Written Opinion, PCT/EP2015/057917 dated Aug. 5, 2015.
XP-002728227, Bacillus pumilus ATCC 7061 spore coat protein A, online database.
XP-002728228, Bacillus pumilus L-9 laccase, SEQ ID 2, online database, (visited Jun. 8, 2014), available at http://ibis/exam/dbfetch.jsp?id=GSP:BBB37319.

*Primary Examiner* — Tekchand Saidha
(74) *Attorney, Agent, or Firm* — TraskBritt, P.C.

(57) ABSTRACT

This application relates to laccase variants and uses thereof as eco-friendly biocatalysts in various industrial processes. More in particular, the disclosure relates to a polypeptide with laccase activity comprising an amino acid sequence that is at least 75% identical to the amino acid sequence according to SEQ ID NO: 1, wherein the polypeptide comprises an amino acid residue selected from the group consisting of threonine, proline, alanine, glycine, serine, cysteine, aspartic acid, asparagine and valine at a position corresponding to amino acid 149 of SEQ ID NO: 1.

21 Claims, 2 Drawing Sheets

LACCASE VARIANTS WITH IMPROVED PROPERTIES

CROSS-REFERENCE TO RELATED APPLICATIONS

This application is a national phase entry under 35 U.S.C. § 371 of International Patent Application PCT/EP2015/057917, filed Apr. 11, 2015, designating the United States of America and published in English as International Patent Publication WO 2015/155363 A1 on Oct. 15, 2015, which claims the benefit under Article 8 of the Patent Cooperation Treaty to European Patent Application Serial No. 14164498.9, filed Apr. 11, 2014.

STATEMENT ACCORDING TO 37 C.F.R. § 1.821(c) or (e)—SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

TECHNICAL FIELD

This application relates to laccase variants and uses thereof as eco-friendly biocatalysts in various industrial processes.

BACKGROUND

Laccases (EC 1.10.3.2) are enzymes having a wide taxonomic distribution and belonging to the group of multicopper oxidases. Laccases are eco-friendly catalysts that use molecular oxygen from air to oxidize various phenolic and non-phenolic lignin-related compounds as well as highly recalcitrant environmental pollutants, and produce water as the only side-product. These natural "green" catalysts are used for diverse industrial applications including the detoxification of industrial effluents, mostly from the paper and pulp, textile and petrochemical industries, and used as bioremediation agent to clean up herbicides, pesticides and certain explosives in soil. Laccases are also used as cleaning agents for certain water purification systems. In addition, their capacity to remove xenobiotic substances and produce polymeric products makes them a useful tool for bioremediation purposes. Another large proposed application area of laccases is biomass pretreatment in biofuel and in the pulp and paper industries.

Laccase molecules are usually monomers consisting of three consecutively connected cupredoxin-like domains twisted in a tight globule. The active site of laccases contains four copper ions: a mononuclear "blue" copper ion (T1 site) and a three-nuclear copper cluster (T2/T3 site) consisting of one T2 copper ion and two T3 copper ions.

Laccases may be isolated from different sources such as plants, fungi or bacteria and are very diverse in primary sequences. However, they have some conserved regions in the sequences and certain common features in their three-dimensional structures. A comparison of sequences of more than 100 laccases has revealed four short conservative regions (no longer than 10 aa each), which are specific for all laccases.[7, 8] One cysteine and ten histidine residues form a ligand environment of copper ions of the laccase active site present in these four conservative amino acid sequences.

The best studied bacterial laccase is CotA laccase. CotA is a component of the outer coat layers of bacillus endospore. It is a 65-kDa protein encoded by the CotA gene.[1]

CotA belongs to a diverse group of multi-copper "blue" oxidases that includes the laccases. This protein demonstrates high thermostability, and resistance to various hazardous elements in accordance with the survival abilities of the endospore.

Recombinant protein expression in easily cultivatable hosts can allow higher productivity in a shorter time and reduces the costs of production. The versatility and scaling-up possibilities of the recombinant protein production opened up new commercial opportunities for their industrial uses. Moreover, protein production from pathogenic or toxin-producing species can take advantage of safer or even GRAS (generally recognized as safe) microbial hosts. In addition, protein engineering can be employed to improve the stability, activity and/or specificity of an enzyme; thus, tailor made enzymes can be produced to suit the requirement of the users or of the process.

Enzyme productivity can be increased by the use of multiple gene copies, strong promoters and efficient signal sequences, properly designed to address proteins to the extracellular medium, thus simplifying downstream processing.

Recombinant protein yield in bacterial hosts is often limited by the inability of the protein to fold into correct 3D-structure upon biosynthesis of the polypeptide chain. This may cause exposure of hydrophobic patches on the surface of the protein globule and result in protein aggregation. Mechanisms of heterologous protein folding in vivo are poorly understood, and foldability of different proteins in bacteria is unpredictable.

Yield of soluble active protein can sometimes be improved by changing cultivation conditions. In addition, there are examples when protein yield was improved by introducing single-point mutations in the protein sequence. However, no rationale has been identified behind finding suitable mutations.

Heterologous expression of laccase in *Escherichia coli* has often been used as a strategy to get around the problem of obtaining laccases that are not easily producible in natural hosts. The recombinant expression of *Bacillus subtilis* CotA in *E. coli* has allowed its deep characterization, structure solving, and functional evolution.[1, 2, 3] However, very often, the production yield is low, due to a strong tendency of this enzyme to form aggregates that renders the protein irreversibly inactive.[4] This tendency has been attributed to the fact that, in nature, CotA laccase is integrated in a spore coat structure via interaction with other protein components, and it is likely that correct laccase folding is enhanced by interaction with other proteins. When this laccase is recombinantly expressed as an individual polypeptide, those supporting interactions are missing and many miss-folded proteins form aggregates in bacterial cells. When expressed in higher microorganisms such as yeast, misfolded laccase molecules are, for a large part, degraded.

There is a need in the art for means and methods for improving the yield of laccases in heterologous expression systems. This is particularly true for bacterial laccases, such as CotA laccases.

BRIEF SUMMARY

This disclosure addresses this need in that it provides variant laccases with improved properties. More in particular, the disclosure relates to a polypeptide with laccase activity comprising an amino acid sequence that is at least 75% identical to the amino acid sequence according to SEQ ID NO: 1, wherein the polypeptide comprises a small amino acid residue selected from the group consisting of threonine, proline, alanine, glycine, serine, cysteine, aspartic acid, asparagine and valine at an amino acid position corresponding to position 149 in SEQ ID NO: 1.

A threonine residue at a position corresponding to amino acid 149 of SEQ ID NO: 1 is preferred.

In addition, the disclosure provides improved nucleic acids, vectors and compositions encoding the variant laccase enzymes according to the disclosure.

The disclosure also provides recombinant heterologous expression systems such as host cells comprising a nucleic acid, a vector or a composition according to the disclosure.

Also provided herein are methods for producing a polypeptide according to the disclosure, comprising the steps of:
  a. culturing a recombinant host cell comprising a polynucleotide according to the disclosure under conditions suitable for the production of the polypeptide, and
  b. recovering the polypeptide obtained, and
  c. optionally purifying the polypeptide.

The disclosure also relates to the use of a polypeptide according to the disclosure in an application selected from the group consisting of pulp delignification, degrading or decreasing the structural integrity of lignocellulosic material, textile dye bleaching, wastewater detoxification, xenobiotic detoxification, production of a sugar from a lignocellulosic material and recovering cellulose from a biomass.

The disclosure also relates to a method for improving the yield of a polypeptide with laccase activity in a heterologous expression system comprising the step of altering the amino acid of that polypeptide at a position corresponding to position 149 in SEQ ID NO: 1 to a small amino acid residue.

Preferred embodiments of these aspects will be described in more detail below. For the purpose of clarity and a concise description, features are described herein as part of the same or separate embodiments; however, it will be appreciated that the scope of the disclosure may include embodiments having combinations of all or some of the features described.

DETAILED DESCRIPTION

Figure 1:
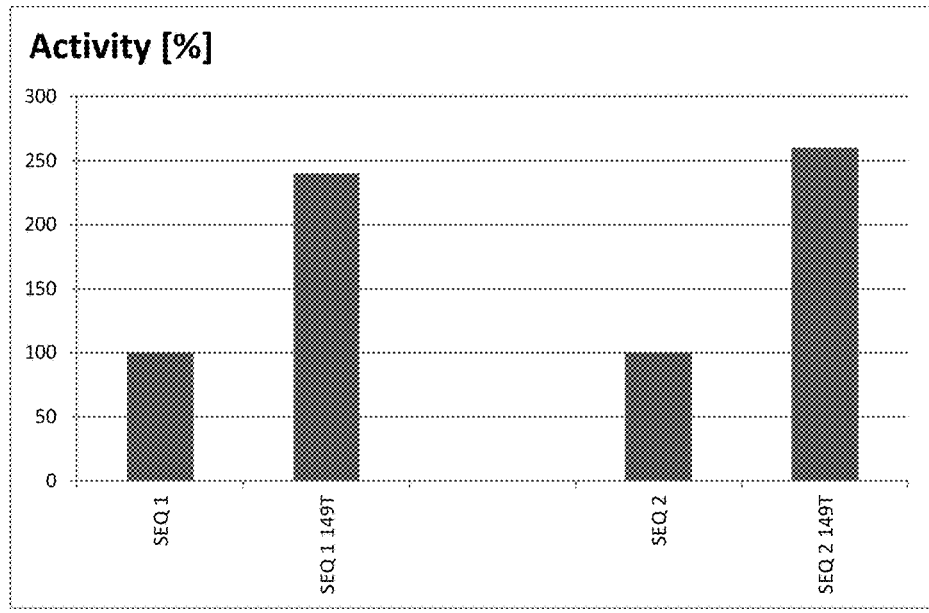
FIG. 1: Relative increase of volumetric activity. Graph showing the relative increase of volumetric activity in parallel cultures in *E. coli* of wild-type (non-mutated) versus variant laccases according to SEQ ID NO: 1 and SEQ ID NO: 2. The abbreviation "SEQ" followed by a number refers to the SEQ ID NO: of the respective number; SEQ1 refers to SEQ ID NO: 1. SEQ1 149T refers to the polypeptide according to SEQ ID NO: 1, wherein the amino acid corresponding to position 149 is replaced by a T (Thr or threonine).

This disclosure is based on the observation that a single amino acid substitution in different laccases improves the yield of that laccase by at least 50% when expressed in prokaryotes as well as in eukaryotes. It was also found that the variant laccase remains active.

The term "amino acid substitution" is used herein the same way as it is commonly used, i.e., the term refers to a replacement of one or more amino acids in a protein with another amino acid. Artificial amino acid substitutions may also be referred to as mutations.

The term "small amino acid" as used herein is intended to cover a group of amino acids that are usually considered as small or tiny amino acids. In a preferred embodiment, this group is limited to amino acids threonine, proline, alanine, glycine, serine, cysteine, aspartic acid, asparagine and valine.

SEQ ID NO: 1 is a CotA laccase from *Bacillus subtilis* newly disclosed herein, whereas SEQ ID NO: 2 is a CotA laccase that has been previously disclosed in WO 2013/038062. It was found that laccase variants that have a small amino acid residue selected from the group consisting of threonine, proline, alanine, glycine, serine, cysteine, aspartic acid, asparagine and valine at an amino acid position corresponding to position 149 in SEQ ID NO: 1 provided a higher yield when expressed in a heterologous expression system.

Laccase variants with an amino acid residue selected from the group consisting of threonine, proline, asparagine and aspartic acid at an amino acid position corresponding to position 149 in SEQ ID NO: 1 are preferred in the context of this disclosure.

Variants carrying a threonine residue at an amino acid position corresponding to position 149 in SEQ ID NO: 1 are most preferred since they resulted in the highest yield of recombinantly expressed laccase.

SEQ ID NO: 3 and SEQ ID NO: 4 disclose *B. subtilis* spore coat proteins with laccase activity (CotA laccase), that carry a 149T mutation. In fact, SEQ ID NO: 3 is a variant from SEQ ID NO: 1 wherein an isoleucine residue at position 149 has been replaced by a threonine residue. SEQ ID NO: 4 is a variant from SEQ ID NO: 2 wherein an isoleucine residue at position 149 has been replaced by a threonine residue.

A homology search for proteins homologous to SEQ ID NO: 1 was performed using SEQ ID NO: 1 as the query sequence in the "Standard protein BLAST" software, available on the World Wide Web at blast.ncbi.nlm.nih.gov/Blast.cgi?PROGRAM=blastp&PAGE_TYPE=Blast Search&LINK_LOC=blasthome. More information on the software and database versions is available at the National Center for Biotechnology Information at National library of Medicine at the National institute of Health internet site ncbi.nlm.nih.gov. Therein, a number of molecular biology tools including BLAST (Basic Logical Alignment Search Tool) is to be found. BLAST makes use of the following databases: all non-redundant GenBank CDS translations+PDB+SwissProt+PIR+PRF excluding environmental samples from WGS projects. The search as reported herein was performed online on 19 Feb. 2014 and employed BLASTP version 2.2.29+.

The search revealed 44 sequences with at least 75% sequence identity to SEQ ID NO: 1 (Table 1). These sequences are herein provided as SEQ ID NOS: 51 to 94.

TABLE 1

Sequences obtained from a BLAST search disclosing 44 sequences with at least 75% identity to SEQ ID NO: 1

| SEQ ID NO: | BLAST No: | Description | Accession No: | Overall identity[1] | AA # corr. to pos 149[2] | AA at pos corr. to AA[3] |
|---|---|---|---|---|---|---|
| 1 | 1 | CotA laccase from *B. subtilis* (query sequence) | | 100% | 149 | Ile |
| 51 | 2 | laccase [*Bacillus subtilis*] | AGZ16504.1 | 98% | 149 | Ile |
| 52 | 3 | spore copper-dependent laccase (outer coat) [*Bacillus subtilis* subsp. *spizizenii* str. W23] >ref|WP_003219376.1|copper oxidase [*Bacillus subtilis*] >gb|EFG93543.1|spore copper-dependent laccase [*Bacillus subtilis* subsp. *spizizenii* ATCC 6633] >gb|ADM36695.1|spore copper-dependent laccase (outer coat) [*Bacillus subtilis* subsp. *spizizenii* str. W23] | YP_003865004.1 | 98% | 149 | Ile |
| 53 | 4 | spore copper-dependent laccase [*Bacillus subtilis*] >gb|ELS60660.1|spore copper-dependent laccase [*Bacillus subtilis* subsp. *inaquosorum* KCTC 13429] | WP_004397739.1 | 96% | 149 | Ile |
| 54 | 5 | copper oxidase [*Bacillus subtilis*] | WP_019713492.1 | 96% | 149 | Ile |
| 55 | 6 | laccase [*Bacillus vallismortis*] | AGR50961.1 | 95% | 149 | Ile |
| 56 | 7 | spore coat protein A [*Bacillus subtilis* XF-1] >ref|WP_015382982.1|spore coat protein A [*Bacillus*] >gb|AGE62493.1|spore coat protein A [*Bacillus subtilis* XF-1] >gb|ERI42893.1|copper oxidase [*Bacillus sp.* EGD-AK10] | YP_007425830.1 | 96% | 151 | Ile |
| 57 | 8 | spore copper-dependent laccase [*Bacillus subtilis* BSn5] >ref|YP_005559844.1|spore coat protein A [*Bacillus subtilis* subsp. *natto* BEST195] >ref|YP_007210655.1|Spore coat protein A [*Bacillus subtilis* subsp. *subtilis* str. BSP1] >ref|WP_014479048.1|copper oxidase [*Bacillus subtilis*] >dbj|BAI84141.1|spore coat protein A [*Bacillus subtilis* subsp. *natto* BEST195] >gb|ADV95614.1|spore copper-dependent laccase [*Bacillus subtilis* BSn5] >gb|ADZ57279.1|laccase [*Bacillus sp.* LS02] >gb|ADZ57280.1|laccase [*Bacillus sp.* LS03] >gb|ADZ57283.1|laccase [*Bacillus sp.* WN01] >gb|ADZ57284.1|laccase [*Bacillus subtilis*] >gb|AGA20638.1|Spore coat protein A [*Bacillus subtilis* subsp. *subtilis* str. BSP1] | YP_004206641.1 | 96% | 149 | Ile |
| 58 | 9 | CotA [*Bacillus sp.* JS] >ref|WP_014663045.1| copper oxidase [*Bacillus sp.* JS] >gb|AFI27241.1| CotA [*Bacillus sp.* JS] | YP_006230497.1 | 95% | 149 | Ile |
| 59 | 10 | copper oxidase [*Bacillus subtilis* QH-1] | EXF51833.1 | 95% | 149 | Ile |
| 60 | 11 | copper oxidase [*Bacillus subtilis*] >gb|EHA29133.1| spore copper-dependent laccase [*Bacillus subtilis* subsp. *subtilis* str. SC-8] | WP_003234000.1 | 95% | 151 | Ile |
| 61 | 12 | outer spore coat copper-dependent laccase [*Bacillus subtilis* QB928] >ref|WP_014906195.1|copper oxidase [*Bacillus subtilis*] >dbj|BAA22774.1|spore coat protein A [*Bacillus subtilis*] >gb|AFQ56549.1| Outer spore coat copper-dependent laccase [*Bacillus subtilis* QB928] | YP_006628799.1 | 95% | 151 | Ile |
| 62 | 13 | spore coat protein A [*Bacillus subtilis* subsp. *subtilis* str. 168] | NP_388511.1 | 95% | 149 | Ile |
| 63 | 14 | spore coat protein A [*Bacillus subtilis* subsp. *subtilis* str. BAB-1] >ref|WP_015482891.1|spore coat protein A [*Bacillus subtilis*] >gb|AGI27890.1|spore coat protein A [*Bacillus subtilis* subsp. *subtilis* str. BAB-1] | YP_007661398.1 | 95% | 149 | Ile |
| 64 | 15 | Chain A, Mutations In The Neighbourhood Of Cota-Laccase Trinuclear Site: E498d Mutant | 4AKQ_A | 95% | 149 | Ile |
| 65 | 16 | Chain A, Mutations In The Neighbourhood Of Cota-Laccase Trinuclear Site: D116n Mutant | 4A68_A | 95% | 149 | Ile |
| 66 | 17 | Chain A, Mutations In The Neighbourhood Of Cota-Laccase Trinuclear Site: D116a Mutant | 4A66_A | 95% | 149 | Ile |
| 67 | 18 | spore coat protein [*Bacillus subtilis*] | ACS44284.1 | 95% | 149 | Ile |
| 68 | 19 | spore coat protein [*Bacillus subtilis*] | AGK12417.1 | 95% | 149 | Ile |

TABLE 1-continued

Sequences obtained from a BLAST search disclosing 44 sequences with at least 75% identity to SEQ ID NO: 1

| SEQ ID NO: | BLAST No: | Description | Accession No: | Overall identity[1] | AA # corr. to pos 149[2] | AA at pos corr. to AA[3] |
|---|---|---|---|---|---|---|
| 69 | 20 | Chain A, Crystal Structure Of The Reconstituted Cota | 2X87_A | 95% | 149 | Ile |
| 70 | 21 | laccase [*Bacillus* sp. ZW2531-1] | AFN66123.1 | 95% | 149 | Ile |
| 71 | 22 | Chain A, Mutations In The Neighbourhood Of Cota-Laccase Trinuclear Site: D116e Mutant | 4A67_A | 95% | 149 | Ile |
| 72 | 23 | Chain A, Proximal Mutations At The Type 1 Cu Site Of Cota-Laccase: I494a Mutant | 2WSD_A | 95% | 149 | Ile |
| 73 | 24 | Chain A, Mutations In The Neighbourhood Of Cota-Laccase Trinuclear Site: e498t Mutant | 4AKP_A | 95% | 149 | Ile |
| 74 | 25 | laccase [*Bacillus* sp. HR03] | ACM46021.1 | 94% | 149 | Ile |
| 75 = 15 | 26 | copper oxidase [*Bacillus vallismortis*] | WP_010329056.1 | 94% | 149 | Ile |
| 76 | 27 | laccase [*Bacillus subtilis*] | AEK80414.1 | 92% | 149 | Ile |
| 77 | 28 | copper oxidase [*Bacillus mojavensis*] | WP_010333230.1 | 91% | 149 | Ile |
| 78 | 29 | Chain A, Mutations In The Neighbourhood Of Cota-Laccase Trinuclear Site: E498l Mutant | 4AKO_A | 94% | 145 | Ile |
| 79 | 30 | CotA [*Bacillus subtilis*] | AAB62305.1 | 89% | 149 | Ile |
| 80 | 31 | spore copper-dependent laccase [*Bacillus atrophaeus* 1942] >ref|WP_003328493.1|copper oxidase [*Bacillus atrophaeus*] >gb|ADP31092.1| spore copper-dependent laccase (outer coat) [*Bacillus atrophaeus* 1942] >gb|EIM09308.1|spore copper-dependent laccase [*Bacillus atrophaeus* C89] | YP_003972023.1 | 81% | 149 | Ile |
| 81 | 32 | Spore coat protein A [*Bacillus atrophaeus*] >gb|EOB38473.1|Spore coat protein A [*Bacillus atrophaeus* UCMB-5137] | WP_010787813.1 | 81% | 149 | Ile |
| 82 | 33 | copper oxidase [*Bacillus* sp. 5B6] >gb|EIF12180.1| CotA [*Bacillus* sp. 5B6] | WP_007609818.1 | 77% | 149 | Leu |
| 83 | 34 | outer spore coat copper-dependent laccase [*Bacillus amyloliquefaciens* subsp. *plantarum* UCMB5036] >ref|YP_008411651.1|outer spore coat copper-dependent laccase [*Bacillus amyloliquefaciens* subsp. *plantarum* UCMB5033] >ref|YP_008420054.1|outer spore coat copper-dependent laccase [*Bacillus amyloliquefaciens* subsp. *plantarum* UCMB5113] >ref|WP_015416957.1|outer spore coat copper-dependent laccase [*Bacillus amyloliquefaciens*] >emb|CCP20645.1|outer spore coat copper-dependent laccase [*Bacillus amyloliquefaciens* subsp. *plantarum* UCMB5036] >emb|CDG28620.1| outer spore coat copper-dependent laccase [*Bacillus amyloliquefaciens* subsp. *plantarum* UCMB5033] >emb|CDG24919.1|outer spore coat copper-dependent laccase [*Bacillus amyloliquefaciens* subsp. *plantarum* UCMB5113] | YP_007496315.1 | 77% | 149 | Leu |
| 84 | 35 | spore coat protein CotA [*Bacillus amyloliquefaciens* subsp. *plantarum* YAU B9601-Y2] >ref|YP_006327430.1|spore coat protein A [*Bacillus amyloliquefaciens* Y2] >ref|WP_014417082.1|copper oxidase [*Bacillus amyloliquefaciens*] >gb|ADZ57285.1 |laccase [*Bacillus* sp. LC02] >emb|CCG48602.1|spore coat protein CotA [*Bacillus amyloliquefaciens* subsp. *plantarum* YAU B9601-Y2] >gb|AFJ60705.1|spore coat protein A [*Bacillus amyloliquefaciens* Y2] >dbj|BAM49543.1|spore copper-dependent laccase [*Bacillus subtilis* BEST7613] >dbj|BAM56813.1| spore copper-dependent laccase [*Bacillus subtilis* BEST7003] | YP_005419918.1 | 77% | 149 | Leu |
| 85 | 36 | bilirubin oxidase [*Bacillus amyloliquefaciens* subsp. *plantarum* NAU-B3] >ref|WP_022552695.1| bilirubin oxidase [*Bacillus amyloliquefaciens*] >emb|CDH94370.1| bilirubin oxidase [*Bacillus amyloliquefaciens* subsp. *plantarum* NAU-B3] | YP_008625231.1 | 77% | 149 | Leu |
| 86 | 37 | spore coat protein A [*Bacillus amyloliquefaciens* subsp. *plantarum* AS43.3] >ref|WP_015239305.1| spore coat protein A [*Bacillus amyloliquefaciens*] >gb|AFZ89646.1| spore coat protein A [*Bacillus amyloliquefaciens* subsp. *plantarum* AS43.3] | YP_007185316.1 | 77% | 149 | Leu |
| 87 = 5 | 38 | CotA [*Bacillus amyloliquefaciens* subsp. *plantarum* str. FZB42] >ref|YP_008725930.1| cotA [*Bacillus amyloliquefaciens* CC178] >ref|WP_012116986.1| copper oxidase [*Bacillus amyloliquefaciens*] | YP_001420286.1 | 77% | 149 | Leu |

TABLE 1-continued

Sequences obtained from a BLAST search disclosing 44 sequences with at least 75% identity to SEQ ID NO: 1

| SEQ ID NO: | BLAST No: | Description | Accession No: | Overall identity[1] | AA # corr. to pos 149[2] | AA at pos corr. to AA[3] |
|---|---|---|---|---|---|---|
| | | >gb\|ABS73055.1\| CotA [*Bacillus amyloliquefaciens* subsp. *plantarum* str. FZB42] >gb\|AGZ55352.1\| CotA [*Bacillus amyloliquefaciens* CC178] | | | | |
| 88 | 39 | laccase [*Bacillus* sp. LC03] | ADZ57286.1 | 76% | 149 | Leu |
| 89 | 40 | copper oxidase [*Bacillus* sp. 916] >gb\|EJD67619.1\| CotA [*Bacillus* sp. 916] | WP_007408880.1 | 77% | 149 | Leu |
| 90 | 41 | copper oxidase [*Bacillus amyloliquefaciens*] >gb\|ERH51073.1\| copper oxidase [*Bacillus amyloliquefaciens* EGD-AQ14] | WP_021495201.1 | 76% | 149 | Leu |
| 91 | 42 | bilirubin oxidase [*Bacillus amyloliquefaciens* subsp. *plantarum* CAU B946] >ref\|YP_007446652.1\| bilirubin oxidase [*Bacillus amyloliquefaciens* IT-45] >ref\|YP_008949033.1\| copper oxidase [*Bacillus amyloliquefaciens* LFB112] >ref\|WP_003155789.1\| copper oxidase [*Bacillus amyloliquefaciens*] >gb\|ADZ57278.1\| laccase [*Bacillus* sp. LS01] >gb\|ADZ57282.1\| laccase [*Bacillus* sp. LS05] >emb\|CCF04175.1\| bilirubin oxidase [*Bacillus amyloliquefaciens* subsp. *plantarum* CAU B946] >gb\|EKE46469.1\| bilirubin oxidase [*Bacillus amyloliquefaciens* subsp. *plantarum* M27] >gb\|AGF28771.1\| bilirubin oxidase [*Bacillus amyloliquefaciens* IT-45] >gb\|ERK81509.1\| copper oxidase [*Bacillus amyloliquefaciens* UASWS BA1] >gb\|AHC41184.1\| copper oxidase [*Bacillus amyloliquefaciens* LFB112] | YP_005129370.1 | 76% | 149 | Leu |
| 92 | 43 | copper oxidase [*Bacillus amyloliquefaciens* subsp. *plantarum* TrigoCor1448] | AHK48246.1 | 76% | 149 | Leu |
| 93 | 44 | spore copper-dependent laccase [*Bacillus amyloliquefaciens* DSM 7] >ref\|YP_005540261.1\| spore copper-dependent laccase [*Bacillus amyloliquefaciens* TA208] >ref\|YP_005544441.1\| spore copper-dependent laccase [*Bacillus amyloliquefaciens* LL3] >ref\|YP_005548603.1\| spore copper-dependent laccase [*Bacillus amyloliquefaciens* XH7] >ref\|WP_013351262.1\| copper oxidase [*Bacillus amyloliquefaciens*] >emb\|CBI41748.1\| spore copper-dependent laccase [*Bacillus amyloliquefaciens* DSM 7] >gb\|AEB22768.1\| spore copper-dependent laccase [*Bacillus amyloliquefaciens* TA208] >gb\|AEB62213.1\| spore copper-dependent laccase [*Bacillus amyloliquefaciens* LL3] >gb\|AEK87755.1\| spore copper-dependent laccase [*Bacillus amyloliquefaciens* XH7] | YP_003919218.1 | 76% | 149 | Leu |
| 94 | 45 | copper oxidase [*Bacillus siamensis*] | WP_016937040.1 | 75% | 149 | Leu |

[1]Overall identity of selected sequence with SEQ ID NO: 1, the query sequence.
[2]Position number of the selected sequence that corresponds with position 149 in SEQ ID NO: 1.
[3]Amino acid at a position of the selected sequence that corresponds with position 149 in SEQ ID NO: 1.

Analysis of the homologous proteins revealed that all proteins with at least 75% sequence identity to SEQ ID NO: 1, belong to the species of *Bacillus*. All sequences with at least 75% sequence identity to SEQ ID NO: 1 were copper-dependent oxidases (laccases) and most of them were annotated as spore coat proteins. Thus, it was concluded that sequences with this extent (at least 75%) of identity to SEQ ID NO: 1 represent a functionally and structurally highly related group of proteins that are likely to have similar structural traits and folding pathways.

Several amino acid substitutions were performed in a variety of laccases at a position corresponding to position 149 in SEQ ID NO: 1, finding that the yield of soluble recombinant laccase protein could be improved when the original amino acid (Ile or Leu) occurring at that position was replaced with a small or tiny amino acid residue selected from the group consisting of threonine, proline, alanine, glycine, serine, cysteine, aspartic acid, asparagine and valine.

In other words, the disclosure relates to a spore coat polypeptide with laccase activity wherein the polypeptide comprises an amino acid residue selected from the group consisting of threonine, proline, alanine, glycine, serine, cysteine, aspartic acid, asparagine and valine, at an amino acid position corresponding to position 149 in SEQ ID NO: 1.

Although marginal differences in yield were observed between the variants carrying the different amino acids, variants carrying a threonine residue at position 149 showed the highest yield. In a preferred embodiment, the disclosure, therefore, relates to a laccase with a threonine residue at a position corresponding to amino acid 149 of SEQ ID NO: 1.

In a further preferred embodiment, the polypeptide according to the disclosure is a polypeptide mutated as described above wherein the wild-type sequence is encoded by the genome of a *Bacillus* species, such as *Bacillus subtilis*.

None of the 45 laccases from Table 1 (44 sequences from the search plus SEQ ID NO: 1 used as the query sequence) has an amino acid selected from the group consisting of threonine, proline, alanine, glycine, serine, cysteine, aspartic acid, asparagine and valine at a position corresponding to position 149 of SEQ ID NO: 1. Thus, it may be concluded that a laccase with at least 75% sequence identity to SEQ ID NO: 1 comprising an amino acid selected from the group consisting of threonine, proline, alanine, glycine, serine, cysteine, aspartic acid, asparagine and valine at a position corresponding to position 149 of SEQ ID NO: 1 has not yet been described in the prior art.

It is remarkable that the amino acid corresponding to position 149 in SEQ ID NO: 1 is rather well conserved within the group of 44 sequences of Table 1. An isoleucine residue occurs at that position in 31 out of 44 cases (70%), whereas thirteen sequences appear to have a leucine residue at that position (30%).

It was further observed that the search identified two different groups of sequences. The first group comprises 26 sequences with between 94% and 100% identity with SEQ ID NO: 1. Those sequences were almost all annotated as Bacillus subtilis CotA spore coat proteins, apart from two Bacillus vallismortis CotA (SEQ ID NO: 55 and SEQ ID NO: 75).

A second group of 15 sequences was also identified with an identity of between 75% and 81% with the sequence of SEQ ID NO: 1.

It was found that 41 out of 44 sequences from the search (93%) belonged to either one of these two groups.

Introduction of a specific mutation in a recombinant gene is among the routine skills of a molecular biologist. Specific guidance may be obtained from *Methods in Molecular Biology*, Vol. 182, "In vitro mutagenesis protocols," eds. Jeff Braman, Humana Press 2002. There are commercially available kits for performing site-directed mutagenesis (for example, QUIKCHANGE® II XL Site-Directed Mutagenesis kit, Agilent Technologies cat. No. 200521).

Variants of representatives of laccases were prepared from each of the above-described two groups. This includes laccases with an amino acid sequence according to SEQ ID NO: 1 and SEQ ID NO: 2 as representatives of group 1 (94%400% identity). The sequences of these variants are shown as SEQ ID NO: 3 and SEQ ID NO: 4, respectively, wherein the isoleucine residue at position 149 of SEQ ID NO: 1 and SEQ ID NO: 2 was replaced by a threonine. When expressed in *E. coli*, both variants showed an increased yield of active enzyme of 240% and 260%, respectively (FIG. 1). In other words, the volumetric activity of both variants was increased to at least 240%.

As a control experiment, it was determined whether this improved volumetric activity may be attributable to an increased specific activity of the enzyme. This appeared not to be the case. The increase in the amount of mutated enzyme (149T) in the soluble fraction of cell lysate was proportional to the increase in volumetric activity, so it has to be concluded that more variant enzyme may be recovered, thereby completely accounting for the increase in volumetric activity. Hence, the yield of the laccase enzyme is increased rather than its specific activity.

A 149T variant was also prepared from a representative of laccases from the second group (75%-81% identity). The naturally occurring Leu at position 149 in SEQ ID NO: 5 (77% identity to SEQ ID NO: 1) was replaced by a threonine in order to obtain the variant according to SEQ ID NO: 6.

When expressed in *E. coli*, the 149T variant showed an increased yield of active enzyme of 250%. In other words, the 149T variant had an increased volumetric activity of at least a factor 2.5 (FIG. 2).

The naturally occurring amino acid at position 149 could also be replaced with other amino acids. Variants of representative laccases were prepared from each of the two groups identified above: SEQ ID NO: 5 and SEQ ID NO: 15. The naturally occurring Leu in SEQ ID NO: 5 and the naturally occurring Ile at position 149 of SEQ ID NO: 15 were replaced with either a threonine, proline, alanine, glycine, serine, cysteine, aspartic acid, asparagine or a valine residue. The variants of SEQ ID NO: 5 are represented by SEQ ID NOS: 6-14, respectively, whereas the variants of SEQ ID NO: 15 are represented by SEQ ID NOS: 16-24 (Tables 2 and 3).

Sequences of SEQ ID NO: 1 to SEQ ID NO: 24 are shown in Table 5.

Figure 2:
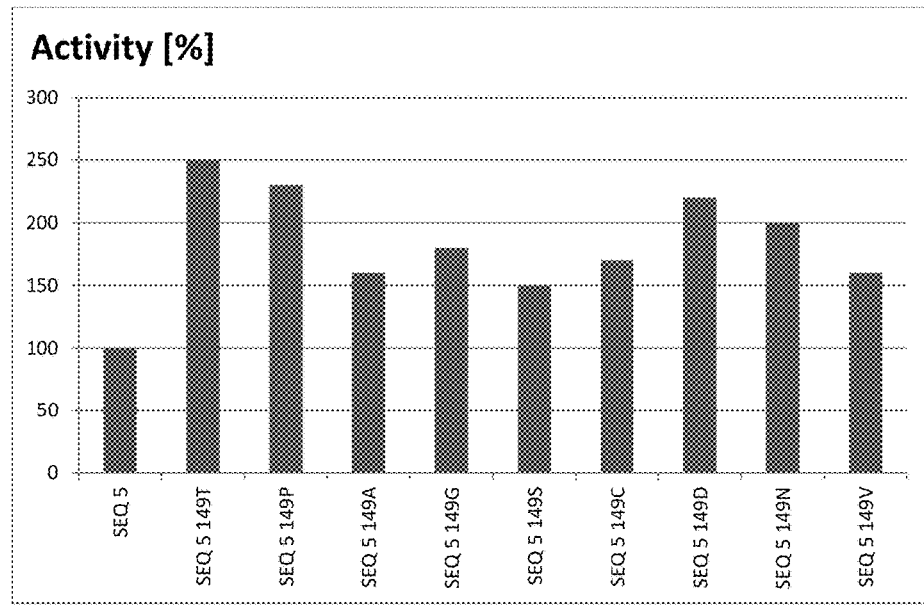
FIG. 2: Relative increase of volumetric activity. Graph showing the relative increase of volumetric activity in parallel cultures in *E. coli* of wild-type (non-mutated) versus variant laccases according to SEQ ID NO: 5. The abbreviation "SEQ" followed by a number refers to the SEQ ID NO: of the respective number; SEQ5 refers to SEQ ID NO: 5. SEQ5 149T refers to the polypeptide according to SEQ ID NO: 5, wherein the amino acid corresponding to position 149 is replaced by a T (Thr or threonine).
Figure 3:
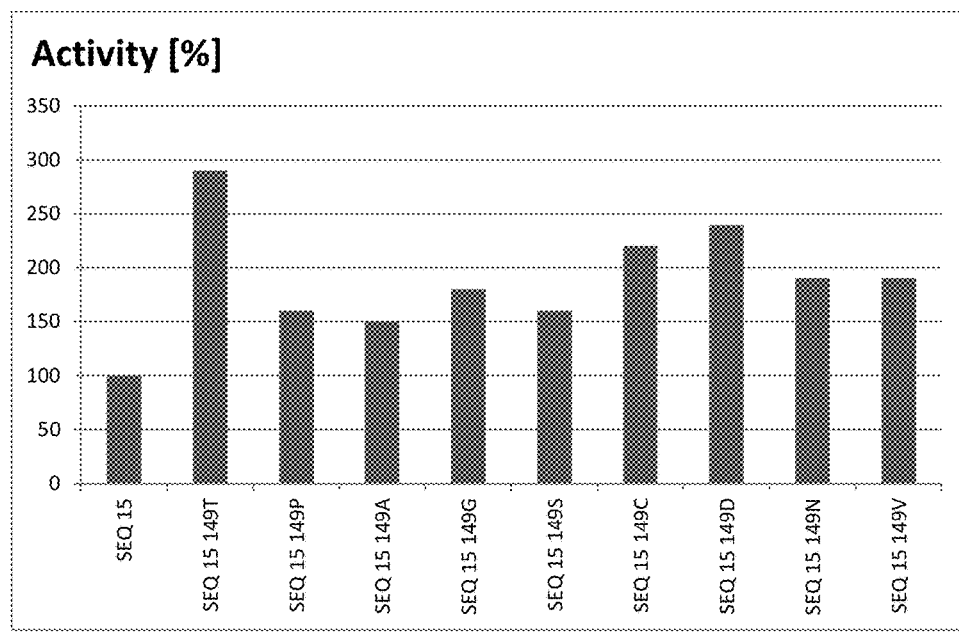
FIG. 3: Relative increase of volumetric activity. Graph showing the relative increase of volumetric activity in parallel cultures in *E. coli* of wild-type (non-mutated) versus variant laccases according to SEQ ID NO: 15. The abbreviation "SEQ" followed by a number refers to the SEQ ID NO: of the respective number; SEQ15 refers to SEQ ID NO: 15. SEQ 15 149T refers to the polypeptide according to SEQ ID NO: 15, wherein the amino acid corresponding to position 149 is replaced by a T (Thr or threonine).

Each of these variants exhibited an improved yield of at least 50% when expressed in a heterologous expression system (FIGS. 2 and 3).

Figure 4:
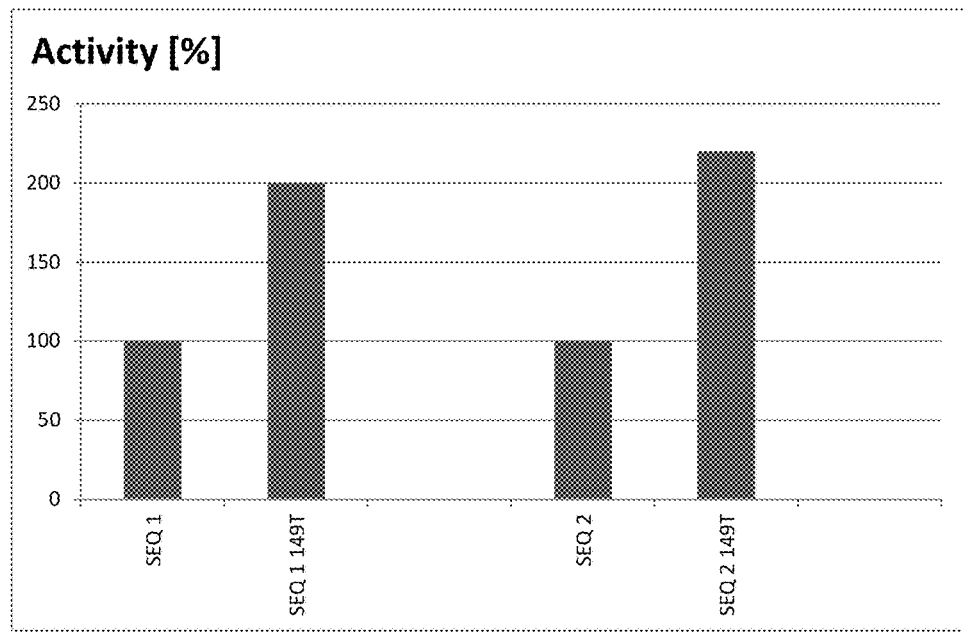
FIG. 4: Relative increase of volumetric activity. Graph showing the relative increase of volumetric activity in parallel cultures in *Pichia* pastoris of wild-type (non-mutated) versus variant laccases according to SEQ ID NO: 1 and SEQ ID NO: 2. The abbreviation "SEQ" followed by a number refers to the SEQ ID NO: of the respective number; SEQ1 refers to SEQ ID NO: 1. SEQ1 149T refers to the polypeptide according to SEQ ID NO: 1, wherein the amino acid corresponding to position 149 is replaced by a threonine residue (Thr or T).

The variants according to SEQ ID NO: 3 and SEQ ID NO: 4 were also expressed in *Pichia pastoris*. In accordance with the data obtained in a prokaryotic expression system (*E. coli*, see above) the eukaryotic expression also showed an increased yield. The yield was improved to at least 200% when the expression of the variant sequences was compared with their wild-type, SEQ ID NO: 1 and SEQ ID NO: 2, respectively (FIG. 4).

Accordingly, the disclosure relates to a polypeptide with laccase activity comprising an amino acid sequence that is at least 75% identical to the amino acid sequence according to SEQ ID NO: 1, wherein the polypeptide comprises an amino acid residue selected from the group consisting of threonine, proline, alanine, glycine, serine, cysteine, aspartic acid, asparagine and valine, at an amino acid position corresponding to position 149 in SEQ ID NO: 1.

In a preferred embodiment, the disclosure relates to a polypeptide with laccase activity consisting of an amino acid sequence that is at least 75% identical to the amino acid sequence according to SEQ ID NO: 1, wherein the polypeptide comprises a small amino acid residue selected from the group consisting of threonine, proline, alanine, glycine, serine, cysteine, aspartic acid, asparagine and valine at an amino acid position corresponding to position 149 in SEQ ID NO: 1.

In a further preferred embodiment, the disclosure relates to a polypeptide with laccase activity comprising or consisting of an amino acid sequence that is at least 75% identical to the amino acid sequence according to SEQ ID NO: 1, wherein the polypeptide comprises a threonine residue at a position corresponding to position 149 in SEQ ID NO: 1.

This variant laccase is also referred to herein as amino acid variant 149Thr or 149T. In a further preferred embodiment, the polypeptide is isolated.

The above finding that spore coat proteins occur in two distinct groups allows defining the disclosure in yet another way, such as the structural relationship between the polypeptide according to the disclosure and the reference polypeptides according to the sequences herein. Hence, the disclosure relates to a polypeptide comprising an amino acid sequence that is at least 94% identical to the amino acid sequence selected from the group consisting of SEQ ID NOS: 51-75 as representatives of group 1, as well as a polypeptide comprising an amino acid sequence that is at least 94% identical to the amino acid sequence selected from the group consisting of SEQ ID NOS: 80-94 as representatives of group 2, wherein the polypeptide comprises an amino acid residue selected from the group consisting of threonine, proline, alanine, glycine, serine, cysteine, aspartic acid, asparagine and valine, at an amino acid position corresponding to position 149 in SEQ ID NO: 1.

The term "at least 94%" is used herein to include at least 95%, such as 96%, 97%, 98%, 99% or even 100%.

The term "amino acid variant," "laccase variant" or "sequence variant" or equivalent has a meaning well recognized in the art and is accordingly used herein to indicate an amino acid sequence that has at least one amino acid difference as compared to another amino acid sequence, such as the amino acid sequence from which it was derived.

The term "at least 75%" is used herein to include at least 76%, such as at least 77%, 78%, 79%, 80% or more such as at least 81%, 82%, 83%, 84%, 85%, 86%, 87%, 88%, 89%, 90% or more, such as 91%, 92%, 93%, 94%, 95%, 96%, 97%, 98%, 99%, or even 100%.

The term "laccase activity" is used herein to mean the property of a polypeptide to act as a laccase enzyme, which may be expressed as the maximal initial rate of the specific oxidation reaction. Laccase activity may be determined by standard oxidation assays known in the art including, such as, for example, by measurement of oxidation of syringaldazine, according to Sigma online protocol, or according to Cantarella et al., 2003.[7]

An example of determining relative laccase activity is presented in Example 4. Any substrate suitable for the enzyme in question may be used in the activity measurements. A non-limiting example of a substrate suitable for use in assessing the enzymatic activity of laccase variants is ABTS (2,2'-azino-bis(3-ethylbenzothiazoline-6-sulphonic acid). Laccases are able to oxidize this substrate.

As used herein, the term "increased (or improved) laccase-specific activity" refers to a laccase activity higher than that of a corresponding non-mutated laccase enzyme under the same conditions.

The term "increased yield" or equivalent means that the yield of the active enzyme from the same culture volume obtained in a standard purification or recovery protocol is improved by at least 50% or a factor 1.5. The increase may be even more, such as a factor 2, 2.5, 3, 4, 5, 6, 7, 8, 9, 10, 11, 12, 13, 14, 15 or more.

Recovery of a laccase variant produced by a host cell may be performed by any technique known to those skilled in the art. Possible techniques include, but are not limited to, secretion of the protein into the expression medium, and purification of the protein from cellular biomass. The production method may further comprise a step of purifying the laccase variant obtained. For thermostable laccases, non-limiting examples of such methods include heating of the disintegrated cells and removing coagulated thermo-labile proteins from the solution. For secreted proteins, non-limiting examples of such methods include ion exchange chromatography, and ultra-filtration of the expression medium. It is important that the purification method of choice is such that the purified protein retains its activity, preferably its laccase activity.

The laccase variants according to this disclosure may be used in a wide range of different industrial processes and applications, such as cellulose recovery from lignocellulosic biomass, decreasing refining energy in wood refining and pulp preparation, in pulp delignification, textile dye bleaching, wastewater detoxification, xenobiotic detoxification, and detergent manufacturing.

Amino acid variations as described herein may be introduced into any of the amino acid sequences disclosed herein, or other homologous sequences, by standard methods known in the art, such as site-directed mutagenesis. In this way, the yield of the laccases from a heterologous expression system may be improved.

Kits for performing site-directed mutagenesis are commercially available in the art (e.g., QUIKCHANGE® II XL Site-Directed Mutagenesis kit by Agilent Technologies). Further suitable methods for introducing the above mutations into a recombinant gene are disclosed, e.g., in *Methods in Molecular Biology*, 2002.[8]

Thus, some embodiments of this disclosure relate to laccase variants or mutants that comprise a small amino acid residue, preferably a threonine residue (Thr) in a position that corresponds to the position 149 of the amino acid sequence depicted in SEQ ID NO: 1, and have an increased yield as compared to that of a corresponding non-mutated control when expressed in a heterologous expression system.

The term "heterologous expression system" or equivalent means a system for expressing a DNA sequence from one host organism in a recipient organism from a different species or genus than the host organism. The most prevalent recipients, known as heterologous expression systems, are usually chosen because they are easy to transfer DNA into or because they allow for a simpler assessment of the protein's function. Heterologous expression systems are also preferably used because they allow the upscaling of the production of a protein encoded by the DNA sequence in an industrial process. Preferred recipient organisms for use as heterologous expression systems include bacterial, fungal and yeast organisms, such as, for example, *Escherichia coli, Bacillus, Corynebacterium, Pseudomonas, Pichia pastoris, Saccharomyces cerevisiae, Yarrowia lipolytica, filamentus fungi* and many more systems well known in the art.

As used herein, the degree of identity between two or more amino acid sequences is equivalent to a function of the number of identical positions shared by the sequences (i.e., % identity=number of identical positions divided by the total number of positions×100), excluding gaps, which need to be introduced for optimal alignment of the two sequences, and overhangs. The comparison of sequences and determination of percent identity between two or more sequences can be accomplished using standard methods known in the art. For example, a freeware conventionally used for this purpose is "Align" tool at NCBI recourse on the World Wide Web at blast.ncbi.nlm.nih.gov/Blast.cgi?PAGE_TYPE=BlastSearch&BLAST_SPEC=blast2seq&LINK_LOC=align2seq.

In a preferred embodiment, the alignment of two sequences is to be performed over the full length of the polypeptides.

The present laccase polypeptides or proteins may be fused to additional sequences, by attaching or inserting, including, but not limited to, affinity tags, facilitating protein purification (S-tag, maltose binding domain, chitin binding domain), domains or sequences assisting folding (such as thioredoxin domain, SUMO protein), sequences affecting protein localization (periplasmic localization signals, etc.), proteins bearing additional function, such as green fluorescent protein (GFP), or sequences representing another enzymatic activity. Other suitable fusion partners for the present laccases are known to those skilled in the art.

This disclosure also relates to polynucleotides encoding any of the laccase variants disclosed herein. Means and methods for cloning and isolating such polynucleotides are well known in the art.

Furthermore, this disclosure relates to a vector comprising a polynucleotide according to the disclosure, optionally operably linked to one or more control sequences. Suitable control sequences are readily available in the art and include, but are not limited to, promoter, leader, polyadenylation, and signal sequences.

Laccase variants according to various embodiments of this disclosure may be obtained by standard recombinant methods known in the art. Briefly, such a method may comprise the steps of i) culturing a desired recombinant host cell under conditions suitable for the production of a present laccase polypeptide variant, and ii) recovering the polypeptide variant obtained. The polypeptide may then optionally be further purified.

A large number of vector-host systems known in the art may be used for recombinant production of laccase variants. Possible vectors include, but are not limited to, plasmids or modified viruses that are maintained in the host cell as autonomous DNA molecule or integrated in genomic DNA. The vector system must be compatible with the host cell used as is well known in the art. Non-limiting examples of suitable host cells include bacteria (e.g., *E. coli, bacilli*), yeast (e.g., *Pichia Pastoris, Saccharomyces Cerevisae*), fungi (e.g., *filamentous fungi*), and insect cells (e.g., Sf9).

A polypeptide according to the disclosure may be advantageously used in an application selected from the group consisting of pulp delignification, degrading or decreasing the structural integrity of lignocellulosic material, textile dye bleaching, wastewater detoxification, xenobiotic detoxification, production of a sugar from a lignocellulosic material and recovering cellulose from a biomass.

In yet other terms, the disclosure relates to a method for improving the yield of a polypeptide with laccase activity in a heterologous expression system comprising the step of altering the amino acid at a position corresponding to position 149 in SEQ ID NO: 1 to a threonine residue.

EXAMPLES

Example 1

Construction of Laccases with Improved Properties

Mutations as described herein were introduced into various recombinant genes by standard site-directed mutagenesis essentially as described in WO 2013/038062. In more detail, in order to introduce mutation 149T into the gene of SEQ ID NO: 1, two separate PCRs were carried out:

```
(1) with primers Primer1
                                        (SEQ ID NO: 25)
GAAATTAATACGACTCACTATAGG
and Primer2 (Seq1)
                                        (SEQ ID NO: 26)
AGCACCGCGTTGCTGATTCGGATAATGATA, (2) with Primer3 (Seq1)
                                        (SEQ ID NO: 27)
CGAATCAGCAACGCGGTGCTAccTTGTGGTATC
and
```

```
Primer4
                                        (SEQ ID NO: 28)
GGTTATGCTAGTTATTGCTCAGCGGTG.
```

In both reactions, recombinant gene without the mutation was used as the template. Primers 1 and 4 bind inside the vector sequence and are not specific to the recombinant gene. Primers 2 and 3 bind inside the recombinant gene and their binding sites overlap. Primer 3 binding site contains the mutation site. Primer 3 represents the mutated (desired) sequence, which is not 100% matching the template (lower case type font in the primer sequence indicate the mismatched nucleotides); however, the primer has enough affinity and specificity to the binding site to produce the desired PCR product. Purified PCR products from reactions (1) and (2) were combined and used as template for PCR reaction with Primer1 and Primer4. The product of this reaction, containing the mutant sequence of the gene, was cloned in a plasmid vector for expression in *E. coli*.

Similarly, for introducing a 149T mutation into other genes (corresponding to SEQ ID NO: 2, SEQ ID NO: 5 and SEQ ID NO: 15), the same Primer1 and Primer4 were used, whereas Primer2 and Primer3 were specific for each gene.

In the polypeptide comprising the sequence according to SEQ ID NO: 2, there is an isoleucine at position 149, the position corresponding to amino acid 149 in SEQ ID NO: 1. For introducing the 149T mutation into the polypeptide comprising the sequence according to SEQ ID NO: 2, the following primers3 and 2 were used:

```
Primer3
                                        (SEQ ID NO: 29)
CGAATCAGCAGCGCGGCGCTAccTTGTGGTATC;
and Primer2
                                        (SEQ ID NO: 30)
AGCGCCGCGCTGCTGATTCGGATAATGATA.
```

In the polypeptide comprising the sequence according to SEQ ID NO: 5, there is a leucine at position 149, the position corresponding to amino acid 149 in SEQ ID NO: 1. For introducing several mutations at position 149 into the polypeptide comprising the sequence according to SEQ ID NO: 5, the following primer2 was used in combination with the primers 3 listed in Table 2:

```
Primer2
                                        (SEQ ID NO: 31)
GCCCCGCGCTGTTTGTTTGGATAA.
```

TABLE 2

Primers used to introduce various amino acid substitutions into SEQ ID NO: 5

| Specific primer3 used to introduce variations | | Variant obtained AA change | |
|---|---|---|---|
| Primer3 sequence | SEQ ID NO: | introduced at position 149 | SEQ ID NO: |
| TCCAAACAAACAGCGCGGG GCTacGTTATGGTATCAC | 32 | Thr | 6 |
| TCCAAACAAACAGCGCGGG GCTCcGTTATGGTATCAC | 33 | Pro | 7 |

TABLE 2-continued

Primers used to introduce various amino
acid substitutions into SEQ ID NO: 5

| Specific primer3 used to introduce variations | | Variant obtained | |
|---|---|---|---|
| Primer3 sequence | SEQ ID NO: | AA change introduced at position 149 | SEQ ID NO: |
| TCCAAACAAACAGCGCGGG GCTgcGTTATGGTATCAC | 34 | Ala | 8 |
| TCCAAACAAACAGCGCGGG GCTggtTTATGGTATCAC | 35 | Gly | 9 |
| TCCAAACAAACAGCGCGGG GCTtctTTATGGTATCAC | 36 | Ser | 10 |
| TCCAAACAAACAGCGCGGG GCTtgtTTATGGTATCAC | 37 | Cys | 11 |
| TCCAAACAAACAGCGCGGG GCTgatTTATGGTATCAC | 38 | Asp | 12 |
| TCCAAACAAACAGCGCGGG GCTaacTTATGGTATCAC | 39 | Asn | 13 |
| TCCAAACAAACAGCGCGGG GCTgTGTTATGGTATCAC | 40 | Val | 14 |

In the polypeptide comprising the sequence according to SEQ ID NO: 15, there is an isoleucine at position 149, the position corresponding to amino acid 149 in SEQ ID NO: 1. For introducing a 149T mutation into the polypeptide comprising the sequence according to SEQ ID NO: 15, the following primer2 was used in combination with the various primers3 in Table 3:

```
Primer2:
                                    (SEQ ID NO: 41)
AGCACCGCGCTGCTGATTCGGATAATGATA.
```

TABLE 3

Primers used to introduce various amino
acid substitutions into SEQ ID NO: 15

| Specific primer3 used to introduce mutation | | Variant obtained | |
|---|---|---|---|
| Primer3 sequence | SEQ ID NO: | AA change introduced at position 149 | SEQ ID NO: |
| CGAATCAGCAGCGCGGTGCTAc TTTGTGGTATCACGATCACGC | 42 | Thr | 16 |
| CGAATCAGCAGCGCGGTGCTcc gTTGTGGTATCACGATCACGC | 43 | Pro | 17 |
| CGAATCAGCAGCGCGGTGCTgc gTTGTGGTATCACGATCACGC | 44 | Ala | 18 |
| CGAATCAGCAGCGCGGTGCTgg TTTGTGGTATCACGATCACGC | 45 | Gly | 19 |
| CGAATCAGCAGCGCGGTGCTtc TTTGTGGTATCACGATCACGC | 46 | Ser | 20 |
| CGAATCAGCAGCGCGGTGCTtg TTTGTGGTATCACGATCACGC | 47 | Cys | 21 |

TABLE 3-continued

Primers used to introduce various amino
acid substitutions into SEQ ID NO: 15

| Specific primer3 used to introduce mutation | | Variant obtained | |
|---|---|---|---|
| Primer3 sequence | SEQ ID NO: | AA change introduced at position 149 | SEQ ID NO: |
| CGAATCAGCAGCGCGGTGCTga TTTGTGGTATCACGATCACGC | 48 | Asp | 22 |
| CGAATCAGCAGCGCGGTGCTAa cTTGTGGTATCACGATCACGC | 49 | Asn | 23 |
| CGAATCAGCAGCGCGGTGCTgT gTTGTGGTATCACGATCACGC | 50 | Val | 24 |

Example 2

Heterologous Expression of Variant and Non-Mutated Laccases

Variant laccases were expressed in *E. coli* and *Pichia pastoris*.

For expression in *Pichia Pastoris*, recombinant genes were cloned into a commercial *Pichia Pastoris* expression vector pPICZ-A, available from Invitrogen (Life Technologies). This vector provides secreted protein expression under the control of methanol-inducible AOX1 promoter upon integration of the construct into genomic DNA of the yeast cell.

Linearized plasmid DNA was introduced into yeast cells by electroporation, and clones with integrated recombinant gene were selected on agar medium plates with Zeocin (25 µg/ml). Ten colonies from each construct were tested in small liquid cultures (3 ml) with a 72-hour cultivation in humidified shaker at 28° C. according to the plasmid manufacturer manual (World Wide Web at tools.lifetechnologies.com/content/sfs/manuals/ppiczalpha_man.pdf). The medium recommended by the manufacturer was supplemented with 1 mM CuCl, as laccase protein contains copper as a cofactor. Activity in the medium was measured by ABTS oxidation (see Example 4), and the two best-producing clones were selected for each gene. Parallel cultures of the selected clones were grown in flask scale according to the plasmid manufacturer manual (see above) at 28° C. for 105 hours. Cells were removed by centrifugation and medium containing the recombinant protein was collected. These preparations were used for comparison of volumetric activities of variant and non-mutated genes.

For recombinant expression in *E. coli*, recombinant genes were cloned into pET-28 commercial expression vector under the control of T7 bacteriophage promoter. Protein production was carried out in *E. coli* BL21(DE3) strain according to the plasmid manufacturer protocol on the World Wide Web at richsingiser.com/4402/Novagen %20pET %20system %20manual.pdf. The medium recommended by the manufacturer was supplemented with 1 mM CuCl, as laccase protein contains copper as a cofactor. The incubation temperature for protein production was 30° C., which was found optimal for maximum yield of the active protein. Cells were lysed using lysis buffer (50 mM Tris-HCl pH 7.4, 1% TRITON®-X100, 1 mM CuCl) and heated at 70° C. for 20 minutes. Coagulated cell debris was removed by centrifugation. The recombinant laccase, being a thermostable protein, remained in soluble fraction. Enzymatic activity was detectable only in soluble fraction. Analysis of soluble and insoluble fractions by gel-electrophoresis reveals that over 90% of the recombinant protein is present in insoluble inactive form as inclusion bodies (in accordance with literature data).

Example 3

Measurement of Yield

The relative yields of mutated and non-mutated soluble laccases were determined by densitometry of protein bands after denaturing polyacrylamide gel electrophoresis. To this end, samples of soluble proteins after thermal treatment (see Example 2) obtained from parallel cultures of mutated and non-mutated clones, were analyzed by gel-electrophoresis under denaturing conditions (a standard method well known in the art of molecular biology). After staining the gel with Coomassie Brilliant Blue, the gel was scanned to obtain a bitmap image, and intensity of the band corresponding to recombinant laccase was quantified by ImageJ software (a public freeware developed at National Institute of Health and online available on the World Wide Web at imagej.nih.gov/ij/).

Example 4

Relative Activity Measurement of Laccase

As stated above, the term "laccase activity" is used herein to mean the capability to act as a laccase enzyme, which may be expressed as the maximal initial rate of the specific oxidation reaction. Relative activity was measured by oxidation of ABTS (2,2'-azino-bis(3-ethylbenzothiazoline-6-sulphonic acid). Reaction course was monitored by change in absorbance at 405 nM (green color development). The appropriate reaction time was determined to provide initial rates of oxidation when color development is linear with time. Substrate (ABTS) concentration was 5 mM to provide maximum initial rates (substrate saturation conditions).

Typically, reactions were carried out in 96-well flat bottom plates, each well containing 2 µl of enzyme preparation in 200 µl of 100 mM Succinic acid pH 5. The reaction was initiated by simultaneous addition of the substrate (22 µl of 50 mM ABTS) in each well. After the reaction time has elapsed, absorbance at 405 nm of the reaction mixtures was determined by a plate reader (Multiscan Go, Thermo Scientific). In order to determine relative activity of mutated laccase, the absorbance of the reference laccase sample was taken for 100%, and relative activity was determined as fraction of this absorbance.

Example 5

Identification of the Amino Acid Position Corresponding to Position 149

In order to identify the amino acid position that corresponds to position 149 in SEQ ID NO: 1 in a given sequence X, the sequence X is aligned with the sequence of SEQ ID NO: 1 using standard software available in the art, in this case the "Align" tool at NCBI recourse on the World Wide Web at blast.ncbi.nlm.nih.gov/Blast.cgi?PAGE_TYPE=BlastSearch&BLAST_SPEC=blast2seq&LINK_LOC=align2seq.

As an example, sequences 51-94 were aligned with SEQ ID NO: 1. Only a fragment of that alignment is shown in Table 4, i.e., the fragment corresponding to amino acids 125-152 of SEQ ID NO: 1. It is immediately evident that this particular region is highly conserved or highly homologous between the various sequences provided in the table, leading to a high degree of identity in all examined sequences. For example, the isoleucine (I) residue at position 149 of SEQ ID NO: 1 corresponds to an isoleucine residue at position 149 in SEQ ID NO: 51, to an isoleucine residue at position 151 in SEQ ID NO: 56, and to a leucine residue (L) at position 149 in SEQ ID NO: 85. The position of the first and last amino acid of each fragment is shown in Table 4. The amino acid corresponding to position 149 in SEQ ID NO: 1 in each fragment is indicated in bold.

Sequences of SEQ ID NO: 1 to SEQ ID NO: 24 are shown in Table 5.

TABLE 4

Alignment of SEQ ID NO: 1 with SEQ ID NOS: 51-94, fragments 125-152 of the alignment are shown. The amino acid at the position corresponding to amino acid 149 in SEQ ID NO: 1 is shown in bold.

| Accession No: | First AA | Sequence corresponding to AA 125-152 of SEQ ID NO: 1. | Last AA | SEQ ID NO: | Fragment of SEQ ID NO: |
|---|---|---|---|---|---|
| SEQ ID NO: 1 | 125 | KDFEQTGPYFKREVYHYPNQQRGAILWY | 152 | 95 | 1 |
| AGZ16504.1 | 125 | KDFEQTGPYFKREVYHYPNQQRGAILWY | 152 | 96 | 51 |
| YP_003865004.1 | 125 | KDFEQTGPYFKREVYHYPNQQRGAILWY | 152 | 97 | 52 |
| WP_004397739.1 | 125 | KDFEQTGPYFKREVYHYPNQQRGAILWY | 152 | 98 | 53 |
| WP_019713492.1 | 125 | KDFEQTGPYFKREVYHYPNQQRGAILWY | 152 | 99 | 54 |
| AGR50961.1 | 125 | KDFEQTGPYFKREVYHYPNQQRGAILWY | 152 | 100 | 55 |
| YP_007425830.1 | 127 | KDFEQTGPYFKREVYHYPNQQRGAILWY | 154 | 101 | 56 |
| YP_004206641.1 | 125 | KDFEQTGPYFKREVYHYPNQQRGAILWY | 152 | 102 | 57 |
| YP_006230497.1 | 125 | KDFEQTGPYFKREVYHYPNQQRGAILWY | 152 | 103 | 58 |
| EXF51833.1 | 125 | KDFEQTGPYFKREVYHYPNQQRGAILWY | 152 | 104 | 59 |

TABLE 4-continued

Alignment of SEQ ID NO: 1 with SEQ ID NOS: 51-94, fragments 125-152 of the alignment are shown. The amino acid at the position corresponding to amino acid 149 in SEQ ID NO: 1 is shown in bold.

| Accession No: | First AA | Sequence corresponding to AA 125-152 of SEQ ID NO: 1. | Last AA | SEQ ID NO: | Fragment of SEQ ID NO: |
|---|---|---|---|---|---|
| WP_003234000.1 | 127 | KDFEQTGPYFKREVYHYPNQQRGAILWY | 154 | 105 | 60 |
| YP_006628799.1 | 127 | KDFEQTGPYFKREVYHYPNQQRGAILWY | 154 | 106 | 61 |
| NP_388511.1 | 125 | KDFEQTGPYFKREVYHYPNQQRGAILWY | 152 | 107 | 62 |
| YP_007661398.1 | 125 | KDFEQTGPYFKREVYHYPNQQRGAILWY | 152 | 108 | 63 |
| 4AKQ_A | 125 | KDFEQTGPYFKREVYHYPNQQRGAILWY | 152 | 109 | 64 |
| 4A68_A | 125 | KDFEQTGPYFKREVYHYPNQQRGAILWY | 152 | 110 | 65 |
| 4A66_A | 125 | KDFEQTGPYFKREVYHYPNQQRGAILWY | 152 | 111 | 66 |
| AC544284.1 | 125 | KDFEQTGPYFKREVYHYPNQQRGAILWY | 152 | 112 | 67 |
| AGK12417.1 | 125 | KDLEQTGPYFKREVYHYPNQQRGAILWY | 152 | 113 | 68 |
| 2X87_A | 125 | KDFEQTGPYFKREVYHYPNQQRGAILWY | 152 | 114 | 69 |
| AFN66123.1 | 125 | KDFEQTGPYFKREVYHYPNQQRGAILWY | 152 | 115 | 70 |
| 4A67_A | 125 | KDFEQTGPYFKREVYHYPNQQRGAILWY | 152 | 116 | 71 |
| 2WSD_A | 125 | KDFEQTGPYFKREVYHYPNQQRGAILWY | 152 | 117 | 72 |
| 4AKP_A | 125 | KDFEQTGPYFKREVYHYPNQQRGAILWY | 152 | 118 | 73 |
| ACM46021.1 | 125 | KDFEQTGPYFKREVYHYPNQQRGAILWY | 152 | 119 | 74 |
| WP_010329056.1 | 125 | KDFEQTGPYFKREIYHYPNQQRGAILWY | 152 | 120 | 75 |
| AEK80414.1 | 125 | KDFEQTGPYFKREVYHYPNQQRGAILWY | 152 | 121 | 76 |
| WP_010333230.1 | 125 | KDFEQTGPYFKREVYHYPNQQRGAILWY | 152 | 122 | 77 |
| 4AKO_A | 121 | KDFEQTGPYFKREVYHYPNQQRGAILWY | 148 | 123 | 78 |
| AAB62305.1 | 125 | KDFEQTGPYFKREVYHYPNQQRGAILWY | 152 | 124 | 79 |
| YP_003972023.1 | 125 | KGFQETGPYFSREIYHYPNQQRGAILWY | 152 | 125 | 80 |
| WP_010787813.1 | 125 | KGFQETGPYFSREIYHYPNQQRGAILWY | 152 | 126 | 81 |
| WP_007609818.1 | 125 | KDFKETGPYFEKEVYHYPNKQRGALLWY | 152 | 127 | 82 |
| YP_007496315.1 | 125 | KDFKETGPYFEREVYHYPNKQRGALLWY | 152 | 128 | 83 |
| YP_005419918.1 | 125 | KDFKETGPYFEKEVYHYPNKQRGALLWY | 152 | 129 | 84 |
| YP_008625231.1 | 125 | KDFKETGPYFEKEVYHYPNKQRGALLWY | 152 | 130 | 85 |
| YP_007185316.1 | 125 | KDFKETGPYFEREVYHYPNKQRGALLWY | 152 | 131 | 86 |
| YP_001420286.1 | 125 | KDFKETGPYFEREVYHYPNKQRGALLWY | 152 | 132 | 87 |
| ADZ57286.1 | 125 | KDFKETGPYFEKEVYHYPNKQRGALLWY | 152 | 133 | 88 |
| WP_007408880.1 | 125 | KDFKETGPYFEREVYHYPNKQRGALLWY | 152 | 134 | 89 |
| WP_021495201.1 | 125 | KDFKETGPYFEKEVYHYPNKQRGALLWY | 152 | 135 | 90 |
| YP_005129370.1 | 125 | KDFKETGPYFEREVYHYPNKQRGALLWY | 152 | 136 | 91 |
| AHK48246.1 | 125 | KDFKETGPYFEREVYHYPNKQRGALLWY | 152 | 137 | 92 |
| YP_003919218.1 | 125 | RDFKEKGPYFEKEVYHYPNKQRGALLWY | 152 | 138 | 93 |
| WP_016937040.1 | 125 | RDFKETGPYFEKEVYHYPNKQRGALLWY | 152 | 139 | 94 |

TABLE 5

Sequences of SEQ ID NOS: 1-24.

| SEQ ID NO: | Name | Organism | Sequence |
|---|---|---|---|
| 1 | Cot1 | Bacillus subtilis | MTLEKFVDALPIPDTLKPVQQTTEKTYYEVTMEECAHQLHRDLPPTRLW<br>GYNGLFPGPTIEVKRNENVYVKWMNNLPSEHFLPIDHTIHHSDSQHEEP<br>EVKTVVHLHGGVTPDDSDGYPEAWFSKDFEQTGPYFKREVYHYPNQQRG<br>AILWYHDHAMALTRLNVYAGLVGAYIIHDPKEKRLKLPSGEYDVPLLIT<br>DRTINEDGSLFYPSGPENPSPSLPKPSIVPAFCGDTILVNGKVWPYLEV<br>EPRKYRFRVINASNTRTYNLSLDNGGEFIQIGSDGGLLPRSVKLNSFSL<br>APAERYDIIIDFTAYEGESIILANSEGCGGDANPETDANIMQFRVTKPL<br>AQKDESRKPKYLASYPSVQNERIQNIRTLKLAGTQDEYGRPVLLLNNKR<br>WHDPVTEAPKAGTTEIWSIVNPTQGTHPIHLHLVSFRVLDRRPFDIARY<br>QERGELSYTGPAVPPPPSEKGWKDTIQAHAGEVLRIAVTFGPYSGRYVW<br>HCHILEHEDYDMMRPMDITDPHK |
| 2 | Cot2 | Bacillus subtilis | MTLEKFVDALPIPDTLKPVQQSKEKTYYEVTMEECTHQLHRDLPPTRLW<br>GYNGLFPGPTIEVKRNENVYVKWMNNLPSTHFLPIDHTIHHSDSQHEEP<br>EVKTVVHLHGGVTPDDSDGYPEAWFSKDFEQTGPYFKREVYHYPNQQRG<br>AILWYHDHAMALTRLNVYAGLVGAYIIHDPKEKRLKLPSEEYDVPLLIT<br>DRTINEDGSLFYPSGPENPSPSLPNPSIVPAFCGETILVNGKVWPYLEV<br>EPRKYRFRVINASNTRTYNLSLDNGGEFIQIGSDGGLLPRSVKLTSFSL<br>APAERYDIIIDFTAYEGQSIILANSAGCGGDVNPETDANIMQFRVTKPL<br>AQKDESRKPKYLASYPSVQNERIQNIRTLKLAGTQDEYGRPVLLLNNKR<br>WHDPVTEAPKAGTTEIWSIINPTRGTHPIHLHLVSFRVIDRRPFDIAHY<br>QESGALSYTGPAVPPPPSEKGWKDTIQAHAGEVLRIAATFGPYSGRYVW<br>HCHILEHEDYDMMRPMDITDPHKSDPNSSSVDKLHRTRAPPPPPLRSGC |
| 3 | Cot1 149T | Bacillus subtilis | MTLEKFVDALPIPDTLKPVQQTTEKTYYEVTMEECAHQLHRDLPPTRLW<br>GYNGLFPGPTIEVKRNENVYVKWMNNLPSERFLPIDHTIHHSDSQHEEP<br>EVKTVVHLHGGVTPDDSDGYPEAWFSKDFEQTGPYFKREVYHYPNQQRG<br>ATLWYHDHAMALTRLNVYAGLVGAYIIHDPKEKRLKLPSGEYDVPLLIT<br>DRTINEDGSLFYPSGPENPSPSLPKPSIVPAFCGDTILVNGKVWPYLEV<br>EPRKYRFRVINASNTRTYNLSLDNGGEFIQIGSDGGLLPRSVKLNSFSL<br>APAERYDIIIDFTAYEGESIILANSEGCGGDANPETDANIMQFRVTKPL<br>AQKDESRKPKYLASYPSVQNERIQNIRTLKLAGTQDEYGRPVLLLNNKR<br>WHDPVTEAPKAGTTEIWSIVNPTQGTHPIHLHLVSFRVLDRRPFDIARY<br>QERGELSYTGPAVPPPPSEKGWKDTIQAHAGEVLRIAVTFGPYSGRYVW<br>HCHILEHEDYDMMRPMDITDPHK |
| 4 | Cot2 149T | Bacillus subtilis | MTLEKFVDALPIPDTLKPVQQSKEKTYYEVTMEECTHQLHRDLPPTRLW<br>GYNGLFPGPTIEVKRNENVYVKWMNNLPSTHFLPIDHTIHHSDSQHEEP<br>EVKTVVHLHGGVTPDDSDGYPEAWFSKDFEQTGPYFKREVYHYPNQQRG<br>ATLWYHDHAMALTRLNVYAGLVGAYIIHDPKEKRLKLPSEEYDVPLLIT<br>DRTINEDGSLFYPSGPENPSPSLPNPSIVPAFCGETILVNGKVWPYLEV<br>EPRKYRFRVINASNTRTYNLSLDNGGEFIQIGSDGGLLPRSVKLTSFSL<br>APAERYDIIIDFTAYEGQSIILANSAGCGGDVNPETDANIMQFRVTKPL<br>AQKDESRKPKYLASYPSVQNERIQNIRTLKLAGTQDEYGRPVLLLNNKR<br>WHDPVTEAPKAGTTEIWSIINPTRGTHPIHLHLVSFRVIDRRPFDIAHY<br>QESGALSYTGPAVPPPPSEKGWKDTIQAHAGEVLRIAATFGPYSGRYVW<br>HCHILEHEDYDMMRPMDITDPHKSDPNSSSVDKLHRTRAPPPPPLRSGC |
| 5 | seq 61 | Bacillus amyloliquefaciens | MALEKFADELPIIETLQPQKKSDGSTYYEVTMKECFHKLHRDLPPTRLW<br>GYNGLFPGPTIDVNKDENVYIKWMNDLPDKHFLPVDHTIHHSESGHQEP<br>DVKTVVHLHGGATPPDSDGYPEAWFTKDFKETGPYFEREVYHYPNKQRG<br>ALLWYHDHAMAITRLNVYAGLAGMYIIRERKEKQLKLPSGEYDVPLMIL<br>DRTLNDDGSLSYPSGPANPSETLPDPSIVPFFCGNTILVNGKAWPYMEV<br>EPRTYRFRILNASNTRTFSLSLNNGGKFIQIGSDGGLLPRSVKTQSISL<br>APAERYDVLIDFSAFDGEHIILTNGTGCGGDADPDTDANVMQFRVTKPL<br>KGADTSRKPKYLSTMPNVTSKRIHNIRMLKLTNTQDKYGRPVLTLNNKR<br>WHDPVTEAPKLGTTEIWSIINPMGGTHPIHLHLVSFQILDRRPFDLERY<br>NKFGDIVYTGPAVPPPPSEKGWKDTVQAHSGEVIRIAATFAPYSGRYVW<br>HCHILEHEDYDMMRPMDVTDKQ |
| 6 | seq 61 149T | Bacillus amyloliquefaciens | MALEKFADELPIIETLQPQKKSDGSTYYEVTMKECFHKLHRDLPPTRLW<br>GYNGLFPGPTIDVNKDENVYIKWMNDLPDKHFLPVDHTIHHSESGHQEP<br>DVKTVVHLHGGATPPDSDGYPEAWFTKDFKETGPYFEREVYHYPNKQRG<br>ATLWYHDHAMAITRLNVYAGLAGMYIIRERKEKQLKLPSGEYDVPLMIL<br>DRTLNDDGSLSYPSGPANPSETLPDPSIVPFFCGNTILVNGKAWPYMEV<br>EPRTYRFRILNASNTRTFSLSLNNGGKFIQIGSDGGLLPRSVKTQSISL<br>APAERYDVLIDFSAFDGEHIILTNGTGCGGDADPDTDANVMQFRVTKPL<br>KGADTSRKPKYLSTMPNVTSKRIHNIRMLKLTNTQDKYGRPVLTLNNKR<br>WHDPVTEAPKLGTTEIWSIINPMGGTHPIHLHLVSFQILDRRPFDLERY<br>NKFGDIVYTGPAVPPPPSEKGWKDTVQAHSGEVIRIAATFAPYSGRYVW<br>HCHILEHEDYDMMRPMDVTDKQ |
| 7 | seq 61 149P | Bacillus amyloliquefaciens | MALEKFADELPIIETLQPQKKSDGSTYYEVTMKECFHKLHRDLPPTRLW<br>GYNGLFPGPTIDVNKDENVYIKWMNDLPDKHFLPVDHTIHHSESGHQEP<br>DVKTVVHLHGGATPPDSDGYPEAWFTKDFKETGPYFEREVYHYPNKQRG |

TABLE 5-continued

Sequences of SEQ ID NOS: 1-24.

| SEQ ID NO: | Name | Organism | Sequence |
|---|---|---|---|
| | | | APLWYHDHAMAITRLNVYAGLAGMYIIRERKEKQLKLPSGEYDVPLMIL<br>DRTLNDDGSLSYPSGPANPSETLPDPSIVPFFCGNTILVNGKAWPYMEV<br>EPRTYRFRILNASNTRTFSLSLNNGGKFIQIGSDGGLLPRSVKTQSISL<br>APAERYDVLIDFSAFDGEHIILTNGTGCGGDADPDTDANVMQFRVTKPL<br>KGADTSRKPKYLSTMPNVTSKRIHNIRMLKLTNTQDKYGRPVLTLNNKR<br>WHDPVTEAPKLGTTEIWSIINPMGGTHPIHLHLVSFQILDRRPFDLERY<br>NKFGDIVYTGPAVPPPPSEKGWKDTVQAHSGEVIRIAATFAPYSGRYVW<br>HCHILEHEDYDMMRPMDVTDKQ |
| 8 | seq 61 149A | Bacillus amyloliquefaciens | MALEKFADELPIIETLQPQKKSDGSTYYEVTMKECFHKLHRDLPPTRLW<br>GYNGLFPGPTIDVNKDENVYIKWMNDLPDKHFLPVDHTIHHSESGHQEP<br>DVKTVVHLHGGATPPDSDGYPEAWFTKDFKETGPYFEREVYHYPNKQRG<br>AALWYHDHAMAITRLNVYAGLAGMYIIRERKEKQLKLPSGEYDVPLMIL<br>DRTLNDDGSLSYPSGPANPSETLPDPSIVPFFCGNTILVNGKAWPYMEV<br>EPRTYRFRILNASNTRTFSLSLNNGGKFIQIGSDGGLLPRSVKTQSISL<br>APAERYDVLIDFSAFDGEHIILTNGTGCGGDADPDTDANVMQFRVTKPL<br>KGADTSRKPKYLSTMPNVTSKRIHNIRMLKLTNTQDKYGRPVLTLNNKR<br>WHDPVTEAPKLGTTEIWSIINPMGGTHPIHLHLVSFQILDRRPFDLERY<br>NKFGDIVYTGPAVPPPPSEKGWKDTVQAHSGEVIRIAATFAPYSGRYVW<br>HCHILEHEDYDMMRPMDVTDKQ |
| 9 | seq 61 149G | Bacillus amyloliquefaciens | MALEKFADELPIIETLQPQKKSDGSTYYEVTMKECFHKLHRDLPPTRLW<br>GYNGLFPGPTIDVNKDENVYIKWMNDLPDKHFLPVDHTIHHSESGHQEP<br>DVKTVVHLHGGATPPDSDGYPEAWFTKDFKETGPYFEREVYHYPNKQRG<br>AGLWYHDHAMAITRLNVYAGLAGMYIIRERKEKQLKLPSGEYDVPLMIL<br>DRTLNDDGSLSYPSGPANPSETLPDPSIVPFFCGNTILVNGKAWPYMEV<br>EPRTYRFRILNASNTRTFSLSLNNGGKFIQIGSDGGLLPRSVKTQSISL<br>APAERYDVLIDFSAFDGEHIILTNGTGCGGDADPDTDANVMQFRVTKPL<br>KGADTSRKPKYLSTMPNVTSKRIHNIRMLKLTNTQDKYGRPVLTLNNKR<br>WHDPVTEAPKLGTTEIWSIINPMGGTHPIHLHLVSFQILDRRPFDLERY<br>NKFGDIVYTGPAVPPPPSEKGWKDTVQAHSGEVIRIAATFAPYSGRYVW<br>HCHILEHEDYDMMRPMDVTDKQ |
| 10 | seq 61 149S | Bacillus amyloliquefaciens | MALEKFADELPIIETLQPQKKSDGSTYYEVTMKECFHKLHRDLPPTRLW<br>GYNGLFPGPTIDVNKDENVYIKWMNDLPDKHFLPVDHTIHHSESGHQEP<br>DVKTVVHLHGGATPPDSDGYPEAWFTKDFKETGPYFEREVYHYPNKQRG<br>ASLWYHDHAMAITRLNVYAGLAGMYIIRERKEKQLKLPSGEYDVPLMIL<br>DRTLNDDGSLSYPSGPANPSETLPDPSIVPFFCGNTILVNGKAWPYMEV<br>EPRTYRFRILNASNTRTFSLSLNNGGKFIQIGSDGGLLPRSVKTQSISL<br>APAERYDVLIDFSAFDGEHIILTNGTGCGGDADPDTDANVMQFRVTKPL<br>KGADTSRKPKYLSTMPNVTSKRIHNIRMLKLTNTQDKYGRPVLTLNNKR<br>WHDPVTEAPKLGTTEIWSIINPMGGTHPIHLHLVSFQILDRRPFDLERY<br>NKFGDIVYTGPAVPPPPSEKGWKDTVQAHSGEVIRIAATFAPYSGRYVW<br>HCHILEHEDYDMMRPMDVTDKQ |
| 11 | seq 61 149C | Bacillus amyloliquefaciens | MALEKFADELPIIETLQPQKKSDGSTYYEVTMKECFHKLHRDLPPTRLW<br>GYNGLFPGPTIDVNKDENVYIKWMNDLPDKHFLPVDHTIHHSESGHQEP<br>DVKTVVHLHGGATPPDSDGYPEAWFTKDFKETGPYFEREVYHYPNKQRG<br>ACLWYHDHAMAITRLNVYAGLAGMYIIRERKEKQLKLPSGEYDVPLMIL<br>DRTLNDDGSLSYPSGPANPSETLPDPSIVPFFCGNTILVNGKAWPYMEV<br>EPRTYRFRILNASNTRTFSLSLNNGGKFIQIGSDGGLLPRSVKTQSISL<br>APAERYDVLIDFSAFDGEHIILTNGTGCGGDADPDTDANVMQFRVTKPL<br>KGADTSRKPKYLSTMPNVTSKRIHNIRMLKLTNTQDKYGRPVLTLNNKR<br>WHDPVTEAPKLGTTEIWSIINPMGGTHPIHLHLVSFQILDRRPFDLERY<br>NKFGDIVYTGPAVPPPPSEKGWKDTVQAHSGEVIRIAATFAPYSGRYVW<br>HCHILEHEDYDMMRPMDVTDKQ |
| 12 | seq 61 149D | Bacillus amyloliquefaciens | MALEKFADELPIIETLQPQKKSDGSTYYEVTMKECFHKLHRDLPPTRLW<br>GYNGLFPGPTIDVNKDENVYIKWMNDLPDKHFLPVDHTIHHSESGHQEP<br>DVKTVVHLHGGATPPDSDGYPEAWFTKDFKETGPYFEREVYHYPNKQRG<br>ADLWYHDHAMAITRLNVYAGLAGMYIIRERKEKQLKLPSGEYDVPLMIL<br>DRTLNDDGSLSYPSGPANPSETLPDPSIVPFFCGNTILVNGKAWPYMEV<br>EPRTYRFRILNASNTRTFSLSLNNGGKFIQIGSDGGLLPRSVKTQSISL<br>APAERYDVLIDFSAFDGEHIILTNGTGCGGDADPDTDANVMQFRVTKPL<br>KGADTSRKPKYLSTMPNVTSKRIHNIRMLKLTNTQDKYGRPVLTLNNKR<br>WHDPVTEAPKLGTTEIWSIINPMGGTHPIHLHLVSFQILDRRPFDLERY<br>NKFGDIVYTGPAVPPPPSEKGWKDTVQAHSGEVIRIAATFAPYSGRYVW<br>HCHILEHEDYDMMRPMDVTDKQ |
| 13 | seq 61 149N | Bacillus amyloliquefaciens | MALEKFADELPIIETLQPQKKSDGSTYYEVTMKECFHKLHRDLPPTRLW<br>GYNGLFPGPTIDVNKDENVYIKWMNDLPDKHFLPVDHTIHHSESGHQEP<br>DVKTVVHLHGGATPPDSDGYPEAWFTKDFKETGPYFEREVYHYPNKQRG<br>ANLWYHDHAMAITRLNVYAGLAGMYIIRERKEKQLKLPSGEYDVPLMIL<br>DRTLNDDGSLSYPSGPANPSETLPDPSIVPFFCGNTILVNGKAWPYMEV<br>EPRTYRFRILNASNTRTFSLSLNNGGKFIQIGSDGGLLPRSVKTQSISL |

TABLE 5-continued

Sequences of SEQ ID NOS: 1-24.

| SEQ ID NO: | Name | Organism | Sequence |
|---|---|---|---|
| | | | APAERYDVLIDFSAFDGEHIILTNGTGCGGDADPDTDANVMQFRVTKPL KGADTSRKPKYLSTMPNVTSKRIHNIRMLKLTNTQDKYGRPVLTLNNKR WHDPVTEAPKLGTTEIWSIINPMGGTHPIHLHLVSFQILDRRPFDLERY NKFGDIVYTGPAVPPPPSEKGWKDTVQAHSGEVIRIAATFAPYSGRYVW HCHILEHEDYDMMRPMDVTDKQ |
| 14 | seq 61 149V | Bacillus amylo-liquefaciens | MALEKFADELPIIETLQPQKKSDGSTYYEVTMKECFHKLHRDLPPTRLW GYNGLFPGPTIDVNKDENVYIKWMNDLPDKHFLPVDHTIHHSESGHQEP DVKTVVHLHGGATPPDSDGYPEAWFTKDFPKETGPYFEREVYHYPNKQRG AVLWYHDHAMAITRLNVYAGLAGMYIIRERKEKQLKLPSGEYDVPLMIL DRTLNDDGSLSYPSGPANPSETLPDPSIVPFFCGNTILVNGKAWPYMEV EPRTYRFRILNASNTRTFSLSLNNGGKFIQIGSDGGLLPRSVKTQSISL APAERYDVLIDFSAFDGEHIILTNGTGCGGDADPDTDANVMQFRVTKPL KGADTSRKPKYLSTMPNVTSKRIHNIRMLKLTNTQDKYGRPVLTLNNKR WHDPVTEAPKLGTTEIWSIINPMGGTHPIHLHLVSFQILDRRPFDLERY NKFGDIVYTGPAVPPPPSEKGWKDTVQAHSGEVIRIAATFAPYSGRYVW HCHILEHEDYDMMRPMDVTDKQ |
| 15 | Seq 49 | Bacillus vallismortis | MTLEKFVDALPIPETLKPVQQTKEKTYYEVTMEECAHKLHRDLPPTRLW GYNCQFPGPTIEVNRNENVYVKWMNHLSSTHFLPVDHTIHRSDSQHEEP EVKTVVHLHGGVTPEDSDGYPEAWFTKDFEQTGPYFKREIYHYPNQQRG AILWYHDHAMALTRLNVYAGLIGAYLIHDPKEKRLKLPSGEYDVPLLIT DRTINGDGSLFYPNGPENPSPSLPNPSIVPAFCGETILVNGKAWPYLEV EPRKYRFRVINASNTRTYNLSLDNDGEFIQIGSDGGLLPRSVKLNSFSL APAERYDIIIDFTAYEGQSIILANSEGCGGDANPETDANIMQFRVTKPL AQKDESRKPKYLASYPSVQNERIHNIRTLKLAGTQDEYGRPVLLLNNKR WHDPVTETPKAGTTEIWSIINPTRGTHPIHLHLVSFRVLDRRPFDIARY QERGELSYTGPAVPPPPSEKGWKDTIQAHAGEVLRIAATFGPYSGRYVW HCHILEHEDYDMMRPMDITDPHK |
| 16 | Seq 49 149T | Bacillus vallismortis | MTLEKFVDALPIPETLKPVQQTKEKTYYEVTMEECAHKLHRDLPPTRLW GYNCQFPGPTIEVNRNENVYVKWMNHLSSTHFLPVDHTIHRSDSQHEEP EVKTVVHLHGGVTPEDSDGYPEAWFTKDFEQTGPYFKREIYHYPNQQRG ATLWYHDHAMALTRLNVYAGLIGAYLIHDPKEKRLKLPSGEYDVPLLIT DRTINGDGSLFYPNGPENPSPSLPNPSIVPAFCGETILVNGKAWPYLEV EPRKYRFRVINASNTRTYNLSLDNDGEFIQIGSDGGLLPRSVKLNSFSL APAERYDIIIDFTAYEGQSIILANSEGCGGDANPETDANIMQFRVTKPL AQKDESRKPKYLASYPSVQNERIHNIRTLKLAGTQDEYGRPVLLLNNKR WHDPVTETPKAGTTEIWSIINPTRGTHPIHLHLVSFRVLDRRPFDIARY QERGELSYTGPAVPPPPSEKGWKDTIQAHAGEVLRIAATFGPYSGRYVW HCHILEHEDYDMMRPMDITDPHK |
| 17 | Seq 49 149P | Bacillus vallismortis | MTLEKFVDALPIPETLKPVQQTKEKTYYEVTMEECAHKLHRDLPPTRLW GYNCQFPGPTIEVNRNENVYVKWMNHLSSTHFLPVDHTIHRSDSQHEEP EVKTVVHLHGGVTPEDSDGYPEAWFTKDFEQTGPYFKREIYHYPNQQRG APLWYHDHAMALTRLNVYAGLIGAYLIHDPKEKRLKLPSGEYDVPLLIT DRTINGDGSLFYPNGPENPSPSLPNPSIVPAFCGETILVNGKAWPYLEV EPRKYRFRVINASNTRTYNLSLDNDGEFIQIGSDGGLLPRSVKLNSFSL APAERYDIIIDFTAYEGQSIILANSEGCGGDANPETDANIMQFRVTKPL AQKDESRKPKYLASYPSVQNERIHNIRTLKLAGTQDEYGRPVLLLNNKR WHDPVTETPKAGTTEIWSIINPTRGTHPIHLHLVSFRVLDRRPFDIARY QERGELSYTGPAVPPPPSEKGWKDTIQAHAGEVLRIAATFGPYSGRYVW HCHILEHEDYDMMRPMDITDPHK |
| 18 | Seq 49 149A | Bacillus vallismortis | MTLEKFVDALPIPETLKPVQQTKEKTYYEVTMEECAHKLHRDLPPTRLW GYNCQFPGPTIEVNRNENVYVKWMNHLSSTHFLPVDHTIHRSDSQHEEP EVKTVVHLHGGVTPEDSDGYPEAWFTKDFEQTGPYFKREIYHYPNQQRG AALWYHDHAMALTRLNVYAGLIGAYLIHDPKEKRLKLPSGEYDVPLLIT DRTINGDGSLFYPNGPENPSPSLPNPSIVPAFCGETILVNGKAWPYLEV EPRKYRFRVINASNTRTYNLSLDNDGEFIQIGSDGGLLPRSVKLNSFSL APAERYDIIIDFTAYEGQSIILANSEGCGGDANPETDANIMQFRVTKPL AQKDESRKPKYLASYPSVQNERIHNIRTLKLAGTQDEYGRPVLLLNNKR WHDPVTETPKAGTTEIWSIINPTRGTHPIHLHLVSFRVLDRRPFDIARY QERGELSYTGPAVPPPPSEKGWKDTIQAHAGEVLRIAATFGPYSGRYVW HCHILEHEDYDMMRPMDITDPHK |
| 19 | Seq 49 149G | Bacillus vallismortis | MTLEKFVDALPIPETLKPVQQTKEKTYYEVTMEECAHKLHRDLPPTRLW GYNCQFPGPTIEVNRNENVYVKWMNHLSSTHFLPVDHTIHRSDSQHEEP EVKTVVHLHGGVTPEDSDGYPEAWFTKDFEQTGPYFKREIYHYPNQQRG AGLWYHDHAMALTRLNVYAGLIGAYLIHDPKEKRLKLPSGEYDVPLLIT DRTINGDGSLFYPNGPENPSPSLPNPSIVPAFCGETILVNGKAWPYLEV EPRKYRFRVINASNTRTYNLSLDNDGEFIQIGSDGGLLPRSVKLNSFSL APAERYDIIIDFTAYEGQSIILANSEGCGGDANPETDANIMQFRVTKPL AQKDESRKPKYLASYPSVQNERIHNIRTLKLAGTQDEYGRPVLLLNNKR WHDPVTETPKAGTTEIWSIINPTRGTHPIHLHLVSFRVLDRRPFDIARY |

TABLE 5-continued

Sequences of SEQ ID NOS: 1-24.

| SEQ ID NO: | Name | Organism | Sequence |
|---|---|---|---|
| | | | QERGELSYTGPAVPPPPSEKGWKDTIQAHAGEVLRIAATFGPYSGRYVW<br>HCHILEHEDYDMMRPMDITDPHK |
| 20 | Seq 49<br>149S | Bacillus<br>vallismortis | MTLEKFVDALPIPETLKPVQQTKEKTYYEVTMEECAHKLHRDLPPTRLW<br>GYNCQFPGPTIEVNRNENVYVKWMNHLSSTHFLPVDHTIHRSDSQHEEP<br>EVKTVVHLGGVTPEDSDGYPEAWFTKDFEQTGPYFKREIYHYPNQQRG<br>ASLWYHDHAMALTRLNVYAGLIGAYLIHDPKEKRLKLPSGEYDVPLLIT<br>DRTINGDGSLFYPNGPENPSPSLPNPSIVPAFCGETILVNGKAWPYLEV<br>EPRKYRFRVINASNTRTYNLSLDNDGEFIQIGSDGGLLPRSVKLNSFSL<br>APAERYDIIIDFTAYEGQSIILANSEGCGGDANPETDANIMQFRVTKPL<br>AQKDESRKPKYLASYPSVQNERIHNIRTLKLAGTQDEYGRPVLLLNNKR<br>WHDPVTETPKAGTTEIWSIINPTRGTHPIHLHLVSFRVLDRRPFDIARY<br>QERGELSYTGPAVPPPPSEKGWKDTIQAHAGEVLRIAATFGPYSGRYVW<br>HCHILEHEDYDMMRPMDITDPHK |
| 21 | Seq 49<br>149C | Bacillus<br>vallismortis | MTLEKFVDALPIPETLKPVQQTKEKTYYEVTMEECAHKLHRDLPPTRLW<br>GYNCQFPGPTIEVNRNENVYVKWMNHLSSTHFLPVDHTIHRSDSQHEEP<br>EVKTVVHLGGVTPEDSDGYPEAWFTKDFEQTGPYFKREIYHYPNQQRG<br>ACLWYHDHAMALTRLNVYAGLIGAYLIHDPKEKRLKLPSGEYDVPLLIT<br>DRTINGDGSLFYPNGPENPSPSLPNPSIVPAFCGETILVNGKAWPYLEV<br>EPRKYRFRVINASNTRTYNLSLDNDGEFIQIGSDGGLLPRSVKLNSFSL<br>APAERYDIIIDFTAYEGQSIILANSEGCGGDANPETDANIMQFRVTKPL<br>AQKDESRKPKYLASYPSVQNERIHNIRTLKLAGTQDEYGRPVLLLNNKR<br>WHDPVTETPKAGTTEIWSIINPTRGTHPIHLHLVSFRVLDRRPFDIARY<br>QERGELSYTGPAVPPPPSEKGWKDTIQAHAGEVLRIAATFGPYSGRYVW<br>HCHILEHEDYDMMRPMDITDPHK |
| 22 | Seq 49<br>149D | Bacillus<br>vallismortis | MTLEKFVDALPIPETLKPVQQTKEKTYYEVTMEECAHKLHRDLPPTRLW<br>GYNCQFPGPTIEVNRNENVYVKWMNHLSSTHFLPVDHTIHRSDSQHEEP<br>EVKTVVHLGGVTPEDSDGYPEAWFTKDFEQTGPYFKREIYHYPNQQRG<br>ADLWYHDHAMALTRLNVYAGLIGAYLIHDPKEKRLKLPSGEYDVPLLIT<br>DRTINGDGSLFYPNGPENPSPSLPNPSIVPAFCGETILVNGKAWPYLEV<br>EPRKYRFRVINASNTRTYNLSLDNDGEFIQIGSDGGLLPRSVKLNSFSL<br>APAERYDIIIDFTAYEGQSIILANSEGCGGDANPETDANIMQFRVTKPL<br>AQKDESRKPKYLASYPSVQNERIHNIRTLKLAGTQDEYGRPVLLLNNKR<br>WHDPVTETPKAGTTEIWSIINPTRGTHPIHLHLVSFRVLDRRPFDIARY<br>QERGELSYTGPAVPPPPSEKGWKDTIQAHAGEVLRIAATFGPYSGRYVW<br>HCHILEHEDYDMMRPMDITDPHK |
| 23 | Seq 49<br>149N | Bacillus<br>vallismortis | MTLEKFVDALPIPETLKPVQQTKEKTYYEVTMEECAHKLHRDLPPTRLW<br>GYNCQFPGPTIEVNRNENVYVKWMNHLSSTHFLPVDHTIHRSDSQHEEP<br>EVKTVVHLGGVTPEDSDGYPEAWFTKDFEQTGPYFKREIYHYPNQQRG<br>ANLWYHDHAMALTRLNVYAGLIGAYLIHDPKEKRLKLPSGEYDVPLLIT<br>DRTINGDGSLFYPNGPENPSPSLPNPSIVPAFCGETILVNGKAWPYLEV<br>EPRKYRFRVINASNTRTYNLSLDNDGEFIQIGSDGGLLPRSVKLNSFSL<br>APAERYDIIIDFTAYEGQSIILANSEGCGGDANPETDANIMQFRVTKPL<br>AQKDESRKPKYLASYPSVQNERIHNIRTLKLAGTQDEYGRPVLLLNNKR<br>WHDPVTETPKAGTTEIWSIINPTRGTHPIHLHLVSFRVLDRRPFDIARY<br>QERGELSYTGPAVPPPPSEKGWKDTIQAHAGEVLRIAATFGPYSGRYVW<br>HCHILEHEDYDMMRPMDITDPHK |
| 24 | Seq 49<br>149V | Bacillus<br>vallismortis | MTLEKFVDALPIPETLKPVQQTKEKTYYEVTMEECAHKLHRDLPPTRLW<br>GYNCQFPGPTIEVNRNENVYVKWMNHLSSTHFLPVDHTIHRSDSQHEEP<br>EVKTVVHLGGVTPEDSDGYPEAWFTKDFEQTGPYFKREIYHYPNQQRG<br>AVLWYHDHAMALTRLNVYAGLIGAYLIHDPKEKRLKLPSGEYDVPLLIT<br>DRTINGDGSLFYPNGPENPSPSLPNPSIVPAFCGETILVNGKAWPYLEV<br>EPRKYRFRVINASNTRTYNLSLDNDGEFIQIGSDGGLLPRSVKLNSFSL<br>APAERYDIIIDFTAYEGQSIILANSEGCGGDANPETDANIMQFRVTKPL<br>AQKDESRKPKYLASYPSVQNERIHNIRTLKLAGTQDEYGRPVLLLNNKR<br>WHDPVTETPKAGTTEIWSIINPTRGTHPIHLHLVSFRVLDRRPFDIARY<br>QERGELSYTGPAVPPPPSEKGWKDTIQAHAGEVLRIAATFGPYSGRYVW<br>HCHILEHEDYDMMRPMDITDPHK |

REFERENCES

1. Martins L. O., C. M. Soares, M. M. Pereira, M. Teixeira, T. Costa, and G. H. Jones, et al. Molecular and biochemical characterization of a highly stable bacterial laccase that occurs as a structural component of the Bacillus subtilis endospore coat. J. Biol. Chem. 2002, 277:18849-59.

2. Bento I., L. O. Martins, G. Gato Lopes, M. Arménia Carrondo, and P. F. Lindley. Dioxygen reduction by multi-copper oxidases: a structural perspective. Dalton Trans 2005, 21:3507-13.

3. Brissos V., L. Pereira, F. D. Munteanu, A. Cavaco-Paulo, and L. O. Martins. Expression system of CotA-laccase for directed evolution and high-throughput screenings for the oxidation of high-redox potential dyes. Biotechnol. J. 2009, 4:558-63.

4. Suzuki T., K. Endo, M. Ito, H. Tsujibo, K. Miyamoto, and Y. Inamori. A thermostable laccase from *Streptomyces lavendulae* REN-7: purification, characterization, nucleotide sequence and expression. *Biosci. Biotechnol. Biochem.* 2003, 67:2167-75.
5. Kumar et al., "Combined sequence and structure analysis of the fungal laccase family," *Biotechnol. Bioeng.* 2003, 83:386-394.
6. Morozova et al., "Blue laccases," *Biochemistry* (Moscow), 2007, 72:1136-1150.
7. Cantarella et al., "Determination of laccase activity in mixed solvents: Comparison between two chromogens in a spectrophotometric assay," *Biotechnology and Bioengineering,* 2003, V. 82(4):395-398.
8. *Methods in Molecular Biology,* 2002, vol. 182, "In vitro mutagenesis protocols," eds. Jeff Braman, Humana Press.

The invention claimed is:

1. A polypeptide variant with laccase activity consisting of an amino acid sequence that is at least 90% identical to the amino acid sequence according to SEQ ID NO: 1, wherein the polypeptide comprises a small amino acid residue selected from the group consisting of threonine, proline, alanine, glycine, serine, cysteine, aspartic acid, asparagine and valine at an amino acid position corresponding to position 149 in SEQ ID NO: 1.

2. The polypeptide of claim 1, wherein the small amino acid residue is a threonine residue.

3. The polypeptide of claim 1, wherein the polypeptide comprises an amino acid sequence that is at least 94% identical to an amino acid sequence selected from the group consisting of SEQ ID NOS: 51-75 and SEQ ID NOS: 80-94.

4. The polypeptide of claim 1, wherein the polypeptide is an isolated polypeptide.

5. A composition comprising the polypeptide of claim 1.

6. A nucleic acid encoding the polypeptide of claim 1.

7. A vector comprising the nucleic acid of claim 6.

8. A composition comprising the nucleic acid of claim 6.

9. A recombinant host cell comprising a nucleic acid according to claim 6.

10. The recombinant host cell according to claim 9, wherein the host cell is selected from the group consisting of *Escherichia coli*, *Bacillus*, *Corynebacterium*, *Pseudomonas*, *Pichia pastoris*, *Saccharomyces cerevisiae*, *Yarrowia lipolytica*, filamentous fungi, yeast, and insect cells.

11. A method for producing a polypeptide variant with laccase activity, comprising the steps of:
    culturing a recombinant host cell according to claim 9 under conditions suitable for the production of the polypeptide, and
    recovering the polypeptide obtained, and
    optionally purifying said polypeptide.

12. A method of utilizing the polypeptide of claim 1, the method comprising,
    utilizing the polypeptide in an application selected from the group consisting of pulp delignification, degrading or decreasing the structural integrity of lignocellulosic material, textile dye bleaching, wastewater detoxification, xenobiotic detoxification, production of a sugar from a lignocellulosic material and recovering cellulose from a biomass.

13. A method of improving the yield of a polypeptide with laccase activity in a heterologous expression system, the method comprising,
    altering the amino acid sequence of the polypeptide at a position corresponding to position 149 in SEQ ID NO: 1 to a small amino acid residue selected from the group consisting of threonine, proline, alanine, glycine, serine, cysteine, aspartic acid, asparagine, and valine;
    wherein the polypeptide consists of an amino acid sequence that is at least 90% identical to the amino acid sequence according to SEQ ID NO: 1.

14. The method according to claim 13, wherein the polypeptide with laccase activity is a spore coat protein.

15. Method according to claim 13, wherein the small amino acid is a threonine residue.

16. A recombinant host cell comprising the vector of claim 7.

17. A recombinant host cell comprising the composition of claim 8.

18. A composition comprising the vector according of claim 7.

19. The method according to claim 14, wherein the spore coat protein is a spore coat protein from a *Bacillus* species.

20. The method according to claim 19, wherein the *Bacillus* species is *Bacillus subtilis*.

21. A method of utilizing the composition of claim 5, the method comprising, utilizing the composition in an application selected from the group consisting of pulp delignification, degrading or decreasing the structural integrity of lignocellulosic material, textile dye bleaching, wastewater detoxification, xenobiotic detoxification, production of a sugar from a lignocellulosic material, and recovering cellulose from a biomass.

* * * * *

UNITED STATES PATENT AND TRADEMARK OFFICE
CERTIFICATE OF CORRECTION

PATENT NO. : 9,896,667 B2
APPLICATION NO. : 15/303486
DATED : February 20, 2018
INVENTOR(S) : Klara Birikh It is certified that error appears in the above-identified patent and that said Letters Patent is hereby corrected as shown below:

In the Specification

Column 11,   Line 45,   change "(94%400% identity)."
to --(94%-100% identity).--

Signed and Sealed this
First Day of May, 2018

Andrei Iancu
*Director of the United States Patent and Trademark Office*

SEQUENCE LISTING

```
<160> NUMBER OF SEQ ID NOS: 139

<210> SEQ ID NO 1
<211> LENGTH: 513
<212> TYPE: PRT
<213> ORGANISM: Bacillus subtilis

<400> SEQUENCE: 1

Met Thr Leu Glu Lys Phe Val Asp Ala Leu Pro Ile Pro Asp Thr Leu
1               5                   10                  15

Lys Pro Val Gln Gln Thr Thr Glu Lys Thr Tyr Tyr Glu Val Thr Met
            20                  25                  30

Glu Glu Cys Ala His Gln Leu His Arg Asp Leu Pro Pro Thr Arg Leu
        35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Glu His
65                  70                  75                  80

Phe Leu Pro Ile Asp His Thr Ile His His Ser Asp Ser Gln His Glu
                85                  90                  95

Glu Pro Glu Val Lys Thr Val Val His Leu His Gly Gly Val Thr Pro
            100                 105                 110

Asp Asp Ser Asp Gly Tyr Pro Glu Ala Trp Phe Ser Lys Asp Phe Glu
        115                 120                 125

Gln Thr Gly Pro Tyr Phe Lys Arg Glu Val Tyr His Tyr Pro Asn Gln
    130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Gly Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Gly Pro Glu Asn Pro Ser Pro Ser Leu Pro Lys Pro Ser Ile
    210                 215                 220

Val Pro Ala Phe Cys Gly Asp Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Glu
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Tyr Asp Ile Ile Ile
    290                 295                 300

Asp Phe Thr Ala Tyr Glu Gly Glu Ser Ile Ile Leu Ala Asn Ser Glu
```

```
            305                 310                 315                 320
        Gly Cys Gly Gly Asp Ala Asn Pro Glu Thr Asp Ala Asn Ile Met Gln
                        325                 330                 335

Phe Arg Val Thr Lys Pro Leu Ala Gln Lys Asp Glu Ser Arg Lys Pro
                        340                 345                 350

Lys Tyr Leu Ala Ser Tyr Pro Ser Val Gln Asn Glu Arg Ile Gln Asn
                        355                 360                 365

Ile Arg Thr Leu Lys Leu Ala Gly Thr Gln Asp Glu Tyr Gly Arg Pro
                        370                 375                 380

Val Leu Leu Leu Asn Asn Lys Arg Trp His Asp Pro Val Thr Glu Ala
        385                 390                 395                 400

Pro Lys Ala Gly Thr Thr Glu Ile Trp Ser Ile Val Asn Pro Thr Gln
                        405                 410                 415

Gly Thr His Pro Ile His Leu His Leu Val Ser Phe Arg Val Leu Asp
                        420                 425                 430

Arg Arg Pro Phe Asp Ile Ala Arg Tyr Gln Glu Arg Gly Glu Leu Ser
                        435                 440                 445

Tyr Thr Gly Pro Ala Val Pro Pro Pro Ser Glu Lys Gly Trp Lys
                        450                 455                 460

Asp Thr Ile Gln Ala His Ala Gly Glu Val Leu Arg Ile Ala Val Thr
        465                 470                 475                 480

Phe Gly Pro Tyr Ser Gly Arg Tyr Val Trp His Cys His Ile Leu Glu
                        485                 490                 495

His Glu Asp Tyr Asp Met Met Arg Pro Met Asp Ile Thr Asp Pro His
                        500                 505                 510

Lys

<210> SEQ ID NO 2
<211> LENGTH: 539
<212> TYPE: PRT
<213> ORGANISM: Bacillus subtilis

<400> SEQUENCE: 2

Met Thr Leu Glu Lys Phe Val Asp Ala Leu Pro Ile Pro Asp Thr Leu
        1               5                   10                  15

Lys Pro Val Gln Gln Ser Lys Glu Lys Thr Tyr Tyr Glu Val Thr Met
                        20                  25                  30

Glu Glu Cys Thr His Gln Leu His Arg Asp Leu Pro Pro Thr Arg Leu
                        35                  40                  45

Trp Gly Tyr Asn Gly Leu Phe Pro Gly Pro Thr Ile Glu Val Lys Arg
        50                  55                  60

Asn Glu Asn Val Tyr Val Lys Trp Met Asn Asn Leu Pro Ser Thr His
        65                  70                  75                  80

Phe Leu Pro Ile Asp His Thr Ile His His Ser Asp Ser Gln His Glu
                        85                  90                  95

Glu Pro Glu Val Lys Thr Val His Leu His Gly Gly Val Thr Pro
                        100                 105                 110

Asp Asp Ser Asp Gly Tyr Pro Glu Ala Trp Phe Ser Lys Asp Phe Glu
                        115                 120                 125

Gln Thr Gly Pro Tyr Phe Lys Arg Glu Val Tyr His Tyr Pro Asn Gln
                        130                 135                 140

Gln Arg Gly Ala Ile Leu Trp Tyr His Asp His Ala Met Ala Leu Thr
        145                 150                 155                 160

Arg Leu Asn Val Tyr Ala Gly Leu Val Gly Ala Tyr Ile Ile His Asp
```

165                 170                 175
Pro Lys Glu Lys Arg Leu Lys Leu Pro Ser Glu Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Gly Pro Glu Asn Pro Ser Pro Ser Leu Pro Asn Pro Ser Ile
    210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
            245                 250                 255

Ala Ser Asn Thr Arg Thr Tyr Asn Leu Ser Leu Asp Asn Gly Gly Glu
        260                 265                 270

Phe Ile Gln Ile Gly Ser Asp Gly Gly Leu Leu Pro Arg Ser Val Lys
    275                 280                 285

Leu Thr Ser Phe Ser Leu Ala Pro Ala Glu Arg Tyr Asp Ile Ile Ile
290                 295                 300

Asp Phe Thr Ala Tyr Glu Gly Gln Ser Ile Ile Leu Ala Asn Ser Ala
305                 310                 315                 320

Gly Cys Gly Gly Asp Val Asn Pro Glu Thr Asp Ala Asn Ile Met Gln
            325                 330                 335

Phe Arg Val Thr Lys Pro Leu Ala Gln Lys Asp Glu Ser Arg Lys Pro
        340                 345                 350

Lys Tyr Leu Ala Ser Tyr Pro Ser Val Gln Asn Glu Arg Ile Gln Asn
    355                 360                 365

Ile Arg Thr Leu Lys Leu Ala Gly Thr Gln Asp Glu Tyr Gly Arg Pro
370                 375                 380

Val Leu Leu Leu Asn Asn Lys Arg Trp His Asp Pro Val Thr Glu Ala
385                 390                 395                 400

Pro Lys Ala Gly Thr Thr Glu Ile Trp Ser Ile Ile Asn Pro Thr Arg
            405                 410                 415

Gly Thr His Pro Ile His Leu His Leu Val Ser Phe Arg Val Ile Asp
        420                 425                 430

Arg Arg Pro Phe Asp Ile Ala His Tyr Gln Glu Ser Gly Ala Leu Ser
    435                 440                 445

Tyr Thr Gly Pro Ala Val Pro Pro Pro Ser Glu Lys Gly Trp Lys
450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
            485                 490                 495

His Glu Asp Tyr Asp Met Met Arg Pro Met Asp Ile Thr Asp Pro His
        500                 505                 510

Lys Ser Asp Pro Asn Ser Ser Ser Val Asp Lys Leu His Arg Thr Arg
    515                 520                 525

Ala Pro Pro Pro Pro Leu Arg Ser Gly Cys
    530                 535

<210> SEQ ID NO 3
<211> LENGTH: 513
<212> TYPE: PRT
<213> ORGANISM: Bacillus subtilis

<400> SEQUENCE: 3

```
Met Thr Leu Glu Lys Phe Val Asp Ala Leu Pro Ile Pro Asp Thr Leu
1               5                   10                  15

Lys Pro Val Gln Gln Thr Thr Glu Lys Thr Tyr Tyr Glu Val Thr Met
            20                  25                  30

Glu Glu Cys Ala His Gln Leu His Arg Asp Leu Pro Pro Thr Arg Leu
            35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Glu His
65                  70                  75                  80

Phe Leu Pro Ile Asp His Thr Ile His His Ser Asp Ser Gln His Glu
                85                  90                  95

Glu Pro Glu Val Lys Thr Val Val His Leu His Gly Gly Val Thr Pro
            100                 105                 110

Asp Asp Ser Asp Gly Tyr Pro Glu Ala Trp Phe Ser Lys Asp Phe Glu
            115                 120                 125

Gln Thr Gly Pro Tyr Phe Lys Arg Glu Val Tyr His Tyr Pro Asn Gln
    130                 135                 140

Gln Arg Gly Ala Thr Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Gly Glu Tyr Asp Val Pro
            180                 185                 190

Leu Leu Ile Thr Asp Arg Thr Ile Asn Glu Asp Gly Ser Leu Phe Tyr
            195                 200                 205

Pro Ser Gly Pro Glu Asn Pro Ser Pro Ser Leu Pro Lys Pro Ser Ile
    210                 215                 220

Val Pro Ala Phe Cys Gly Asp Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Glu
            260                 265                 270

Phe Ile Gln Ile Gly Ser Asp Gly Gly Leu Leu Pro Arg Ser Val Lys
            275                 280                 285

Leu Asn Ser Phe Ser Leu Ala Pro Ala Glu Arg Tyr Asp Ile Ile Ile
    290                 295                 300

Asp Phe Thr Ala Tyr Glu Gly Glu Ser Ile Ile Leu Ala Asn Ser Glu
305                 310                 315                 320

Gly Cys Gly Gly Asp Ala Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln Asn Glu Arg Ile Gln Asn
    355                 360                 365

Ile Arg Thr Leu Lys Leu Ala Gly Thr Gln Asp Glu Tyr Gly Arg Pro
    370                 375                 380

Val Leu Leu Leu Asn Asn Lys Arg Trp His Asp Pro Val Thr Glu Ala
385                 390                 395                 400

Pro Lys Ala Gly Thr Thr Glu Ile Trp Ser Ile Val Asn Pro Thr Gln
                405                 410                 415

Gly Thr His Pro Ile His Leu His Leu Val Ser Phe Arg Val Leu Asp
```

```
                    420                 425                 430
Arg Arg Pro Phe Asp Ile Ala Arg Tyr Gln Glu Arg Gly Glu Leu Ser
        435                 440                 445

Tyr Thr Gly Pro Ala Val Pro Pro Pro Ser Glu Lys Gly Trp Lys
450                 455                 460

Asp Thr Ile Gln Ala His Ala Gly Glu Val Leu Arg Ile Ala Val Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
                500                 505                 510

Lys

<210> SEQ ID NO 4
<211> LENGTH: 539
<212> TYPE: PRT
<213> ORGANISM: Bacillus subtilis

<400> SEQUENCE: 4

Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
            20                  25                  30

Glu Glu Cys Thr His Gln Leu His Arg Asp Leu Pro Pro Thr Arg Leu
        35                  40                  45

Trp Gly Tyr Asn Gly Leu Phe Pro Gly Pro Thr Ile Glu Val Lys Arg
50                  55                  60

Asn Glu Asn Val Tyr Val Lys Trp Met Asn Asn Leu Pro Ser Thr His
65                  70                  75                  80

Phe Leu Pro Ile Asp His Thr Ile His Ser Asp Ser Gln His Glu
                85                  90                  95

Glu Pro Glu Val Lys Thr Val Val His Leu His Gly Gly Val Thr Pro
            100                 105                 110

Asp Asp Ser Asp Gly Tyr Pro Glu Ala Trp Phe Ser Lys Asp Phe Glu
        115                 120                 125

Gln Thr Gly Pro Tyr Phe Lys Arg Glu Val Tyr His Tyr Pro Asn Gln
    130                 135                 140

Gln Arg Gly Ala Thr Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Glu Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Gly Pro Glu Asn Pro Ser Pro Ser Leu Pro Asn Pro Ser Ile
    210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Glu
            260                 265                 270

Phe Ile Gln Ile Gly Ser Asp Gly Gly Leu Leu Pro Arg Ser Val Lys
```

```
            275                 280                 285
Leu Thr Ser Phe Ser Leu Ala Pro Ala Glu Arg Tyr Asp Ile Ile Ile
290                 295                 300
Asp Phe Thr Ala Tyr Glu Gly Gln Ser Ile Ile Leu Ala Asn Ser Ala
305                 310                 315                 320
Gly Cys Gly Gly Asp Val Asn Pro Glu Thr Asp Ala Asn Ile Met Gln
                325                 330                 335
Phe Arg Val Thr Lys Pro Leu Ala Gln Lys Asp Glu Ser Arg Lys Pro
                340                 345                 350
Lys Tyr Leu Ala Ser Tyr Pro Ser Val Gln Asn Glu Arg Ile Gln Asn
                355                 360                 365
Ile Arg Thr Leu Lys Leu Ala Gly Thr Gln Asp Glu Tyr Gly Arg Pro
370                 375                 380
Val Leu Leu Leu Asn Asn Lys Arg Trp His Asp Pro Val Thr Glu Ala
385                 390                 395                 400
Pro Lys Ala Gly Thr Thr Glu Ile Trp Ser Ile Ile Asn Pro Thr Arg
                405                 410                 415
Gly Thr His Pro Ile His Leu His Leu Val Ser Phe Arg Val Ile Asp
                420                 425                 430
Arg Arg Pro Phe Asp Ile Ala His Tyr Gln Glu Ser Gly Ala Leu Ser
                435                 440                 445
Tyr Thr Gly Pro Ala Val Pro Pro Pro Ser Glu Lys Gly Trp Lys
                450                 455                 460
Asp Thr Ile Gln Ala His Ala Gly Glu Val Leu Arg Ile Ala Ala Thr
465                 470                 475                 480
Phe Gly Pro Tyr Ser Gly Arg Tyr Val Trp His Cys His Ile Leu Glu
                485                 490                 495
His Glu Asp Tyr Asp Met Met Arg Pro Met Asp Ile Thr Asp Pro His
                500                 505                 510
Lys Ser Asp Pro Asn Ser Ser Val Asp Lys Leu His Arg Thr Arg
                515                 520                 525
Ala Pro Pro Pro Pro Leu Arg Ser Gly Cys
    530                 535

<210> SEQ ID NO 5
<211> LENGTH: 512
<212> TYPE: PRT
<213> ORGANISM: Bacillus spec

<400> SEQUENCE: 5

Met Ala Leu Glu Lys Phe Ala Asp Glu Leu Pro Ile Ile Glu Thr Leu
1               5                   10                  15
Gln Pro Gln Lys Lys Ser Asp Gly Ser Thr Tyr Tyr Glu Val Thr Met
                20                  25                  30
Lys Glu Cys Phe His Lys Leu His Arg Asp Leu Pro Pro Thr Arg Leu
            35                  40                  45
Trp Gly Tyr Asn Gly Leu Phe Pro Gly Pro Thr Ile Asp Val Asn Lys
        50                  55                  60
Asp Glu Asn Val Tyr Ile Lys Trp Met Asn Asp Leu Pro Asp Lys His
65                  70                  75                  80
Phe Leu Pro Val Asp His Thr Ile His His Ser Glu Ser Gly His Gln
                85                  90                  95
Glu Pro Asp Val Lys Thr Val Val His Leu His Gly Gly Ala Thr Pro
                100                 105                 110
```

```
Pro Asp Ser Asp Gly Tyr Pro Glu Ala Trp Phe Thr Lys Asp Phe Lys
            115                 120                 125

Glu Thr Gly Pro Tyr Phe Glu Arg Glu Val Tyr His Tyr Pro Asn Lys
        130                 135                 140

Gln Arg Gly Ala Leu Leu Trp Tyr His Asp His Ala Met Ala Ile Thr
145                 150                 155                 160

Arg Leu Asn Val Tyr Ala Gly Leu Ala Gly Met Tyr Ile Ile Arg Glu
                165                 170                 175

Arg Lys Glu Lys Gln Leu Lys Leu Pro Ser Gly Glu Tyr Asp Val Pro
            180                 185                 190

Leu Met Ile Leu Asp Arg Thr Leu Asn Asp Asp Gly Ser Leu Ser Tyr
        195                 200                 205

Pro Ser Gly Pro Ala Asn Pro Ser Glu Thr Leu Pro Asp Pro Ser Ile
    210                 215                 220

Val Pro Phe Phe Cys Gly Asn Thr Ile Leu Val Asn Gly Lys Ala Trp
225                 230                 235                 240

Pro Tyr Met Glu Val Glu Pro Arg Thr Tyr Arg Phe Arg Ile Leu Asn
                245                 250                 255

Ala Ser Asn Thr Arg Thr Phe Ser Leu Ser Leu Asn Asn Gly Gly Lys
            260                 265                 270

Phe Ile Gln Ile Gly Ser Asp Gly Gly Leu Leu Pro Arg Ser Val Lys
        275                 280                 285

Thr Gln Ser Ile Ser Leu Ala Pro Ala Glu Arg Tyr Asp Val Leu Ile
    290                 295                 300

Asp Phe Ser Ala Phe Asp Gly Glu His Ile Ile Leu Thr Asn Gly Thr
305                 310                 315                 320

Gly Cys Gly Gly Asp Ala Asp Pro Asp Thr Asp Ala Asn Val Met Gln
                325                 330                 335

Phe Arg Val Thr Lys Pro Leu Lys Gly Ala Asp Thr Ser Arg Lys Pro
            340                 345                 350

Lys Tyr Leu Ser Thr Met Pro Asn Val Thr Ser Lys Arg Ile His Asn
        355                 360                 365

Ile Arg Met Leu Lys Leu Thr Asn Thr Gln Asp Lys Tyr Gly Arg Pro
    370                 375                 380

Val Leu Thr Leu Asn Asn Lys Arg Trp His Asp Pro Val Thr Glu Ala
385                 390                 395                 400

Pro Lys Leu Gly Thr Thr Glu Ile Trp Ser Ile Ile Asn Pro Met Gly
                405                 410                 415

Gly Thr His Pro Ile His Leu His Leu Val Ser Phe Gln Ile Leu Asp
            420                 425                 430

Arg Arg Pro Phe Asp Leu Glu Arg Tyr Asn Lys Phe Gly Asp Ile Val
        435                 440                 445

Tyr Thr Gly Pro Ala Val Pro Pro Pro Ser Glu Lys Gly Trp Lys
    450                 455                 460

Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
                485                 490                 495

His Glu Asp Tyr Asp Met Met Arg Pro Met Asp Val Thr Asp Lys Gln
            500                 505                 510

<210> SEQ ID NO 6
<211> LENGTH: 512
<212> TYPE: PRT
```

<213> ORGANISM: Bacillus spec

<400> SEQUENCE: 6

Met Ala Leu Glu Lys Phe Ala Asp Glu Leu Pro Ile Ile Glu Thr Leu
1               5                   10                  15

Gln Pro Gln Lys Lys Ser Asp Gly Ser Thr Tyr Tyr Val Thr Met
            20                  25                  30

Lys Glu Cys Phe His Lys Leu His Arg Asp Leu Pro Pro Thr Arg Leu
            35                  40                  45

Trp Gly Tyr Asn Gly Leu Phe Pro Gly Pro Thr Ile Asp Val Asn Lys
        50                  55                  60

Asp Glu Asn Val Tyr Ile Lys Trp Met Asn Asp Leu Pro Asp Lys His
65                  70                  75                  80

Phe Leu Pro Val Asp His Thr Ile His His Ser Glu Ser Gly His Gln
                85                  90                  95

Glu Pro Asp Val Lys Thr Val Val His Leu His Gly Gly Ala Thr Pro
            100                 105                 110

Pro Asp Ser Asp Gly Tyr Pro Glu Ala Trp Phe Thr Lys Asp Phe Lys
        115                 120                 125

Glu Thr Gly Pro Tyr Phe Glu Arg Glu Val Tyr His Tyr Pro Asn Lys
    130                 135                 140

Gln Arg Gly Ala Thr Leu Trp Tyr His Asp His Ala Met Ala Ile Thr
145                 150                 155                 160

Arg Leu Asn Val Tyr Ala Gly Leu Ala Gly Met Tyr Ile Ile Arg Glu
                165                 170                 175

Arg Lys Glu Lys Gln Leu Lys Leu Pro Ser Gly Glu Tyr Asp Val Pro
            180                 185                 190

Leu Met Ile Leu Asp Arg Thr Leu Asn Asp Asp Gly Ser Leu Ser Tyr
        195                 200                 205

Pro Ser Gly Pro Ala Asn Pro Ser Glu Thr Leu Pro Asp Pro Ser Ile
    210                 215                 220

Val Pro Phe Phe Cys Gly Asn Thr Ile Leu Val Asn Gly Lys Ala Trp
225                 230                 235                 240

Pro Tyr Met Glu Val Glu Pro Arg Thr Tyr Arg Phe Arg Ile Leu Asn
                245                 250                 255

Ala Ser Asn Thr Arg Thr Phe Ser Leu Ser Leu Asn Asn Gly Gly Lys
            260                 265                 270

Phe Ile Gln Ile Gly Ser Asp Gly Gly Leu Leu Pro Arg Ser Val Lys
        275                 280                 285

Thr Gln Ser Ile Ser Leu Ala Pro Ala Glu Arg Tyr Asp Val Leu Ile
    290                 295                 300

Asp Phe Ser Ala Phe Asp Gly Glu His Ile Ile Leu Thr Asn Gly Thr
305                 310                 315                 320

Gly Cys Gly Gly Asp Ala Asp Pro Asp Thr Asp Ala Asn Val Met Gln
                325                 330                 335

Phe Arg Val Thr Lys Pro Leu Lys Gly Ala Asp Thr Ser Arg Lys Pro
            340                 345                 350

Lys Tyr Leu Ser Thr Met Pro Asn Val Thr Ser Lys Arg Ile His Asn
        355                 360                 365

Ile Arg Met Leu Lys Leu Thr Asn Thr Gln Asp Lys Tyr Gly Arg Pro
    370                 375                 380

Val Leu Thr Leu Asn Asn Lys Arg Trp His Asp Pro Val Thr Glu Ala
385                 390                 395                 400

```
Pro Lys Leu Gly Thr Thr Glu Ile Trp Ser Ile Ile Asn Pro Met Gly
                405                 410                 415
Gly Thr His Pro Ile His Leu His Leu Val Ser Phe Gln Ile Leu Asp
            420                 425                 430
Arg Arg Pro Phe Asp Leu Glu Arg Tyr Asn Lys Phe Gly Asp Ile Val
        435                 440                 445
Tyr Thr Gly Pro Ala Val Pro Pro Pro Ser Glu Lys Gly Trp Lys
    450                 455                 460
Asp Thr Val Gln Ala His Ser Gly Glu Val Arg Ile Ala Ala Thr
465                 470                 475                 480
Phe Ala Pro Tyr Ser Gly Arg Tyr Val Trp His Cys His Ile Leu Glu
                485                 490                 495
His Glu Asp Tyr Asp Met Met Arg Pro Met Asp Val Thr Asp Lys Gln
                500                 505                 510

<210> SEQ ID NO 7
<211> LENGTH: 512
<212> TYPE: PRT
<213> ORGANISM: Bacillus spec

<400> SEQUENCE: 7

Met Ala Leu Glu Lys Phe Ala Asp Glu Leu Pro Ile Ile Glu Thr Leu
1               5                   10                  15
Gln Pro Gln Lys Lys Ser Asp Gly Ser Thr Tyr Tyr Glu Val Thr Met
            20                  25                  30
Lys Glu Cys Phe His Lys Leu His Arg Asp Leu Pro Pro Thr Arg Leu
        35                  40                  45
Trp Gly Tyr Asn Gly Leu Phe Pro Gly Pro Thr Ile Asp Val Asn Lys
    50                  55                  60
Asp Glu Asn Val Tyr Ile Lys Trp Met Asn Asp Leu Pro Asp Lys His
65                  70                  75                  80
Phe Leu Pro Val Asp His Thr Ile His His Ser Glu Ser Gly His Gln
                85                  90                  95
Glu Pro Asp Val Lys Thr Val Val His Leu His Gly Gly Ala Thr Pro
                100                 105                 110
Pro Asp Ser Asp Gly Tyr Pro Glu Ala Trp Phe Thr Lys Asp Phe Lys
            115                 120                 125
Glu Thr Gly Pro Tyr Phe Glu Arg Glu Val Tyr His Tyr Pro Asn Lys
        130                 135                 140
Gln Arg Gly Ala Pro Leu Trp Tyr His Asp His Ala Met Ala Ile Thr
145                 150                 155                 160
Arg Leu Asn Val Tyr Ala Gly Leu Ala Gly Met Tyr Ile Ile Arg Glu
                165                 170                 175
Arg Lys Glu Lys Gln Leu Lys Leu Pro Ser Gly Glu Tyr Asp Val Pro
                180                 185                 190
Leu Met Ile Leu Asp Arg Thr Leu Asn Asp Asp Gly Ser Leu Ser Tyr
            195                 200                 205
Pro Ser Gly Pro Ala Asn Pro Ser Glu Thr Leu Pro Asp Pro Ser Ile
        210                 215                 220
Val Pro Phe Phe Cys Gly Asn Thr Ile Leu Val Asn Gly Lys Ala Trp
225                 230                 235                 240
Pro Tyr Met Glu Val Glu Pro Arg Thr Tyr Arg Phe Arg Ile Leu Asn
                245                 250                 255
Ala Ser Asn Thr Arg Thr Phe Ser Leu Ser Leu Asn Asn Gly Gly Lys
                260                 265                 270
```

Phe Ile Gln Ile Gly Ser Asp Gly Gly Leu Leu Pro Arg Ser Val Lys
            275                 280                 285

Thr Gln Ser Ile Ser Leu Ala Pro Ala Glu Arg Tyr Asp Val Leu Ile
        290                 295                 300

Asp Phe Ser Ala Phe Asp Gly Glu His Ile Ile Leu Thr Asn Gly Thr
305                 310                 315                 320

Gly Cys Gly Gly Asp Ala Asp Pro Asp Thr Asp Ala Asn Val Met Gln
                325                 330                 335

Phe Arg Val Thr Lys Pro Leu Lys Gly Ala Asp Thr Ser Arg Lys Pro
            340                 345                 350

Lys Tyr Leu Ser Thr Met Pro Asn Val Thr Ser Lys Arg Ile His Asn
        355                 360                 365

Ile Arg Met Leu Lys Leu Thr Asn Thr Gln Asp Lys Tyr Gly Arg Pro
370                 375                 380

Val Leu Thr Leu Asn Asn Lys Arg Trp His Asp Pro Val Thr Glu Ala
385                 390                 395                 400

Pro Lys Leu Gly Thr Thr Glu Ile Trp Ser Ile Ile Asn Pro Met Gly
            405                 410                 415

Gly Thr His Pro Ile His Leu His Leu Val Ser Phe Gln Ile Leu Asp
        420                 425                 430

Arg Arg Pro Phe Asp Leu Glu Arg Tyr Asn Lys Phe Gly Asp Ile Val
            435                 440                 445

Tyr Thr Gly Pro Ala Val Pro Pro Pro Ser Glu Lys Gly Trp Lys
        450                 455                 460

Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
            485                 490                 495

His Glu Asp Tyr Asp Met Met Arg Pro Met Asp Val Thr Asp Lys Gln
        500                 505                 510

<210> SEQ ID NO 8
<211> LENGTH: 512
<212> TYPE: PRT
<213> ORGANISM: Bacillus spec

<400> SEQUENCE: 8

Met Ala Leu Glu Lys Phe Ala Asp Glu Leu Pro Ile Ile Glu Thr Leu
1               5                   10                  15

Gln Pro Gln Lys Lys Ser Asp Gly Ser Thr Tyr Tyr Glu Val Thr Met
            20                  25                  30

Lys Glu Cys Phe His Lys Leu His Arg Asp Leu Pro Pro Thr Arg Leu
        35                  40                  45

Trp Gly Tyr Asn Gly Leu Phe Pro Gly Pro Thr Ile Asp Val Asn Lys
    50                  55                  60

Asp Glu Asn Val Tyr Ile Lys Trp Met Asn Asp Leu Pro Asp Lys His
65                  70                  75                  80

Phe Leu Pro Val Asp His Thr Ile His His Ser Glu Ser Gly His Gln
            85                  90                  95

Glu Pro Asp Val Lys Thr Val Val His Leu His Gly Gly Ala Thr Pro
        100                 105                 110

Pro Asp Ser Asp Gly Tyr Pro Glu Ala Trp Phe Thr Lys Asp Phe Lys
    115                 120                 125

Glu Thr Gly Pro Tyr Phe Glu Arg Glu Val Tyr His Tyr Pro Asn Lys

```
                130             135             140
Gln Arg Gly Ala Ala Leu Trp Tyr His Asp His Ala Met Ala Ile Thr
145                 150                 155                 160

Arg Leu Asn Val Tyr Ala Gly Leu Ala Gly Met Tyr Ile Ile Arg Glu
                165                 170                 175

Arg Lys Glu Lys Gln Leu Lys Leu Pro Ser Gly Glu Tyr Asp Val Pro
            180                 185                 190

Leu Met Ile Leu Asp Arg Thr Leu Asn Asp Asp Gly Ser Leu Ser Tyr
                195                 200                 205

Pro Ser Gly Pro Ala Asn Pro Ser Glu Thr Leu Pro Asp Pro Ser Ile
210                 215                 220

Val Pro Phe Phe Cys Gly Asn Thr Ile Leu Val Asn Gly Lys Ala Trp
225                 230                 235                 240

Pro Tyr Met Glu Val Glu Pro Arg Thr Tyr Arg Phe Arg Ile Leu Asn
                245                 250                 255

Ala Ser Asn Thr Arg Thr Phe Ser Leu Ser Leu Asn Asn Gly Gly Lys
                260                 265                 270

Phe Ile Gln Ile Gly Ser Asp Gly Gly Leu Leu Pro Arg Ser Val Lys
            275                 280                 285

Thr Gln Ser Ile Ser Leu Ala Pro Ala Glu Arg Tyr Asp Val Leu Ile
290                 295                 300

Asp Phe Ser Ala Phe Asp Gly Glu His Ile Ile Leu Thr Asn Gly Thr
305                 310                 315                 320

Gly Cys Gly Gly Asp Ala Asp Pro Asp Thr Asp Ala Asn Val Met Gln
                325                 330                 335

Phe Arg Val Thr Lys Pro Leu Lys Gly Ala Asp Thr Ser Arg Lys Pro
                340                 345                 350

Lys Tyr Leu Ser Thr Met Pro Asn Val Thr Ser Lys Arg Ile His Asn
            355                 360                 365

Ile Arg Met Leu Lys Leu Thr Asn Thr Gln Asp Lys Tyr Gly Arg Pro
370                 375                 380

Val Leu Thr Leu Asn Asn Lys Arg Trp His Asp Pro Val Thr Glu Ala
385                 390                 395                 400

Pro Lys Leu Gly Thr Thr Glu Ile Trp Ser Ile Ile Asn Pro Met Gly
                405                 410                 415

Gly Thr His Pro Ile His Leu His Leu Val Ser Phe Gln Ile Leu Asp
                420                 425                 430

Arg Arg Pro Phe Asp Leu Glu Arg Tyr Asn Lys Phe Gly Asp Ile Val
            435                 440                 445

Tyr Thr Gly Pro Ala Val Pro Pro Pro Ser Glu Lys Gly Trp Lys
            450                 455                 460

Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
                485                 490                 495

His Glu Asp Tyr Asp Met Met Arg Pro Met Asp Val Thr Asp Lys Gln
                500                 505                 510

<210> SEQ ID NO 9
<211> LENGTH: 512
<212> TYPE: PRT
<213> ORGANISM: Bacillus spec

<400> SEQUENCE: 9
```

```
Met Ala Leu Glu Lys Phe Ala Asp Glu Leu Pro Ile Ile Glu Thr Leu
 1               5                  10                  15
Gln Pro Gln Lys Lys Ser Asp Gly Ser Thr Tyr Tyr Glu Val Thr Met
            20                  25                  30
Lys Glu Cys Phe His Lys Leu His Arg Asp Leu Pro Pro Thr Arg Leu
            35                  40                  45
Trp Gly Tyr Asn Gly Leu Phe Pro Gly Pro Thr Ile Asp Val Asn Lys
 50                      55                  60
Asp Glu Asn Val Tyr Ile Lys Trp Met Asn Asp Leu Pro Asp Lys His
 65                  70                  75                  80
Phe Leu Pro Val Asp His Thr Ile His His Ser Glu Ser Gly His Gln
                 85                  90                  95
Glu Pro Asp Val Lys Thr Val Val His Leu His Gly Gly Ala Thr Pro
             100                 105                 110
Pro Asp Ser Asp Gly Tyr Pro Glu Ala Trp Phe Thr Lys Asp Phe Lys
             115                 120                 125
Glu Thr Gly Pro Tyr Phe Glu Arg Glu Val Tyr His Tyr Pro Asn Lys
             130                 135                 140
Gln Arg Gly Ala Gly Leu Trp Tyr His Asp His Ala Met Ala Ile Thr
145                 150                 155                 160
Arg Leu Asn Val Tyr Ala Gly Leu Ala Gly Met Tyr Ile Ile Arg Glu
                 165                 170                 175
Arg Lys Glu Lys Gln Leu Lys Leu Pro Ser Gly Glu Tyr Asp Val Pro
             180                 185                 190
Leu Met Ile Leu Asp Arg Thr Leu Asn Asp Asp Gly Ser Leu Ser Tyr
             195                 200                 205
Pro Ser Gly Pro Ala Asn Pro Ser Glu Thr Leu Pro Asp Pro Ser Ile
             210                 215                 220
Val Pro Phe Phe Cys Gly Asn Thr Ile Leu Val Asn Gly Lys Ala Trp
225                 230                 235                 240
Pro Tyr Met Glu Val Glu Pro Arg Thr Tyr Arg Phe Arg Ile Leu Asn
                 245                 250                 255
Ala Ser Asn Thr Arg Thr Phe Ser Leu Ser Leu Asn Asn Gly Gly Lys
             260                 265                 270
Phe Ile Gln Ile Gly Ser Asp Gly Gly Leu Leu Pro Arg Ser Val Lys
             275                 280                 285
Thr Gln Ser Ile Ser Leu Ala Pro Ala Glu Arg Tyr Asp Val Leu Ile
             290                 295                 300
Asp Phe Ser Ala Phe Asp Gly Glu His Ile Ile Leu Thr Asn Gly Thr
305                 310                 315                 320
Gly Cys Gly Gly Asp Ala Asp Pro Asp Thr Asp Ala Asn Val Met Gln
             325                 330                 335
Phe Arg Val Thr Lys Pro Leu Lys Gly Ala Asp Thr Ser Arg Lys Pro
             340                 345                 350
Lys Tyr Leu Ser Thr Met Pro Asn Val Thr Ser Lys Arg Ile His Asn
             355                 360                 365
Ile Arg Met Leu Lys Leu Thr Asn Thr Gln Asp Lys Tyr Gly Arg Pro
             370                 375                 380
Val Leu Thr Leu Asn Asn Lys Arg Trp His Asp Pro Val Thr Glu Ala
385                 390                 395                 400
Pro Lys Leu Gly Thr Thr Glu Ile Trp Ser Ile Ile Asn Pro Met Gly
                 405                 410                 415
Gly Thr His Pro Ile His Leu His Leu Val Ser Phe Gln Ile Leu Asp
```

```
            420                 425                 430
Arg Arg Pro Phe Asp Leu Glu Arg Tyr Asn Lys Phe Gly Asp Ile Val
        435                 440                 445

Tyr Thr Gly Pro Ala Val Pro Pro Pro Ser Glu Lys Gly Trp Lys
    450                 455                 460

Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
                485                 490                 495

His Glu Asp Tyr Asp Met Met Arg Pro Met Asp Val Thr Asp Lys Gln
                500                 505                 510

<210> SEQ ID NO 10
<211> LENGTH: 512
<212> TYPE: PRT
<213> ORGANISM: Bacillus spec

<400> SEQUENCE: 10

Met Ala Leu Glu Lys Phe Ala Asp Glu Leu Pro Ile Ile Glu Thr Leu
1               5                   10                  15

Gln Pro Gln Lys Lys Ser Asp Gly Ser Thr Tyr Tyr Glu Val Thr Met
            20                  25                  30

Lys Glu Cys Phe His Lys Leu His Arg Asp Leu Pro Pro Thr Arg Leu
        35                  40                  45

Trp Gly Tyr Asn Gly Leu Phe Pro Gly Pro Thr Ile Asp Val Asn Lys
    50                  55                  60

Asp Glu Asn Val Tyr Ile Lys Trp Met Asn Asp Leu Pro Asp Lys His
65                  70                  75                  80

Phe Leu Pro Val Asp His Thr Ile His His Ser Glu Ser Gly His Gln
                85                  90                  95

Glu Pro Asp Val Lys Thr Val Val His Leu His Gly Gly Ala Thr Pro
            100                 105                 110

Pro Asp Ser Asp Gly Tyr Pro Glu Ala Trp Phe Thr Lys Asp Phe Lys
        115                 120                 125

Glu Thr Gly Pro Tyr Phe Glu Arg Glu Val Tyr His Tyr Pro Asn Lys
    130                 135                 140

Gln Arg Gly Ala Ser Leu Trp Tyr His Asp His Ala Met Ala Ile Thr
145                 150                 155                 160

Arg Leu Asn Val Tyr Ala Gly Leu Ala Gly Met Tyr Ile Ile Arg Glu
                165                 170                 175

Arg Lys Glu Lys Gln Leu Lys Leu Pro Ser Gly Glu Tyr Asp Val Pro
            180                 185                 190

Leu Met Ile Leu Asp Arg Thr Leu Asn Asp Asp Gly Ser Leu Ser Tyr
        195                 200                 205

Pro Ser Gly Pro Ala Asn Pro Ser Glu Thr Leu Pro Asp Pro Ser Ile
    210                 215                 220

Val Pro Phe Phe Cys Gly Asn Thr Ile Leu Val Asn Gly Lys Ala Trp
225                 230                 235                 240

Pro Tyr Met Glu Val Glu Pro Arg Thr Tyr Arg Phe Arg Ile Leu Asn
                245                 250                 255

Ala Ser Asn Thr Arg Thr Phe Ser Leu Ser Leu Asn Asn Gly Gly Lys
            260                 265                 270

Phe Ile Gln Ile Gly Ser Asp Gly Gly Leu Leu Pro Arg Ser Val Lys
        275                 280                 285
```

```
Thr Gln Ser Ile Ser Leu Ala Pro Ala Glu Arg Tyr Asp Val Leu Ile
    290                 295                 300

Asp Phe Ser Ala Phe Asp Gly Glu His Ile Ile Leu Thr Asn Gly Thr
305                 310                 315                 320

Gly Cys Gly Gly Asp Ala Asp Pro Asp Thr Asp Ala Asn Val Met Gln
                325                 330                 335

Phe Arg Val Thr Lys Pro Leu Lys Gly Ala Asp Thr Ser Arg Lys Pro
            340                 345                 350

Lys Tyr Leu Ser Thr Met Pro Asn Val Thr Ser Lys Arg Ile His Asn
        355                 360                 365

Ile Arg Met Leu Lys Leu Thr Asn Thr Gln Asp Lys Tyr Gly Arg Pro
370                 375                 380

Val Leu Thr Leu Asn Asn Lys Arg Trp His Asp Pro Val Thr Glu Ala
385                 390                 395                 400

Pro Lys Leu Gly Thr Thr Glu Ile Trp Ser Ile Ile Asn Pro Met Gly
                405                 410                 415

Gly Thr His Pro Ile His Leu His Leu Val Ser Phe Gln Ile Leu Asp
            420                 425                 430

Arg Arg Pro Phe Asp Leu Glu Arg Tyr Asn Lys Phe Gly Asp Ile Val
        435                 440                 445

Tyr Thr Gly Pro Ala Val Pro Pro Pro Ser Glu Lys Gly Trp Lys
    450                 455                 460

Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
                485                 490                 495

His Glu Asp Tyr Asp Met Met Arg Pro Met Asp Val Thr Asp Lys Gln
            500                 505                 510

<210> SEQ ID NO 11
<211> LENGTH: 512
<212> TYPE: PRT
<213> ORGANISM: Bacillus spec

<400> SEQUENCE: 11

Met Ala Leu Glu Lys Phe Ala Asp Glu Leu Pro Ile Ile Glu Thr Leu
1               5                   10                  15

Gln Pro Gln Lys Lys Ser Asp Gly Ser Thr Tyr Tyr Glu Val Thr Met
            20                  25                  30

Lys Glu Cys Phe His Lys Leu His Arg Asp Leu Pro Pro Thr Arg Leu
        35                  40                  45

Trp Gly Tyr Asn Gly Leu Phe Pro Gly Pro Thr Ile Asp Val Asn Lys
    50                  55                  60

Asp Glu Asn Val Tyr Ile Lys Trp Met Asn Asp Leu Pro Asp Lys His
65                  70                  75                  80

Phe Leu Pro Val Asp His Thr Ile His His Ser Glu Ser Gly His Gln
                85                  90                  95

Glu Pro Asp Val Lys Thr Val Val His Leu His Gly Gly Ala Thr Pro
            100                 105                 110

Pro Asp Ser Asp Gly Tyr Pro Glu Ala Trp Phe Thr Lys Asp Phe Lys
        115                 120                 125

Glu Thr Gly Pro Tyr Phe Glu Arg Glu Val Tyr His Tyr Pro Asn Lys
    130                 135                 140

Gln Arg Gly Ala Cys Leu Trp Tyr His Asp His Ala Met Ala Ile Thr
145                 150                 155                 160
```

```
Arg Leu Asn Val Tyr Ala Gly Leu Ala Gly Met Tyr Ile Ile Arg Glu
            165                 170                 175
Arg Lys Glu Lys Gln Leu Lys Leu Pro Ser Gly Glu Tyr Asp Val Pro
        180                 185                 190
Leu Met Ile Leu Asp Arg Thr Leu Asn Asp Asp Gly Ser Leu Ser Tyr
    195                 200                 205
Pro Ser Gly Pro Ala Asn Pro Ser Glu Thr Leu Pro Asp Pro Ser Ile
210                 215                 220
Val Pro Phe Phe Cys Gly Asn Thr Ile Leu Val Asn Gly Lys Ala Trp
225                 230                 235                 240
Pro Tyr Met Glu Val Glu Pro Arg Thr Tyr Arg Phe Arg Ile Leu Asn
            245                 250                 255
Ala Ser Asn Thr Arg Thr Phe Ser Leu Ser Leu Asn Asn Gly Gly Lys
        260                 265                 270
Phe Ile Gln Ile Gly Ser Asp Gly Gly Leu Leu Pro Arg Ser Val Lys
    275                 280                 285
Thr Gln Ser Ile Ser Leu Ala Pro Ala Glu Arg Tyr Asp Val Leu Ile
290                 295                 300
Asp Phe Ser Ala Phe Asp Gly Glu His Ile Ile Leu Thr Asn Gly Thr
305                 310                 315                 320
Gly Cys Gly Gly Asp Ala Asp Pro Asp Thr Asp Ala Asn Val Met Gln
            325                 330                 335
Phe Arg Val Thr Lys Pro Leu Lys Gly Ala Asp Thr Ser Arg Lys Pro
        340                 345                 350
Lys Tyr Leu Ser Thr Met Pro Asn Val Thr Ser Lys Arg Ile His Asn
    355                 360                 365
Ile Arg Met Leu Lys Leu Thr Asn Thr Gln Asp Lys Tyr Gly Arg Pro
370                 375                 380
Val Leu Thr Leu Asn Asn Lys Arg Trp His Asp Pro Val Thr Glu Ala
385                 390                 395                 400
Pro Lys Leu Gly Thr Thr Glu Ile Trp Ser Ile Ile Asn Pro Met Gly
            405                 410                 415
Gly Thr His Pro Ile His Leu His Leu Val Ser Phe Gln Ile Leu Asp
        420                 425                 430
Arg Arg Pro Phe Asp Leu Glu Arg Tyr Asn Lys Phe Gly Asp Ile Val
    435                 440                 445
Tyr Thr Gly Pro Ala Val Pro Pro Pro Ser Glu Lys Gly Trp Lys
450                 455                 460
Asp Thr Val Gln Ala His Ser Gly Glu Val Ile Arg Ile Ala Ala Thr
465                 470                 475                 480
Phe Ala Pro Tyr Ser Gly Arg Tyr Val Trp His Cys His Ile Leu Glu
            485                 490                 495
His Glu Asp Tyr Asp Met Met Arg Pro Met Asp Val Thr Asp Lys Gln
        500                 505                 510

<210> SEQ ID NO 12
<211> LENGTH: 512
<212> TYPE: PRT
<213> ORGANISM: Bacillus spec

<400> SEQUENCE: 12

Met Ala Leu Glu Lys Phe Ala Asp Glu Leu Pro Ile Ile Glu Thr Leu
1               5                   10                  15
Gln Pro Gln Lys Lys Ser Asp Gly Ser Thr Tyr Tyr Glu Val Thr Met
```

-continued

```
             20                  25                  30
Lys Glu Cys Phe His Lys Leu His Arg Asp Leu Pro Pro Thr Arg Leu
             35                  40                  45

Trp Gly Tyr Asn Gly Leu Phe Pro Gly Pro Thr Ile Asp Val Asn Lys
 50                  55                  60

Asp Glu Asn Val Tyr Ile Lys Trp Met Asn Asp Leu Pro Asp Lys His
 65                  70                  75                  80

Phe Leu Pro Val Asp His Thr Ile His His Ser Glu Ser Gly His Gln
                     85                  90                  95

Glu Pro Asp Val Lys Thr Val Val His Leu His Gly Gly Ala Thr Pro
                    100                 105                 110

Pro Asp Ser Asp Gly Tyr Pro Glu Ala Trp Phe Thr Lys Asp Phe Lys
                    115                 120                 125

Glu Thr Gly Pro Tyr Phe Glu Arg Glu Val Tyr His Tyr Pro Asn Lys
                    130                 135                 140

Gln Arg Gly Ala Asp Leu Trp Tyr His Asp His Ala Met Ala Ile Thr
145                 150                 155                 160

Arg Leu Asn Val Tyr Ala Gly Leu Ala Gly Met Tyr Ile Ile Arg Glu
                    165                 170                 175

Arg Lys Glu Lys Gln Leu Lys Leu Pro Ser Gly Glu Tyr Asp Val Pro
                    180                 185                 190

Leu Met Ile Leu Asp Arg Thr Leu Asn Asp Asp Gly Ser Leu Ser Tyr
                    195                 200                 205

Pro Ser Gly Pro Ala Asn Pro Ser Glu Thr Leu Pro Asp Pro Ser Ile
                    210                 215                 220

Val Pro Phe Phe Cys Gly Asn Thr Ile Leu Val Asn Gly Lys Ala Trp
225                 230                 235                 240

Pro Tyr Met Glu Val Glu Pro Arg Thr Tyr Arg Phe Arg Ile Leu Asn
                    245                 250                 255

Ala Ser Asn Thr Arg Thr Phe Ser Leu Ser Leu Asn Asn Gly Gly Lys
                    260                 265                 270

Phe Ile Gln Ile Gly Ser Asp Gly Gly Leu Leu Pro Arg Ser Val Lys
                    275                 280                 285

Thr Gln Ser Ile Ser Leu Ala Pro Ala Glu Arg Tyr Asp Val Leu Ile
                    290                 295                 300

Asp Phe Ser Ala Phe Asp Gly Glu His Ile Ile Leu Thr Asn Gly Thr
305                 310                 315                 320

Gly Cys Gly Gly Asp Ala Asp Pro Asp Thr Asp Ala Asn Val Met Gln
                    325                 330                 335

Phe Arg Val Thr Lys Pro Leu Lys Gly Ala Asp Thr Ser Arg Lys Pro
                    340                 345                 350

Lys Tyr Leu Ser Thr Met Pro Asn Val Thr Ser Lys Arg Ile His Asn
                    355                 360                 365

Ile Arg Met Leu Lys Leu Thr Asn Thr Gln Asp Lys Tyr Gly Arg Pro
                    370                 375                 380

Val Leu Thr Leu Asn Asn Lys Arg Trp His Asp Pro Val Thr Glu Ala
385                 390                 395                 400

Pro Lys Leu Gly Thr Thr Glu Ile Trp Ser Ile Asn Pro Met Gly
                    405                 410                 415

Gly Thr His Pro Ile His Leu His Leu Val Ser Phe Gln Ile Leu Asp
                    420                 425                 430

Arg Arg Pro Phe Asp Leu Glu Arg Tyr Asn Lys Phe Gly Asp Ile Val
                    435                 440                 445
```

```
Tyr Thr Gly Pro Ala Val Pro Pro Pro Ser Glu Lys Gly Trp Lys
        450                 455                 460

Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
                485                 490                 495

His Glu Asp Tyr Asp Met Met Arg Pro Met Asp Val Thr Asp Lys Gln
                500                 505                 510

<210> SEQ ID NO 13
<211> LENGTH: 512
<212> TYPE: PRT
<213> ORGANISM: Bacillus spec

<400> SEQUENCE: 13

Met Ala Leu Glu Lys Phe Ala Asp Glu Leu Pro Ile Ile Glu Thr Leu
1               5                   10                  15

Gln Pro Gln Lys Lys Ser Asp Gly Ser Thr Tyr Tyr Glu Val Thr Met
                20                  25                  30

Lys Glu Cys Phe His Lys Leu His Arg Asp Leu Pro Pro Thr Arg Leu
            35                  40                  45

Trp Gly Tyr Asn Gly Leu Phe Pro Gly Pro Thr Ile Asp Val Asn Lys
        50                  55                  60

Asp Glu Asn Val Tyr Ile Lys Trp Met Asn Asp Leu Pro Asp Lys His
65                  70                  75                  80

Phe Leu Pro Val Asp His Thr Ile His His Ser Glu Ser Gly His Gln
                85                  90                  95

Glu Pro Asp Val Lys Thr Val Val His Leu His Gly Gly Ala Thr Pro
            100                 105                 110

Pro Asp Ser Asp Gly Tyr Pro Glu Ala Trp Phe Thr Lys Asp Phe Lys
        115                 120                 125

Glu Thr Gly Pro Tyr Phe Glu Arg Glu Val Tyr His Tyr Pro Asn Lys
130                 135                 140

Gln Arg Gly Ala Asn Leu Trp Tyr His Asp His Ala Met Ala Ile Thr
145                 150                 155                 160

Arg Leu Asn Val Tyr Ala Gly Leu Ala Gly Met Tyr Ile Ile Arg Glu
                165                 170                 175

Arg Lys Glu Lys Gln Leu Lys Leu Pro Ser Gly Glu Tyr Asp Val Pro
            180                 185                 190

Leu Met Ile Leu Asp Arg Thr Leu Asn Asp Asp Gly Ser Leu Ser Tyr
        195                 200                 205

Pro Ser Gly Pro Ala Asn Pro Ser Glu Thr Leu Pro Asp Pro Ser Ile
210                 215                 220

Val Pro Phe Phe Cys Gly Asn Thr Ile Leu Val Asn Gly Lys Ala Trp
225                 230                 235                 240

Pro Tyr Met Glu Val Glu Pro Thr Tyr Arg Phe Arg Ile Leu Asn
                245                 250                 255

Ala Ser Asn Thr Arg Thr Phe Ser Leu Ser Leu Asn Asn Gly Gly Lys
            260                 265                 270

Phe Ile Gln Ile Gly Ser Asp Gly Gly Leu Leu Pro Arg Ser Val Lys
        275                 280                 285

Thr Gln Ser Ile Ser Leu Ala Pro Ala Glu Arg Tyr Asp Val Leu Ile
        290                 295                 300

Asp Phe Ser Ala Phe Asp Gly Glu His Ile Ile Leu Thr Asn Gly Thr
```

```
            305                 310                 315                 320
        Gly Cys Gly Gly Asp Ala Asp Pro Asp Thr Asp Ala Asn Val Met Gln
                        325                 330                 335

Phe Arg Val Thr Lys Pro Leu Lys Gly Ala Asp Thr Ser Arg Lys Pro
                        340                 345                 350

Lys Tyr Leu Ser Thr Met Pro Asn Val Thr Ser Lys Arg Ile His Asn
                        355                 360                 365

Ile Arg Met Leu Lys Leu Thr Asn Thr Gln Asp Lys Tyr Gly Arg Pro
                        370                 375                 380

Val Leu Thr Leu Asn Asn Lys Arg Trp His Asp Pro Val Thr Glu Ala
        385                 390                 395                 400

Pro Lys Leu Gly Thr Thr Glu Ile Trp Ser Ile Ile Asn Pro Met Gly
                        405                 410                 415

Gly Thr His Pro Ile His Leu His Leu Val Ser Phe Gln Ile Leu Asp
                        420                 425                 430

Arg Arg Pro Phe Asp Leu Glu Arg Tyr Asn Lys Phe Gly Asp Ile Val
                        435                 440                 445

Tyr Thr Gly Pro Ala Val Pro Pro Pro Ser Glu Lys Gly Trp Lys
                        450                 455                 460

Asp Thr Val Gln Ala His Ser Gly Glu Val Ile Arg Ile Ala Ala Thr
        465                 470                 475                 480

Phe Ala Pro Tyr Ser Gly Arg Tyr Val Trp His Cys His Ile Leu Glu
                        485                 490                 495

His Glu Asp Tyr Asp Met Met Arg Pro Met Asp Val Thr Asp Lys Gln
                        500                 505                 510

<210> SEQ ID NO 14
<211> LENGTH: 512
<212> TYPE: PRT
<213> ORGANISM: Bacillus spec

<400> SEQUENCE: 14

Met Ala Leu Glu Lys Phe Ala Asp Glu Leu Pro Ile Ile Glu Thr Leu
1               5                   10                  15

Gln Pro Gln Lys Lys Ser Asp Gly Ser Thr Tyr Tyr Glu Val Thr Met
                20                  25                  30

Lys Glu Cys Phe His Lys Leu His Arg Asp Leu Pro Pro Thr Arg Leu
                35                  40                  45

Trp Gly Tyr Asn Gly Leu Phe Pro Gly Pro Thr Ile Asp Val Asn Lys
                50                  55                  60

Asp Glu Asn Val Tyr Ile Lys Trp Met Asn Asp Leu Pro Asp Lys His
65                  70                  75                  80

Phe Leu Pro Val Asp His Thr Ile His His Ser Glu Ser Gly His Gln
                85                  90                  95

Glu Pro Asp Val Lys Thr Val Val His Leu His Gly Gly Ala Thr Pro
                100                 105                 110

Pro Asp Ser Asp Gly Tyr Pro Glu Ala Trp Phe Thr Lys Asp Phe Lys
                115                 120                 125

Glu Thr Gly Pro Tyr Phe Glu Arg Glu Val Tyr His Tyr Pro Asn Lys
                130                 135                 140

Gln Arg Gly Ala Val Leu Trp Tyr His Asp His Ala Met Ala Ile Thr
145                 150                 155                 160

Arg Leu Asn Val Tyr Ala Gly Leu Ala Gly Met Tyr Ile Ile Arg Glu
                165                 170                 175
```

```
Arg Lys Glu Lys Gln Leu Lys Leu Pro Ser Gly Glu Tyr Asp Val Pro
            180                 185                 190

Leu Met Ile Leu Asp Arg Thr Leu Asn Asp Asp Gly Ser Leu Ser Tyr
            195                 200                 205

Pro Ser Gly Pro Ala Asn Pro Ser Glu Thr Leu Pro Asp Pro Ser Ile
        210                 215                 220

Val Pro Phe Phe Cys Gly Asn Thr Ile Leu Val Asn Gly Lys Ala Trp
225                 230                 235                 240

Pro Tyr Met Glu Val Glu Pro Arg Thr Tyr Arg Phe Arg Ile Leu Asn
                245                 250                 255

Ala Ser Asn Thr Arg Thr Phe Ser Leu Ser Leu Asn Asn Gly Gly Lys
            260                 265                 270

Phe Ile Gln Ile Gly Ser Asp Gly Gly Leu Leu Pro Arg Ser Val Lys
        275                 280                 285

Thr Gln Ser Ile Ser Leu Ala Pro Ala Glu Arg Tyr Asp Val Leu Ile
    290                 295                 300

Asp Phe Ser Ala Phe Asp Gly Glu His Ile Ile Leu Thr Asn Gly Thr
305                 310                 315                 320

Gly Cys Gly Gly Asp Ala Asp Pro Asp Thr Asp Ala Asn Val Met Gln
                325                 330                 335

Phe Arg Val Thr Lys Pro Leu Lys Gly Ala Asp Thr Ser Arg Lys Pro
            340                 345                 350

Lys Tyr Leu Ser Thr Met Pro Asn Val Thr Ser Lys Arg Ile His Asn
        355                 360                 365

Ile Arg Met Leu Lys Leu Thr Asn Thr Gln Asp Lys Tyr Gly Arg Pro
    370                 375                 380

Val Leu Thr Leu Asn Asn Lys Arg Trp His Asp Pro Val Thr Glu Ala
385                 390                 395                 400

Pro Lys Leu Gly Thr Thr Glu Ile Trp Ser Ile Ile Asn Pro Met Gly
                405                 410                 415

Gly Thr His Pro Ile His Leu His Leu Val Ser Phe Gln Ile Leu Asp
            420                 425                 430

Arg Arg Pro Phe Asp Leu Glu Arg Tyr Asn Lys Phe Gly Asp Ile Val
        435                 440                 445

Tyr Thr Gly Pro Ala Val Pro Pro Pro Ser Glu Lys Gly Trp Lys
    450                 455                 460

Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
                485                 490                 495

His Glu Asp Tyr Asp Met Met Arg Pro Met Asp Val Thr Asp Lys Gln
            500                 505                 510

<210> SEQ ID NO 15
<211> LENGTH: 513
<212> TYPE: PRT
<213> ORGANISM: Bacillus spec

<400> SEQUENCE: 15

Met Thr Leu Glu Lys Phe Val Asp Ala Leu Pro Ile Pro Glu Thr Leu
1               5                   10                  15

Lys Pro Val Gln Gln Thr Lys Glu Lys Thr Tyr Tyr Glu Val Thr Met
            20                  25                  30

Glu Glu Cys Ala His Lys Leu His Arg Asp Leu Pro Pro Thr Arg Leu
        35                  40                  45
```

```
Trp Gly Tyr Asn Cys Gln Phe Pro Gly Pro Thr Ile Glu Val Asn Arg
     50                  55                  60

Asn Glu Asn Val Tyr Val Lys Trp Met Asn His Leu Ser Ser Thr His
 65                  70                  75                  80

Phe Leu Pro Val Asp His Thr Ile His His Ser Asp Ser Gln His Glu
                 85                  90                  95

Glu Pro Glu Val Lys Thr Val Val His Leu His Gly Val Thr Pro
                100                 105                 110

Glu Asp Ser Asp Gly Tyr Pro Glu Ala Trp Phe Thr Lys Asp Phe Glu
            115                 120                 125

Gln Thr Gly Pro Tyr Phe Lys Arg Glu Ile Tyr His Tyr Pro Asn Gln
        130                 135                 140

Gln Arg Gly Ala Ile Leu Trp Tyr His Asp His Ala Met Ala Leu Thr
145                 150                 155                 160

Arg Leu Asn Val Tyr Ala Gly Leu Ile Gly Ala Tyr Leu Ile His Asp
                165                 170                 175

Pro Lys Glu Lys Arg Leu Lys Leu Pro Ser Gly Glu Tyr Asp Val Pro
            180                 185                 190

Leu Leu Ile Thr Asp Arg Thr Ile Asn Gly Asp Gly Ser Leu Phe Tyr
        195                 200                 205

Pro Asn Gly Pro Glu Asn Pro Ser Pro Ser Leu Pro Asn Pro Ser Ile
210                 215                 220

Val Pro Ala Phe Cys Gly Glu Thr Ile Leu Val Asn Gly Lys Ala Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Asp Gly Glu
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Tyr Asp Ile Ile Ile
    290                 295                 300

Asp Phe Thr Ala Tyr Glu Gly Gln Ser Ile Ile Leu Ala Asn Ser Glu
305                 310                 315                 320

Gly Cys Gly Gly Asp Ala Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln Asn Glu Arg Ile His Asn
        355                 360                 365

Ile Arg Thr Leu Lys Leu Ala Gly Thr Gln Asp Glu Tyr Gly Arg Pro
    370                 375                 380

Val Leu Leu Leu Asn Asn Lys Arg Trp His Asp Pro Val Thr Glu Thr
385                 390                 395                 400

Pro Lys Ala Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
            420                 425                 430

Arg Arg Pro Phe Asp Ile Ala Arg Tyr Gln Glu Arg Gly Glu Leu Ser
        435                 440                 445

Tyr Thr Gly Pro Ala Val Pro Pro Pro Ser Glu Lys Gly Trp Lys
    450                 455                 460
```

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
            485                 490                 495

His Glu Asp Tyr Asp Met Met Arg Pro Met Asp Ile Thr Asp Pro His
        500                 505                 510

Lys

<210> SEQ ID NO 16
<211> LENGTH: 513
<212> TYPE: PRT
<213> ORGANISM: Bacillus spec

<400> SEQUENCE: 16

Met Thr Leu Glu Lys Phe Val Asp Ala Leu Pro Ile Pro Glu Thr Leu
1               5                   10                  15

Lys Pro Val Gln Gln Thr Lys Glu Lys Thr Tyr Tyr Glu Val Thr Met
            20                  25                  30

Glu Glu Cys Ala His Lys Leu His Arg Asp Leu Pro Pro Thr Arg Leu
        35                  40                  45

Trp Gly Tyr Asn Cys Gln Phe Pro Gly Pro Thr Ile Glu Val Asn Arg
    50                  55                  60

Asn Glu Asn Val Tyr Val Lys Trp Met Asn His Leu Ser Ser Thr His
65              70                  75                  80

Phe Leu Pro Val Asp His Thr Ile His His Ser Asp Ser Gln His Glu
                85                  90                  95

Glu Pro Glu Val Lys Thr Val Val His Leu His Gly Val Thr Pro
            100                 105                 110

Glu Asp Ser Asp Gly Tyr Pro Glu Ala Trp Phe Thr Lys Asp Phe Glu
        115                 120                 125

Gln Thr Gly Pro Tyr Phe Lys Arg Glu Ile Tyr His Tyr Pro Asn Gln
    130                 135                 140

Gln Arg Gly Ala Thr Leu Trp Tyr His Asp His Ala Met Ala Leu Thr
145                 150                 155                 160

Arg Leu Asn Val Tyr Ala Gly Leu Ile Gly Ala Tyr Leu Ile His Asp
                165                 170                 175

Pro Lys Glu Lys Arg Leu Lys Leu Pro Ser Gly Glu Tyr Asp Val Pro
            180                 185                 190

Leu Leu Ile Thr Asp Arg Thr Ile Asn Gly Asp Gly Ser Leu Phe Tyr
        195                 200                 205

Pro Asn Gly Pro Glu Asn Pro Ser Pro Ser Leu Pro Asn Pro Ser Ile
    210                 215                 220

Val Pro Ala Phe Cys Gly Glu Thr Ile Leu Val Asn Gly Lys Ala Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Asp Gly Glu
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Tyr Asp Ile Ile Ile
    290                 295                 300

Asp Phe Thr Ala Tyr Glu Gly Gln Ser Ile Ile Leu Ala Asn Ser Glu
305                 310                 315                 320

```
Gly Cys Gly Gly Asp Ala Asn Pro Glu Thr Asp Ala Asn Ile Met Gln
            325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln Asn Glu Arg Ile His Asn
            355                 360                 365

Ile Arg Thr Leu Lys Leu Ala Gly Thr Gln Asp Glu Tyr Gly Arg Pro
            370                 375                 380

Val Leu Leu Leu Asn Asn Lys Arg Trp His Asp Pro Val Thr Glu Thr
385                 390                 395                 400

Pro Lys Ala Gly Thr Thr Glu Ile Trp Ser Ile Ile Asn Pro Thr Arg
            405                 410                 415

Gly Thr His Pro Ile His Leu His Leu Val Ser Phe Arg Val Leu Asp
            420                 425                 430

Arg Arg Pro Phe Asp Ile Ala Arg Tyr Gln Glu Arg Gly Glu Leu Ser
            435                 440                 445

Tyr Thr Gly Pro Ala Val Pro Pro Pro Ser Glu Lys Gly Trp Lys
            450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
            485                 490                 495

His Glu Asp Tyr Asp Met Met Arg Pro Met Asp Ile Thr Asp Pro His
            500                 505                 510

Lys

<210> SEQ ID NO 17
<211> LENGTH: 513
<212> TYPE: PRT
<213> ORGANISM: Bacillus spec

<400> SEQUENCE: 17

Met Thr Leu Glu Lys Phe Val Asp Ala Leu Pro Ile Pro Glu Thr Leu
1               5                   10                  15

Lys Pro Val Gln Gln Thr Lys Glu Lys Thr Tyr Tyr Glu Val Thr Met
            20                  25                  30

Glu Glu Cys Ala His Lys Leu His Arg Asp Leu Pro Pro Thr Arg Leu
            35                  40                  45

Trp Gly Tyr Asn Cys Gln Phe Pro Gly Pro Thr Ile Glu Val Asn Arg
        50                  55                  60

Asn Glu Asn Val Tyr Val Lys Trp Met Asn His Leu Ser Ser Thr His
65                  70                  75                  80

Phe Leu Pro Val Asp His Thr Ile His His Ser Asp Ser Gln His Glu
            85                  90                  95

Glu Pro Glu Val Lys Thr Val Val His Leu His Gly Gly Val Thr Pro
            100                 105                 110

Glu Asp Ser Asp Gly Tyr Pro Glu Ala Trp Phe Thr Lys Asp Phe Glu
            115                 120                 125

Gln Thr Gly Pro Tyr Phe Lys Arg Glu Ile Tyr His Tyr Pro Asn Gln
        130                 135                 140

Gln Arg Gly Ala Pro Leu Trp Tyr His Asp His Ala Met Ala Leu Thr
145                 150                 155                 160

Arg Leu Asn Val Tyr Ala Gly Leu Ile Gly Ala Tyr Leu Ile His Asp
            165                 170                 175
```

```
Pro Lys Glu Lys Arg Leu Lys Leu Pro Ser Gly Tyr Asp Val Pro
            180                 185                 190

Leu Leu Ile Thr Asp Arg Thr Ile Asn Gly Asp Gly Ser Leu Phe Tyr
            195                 200                 205

Pro Asn Gly Pro Glu Asn Pro Ser Pro Ser Leu Pro Asn Pro Ser Ile
210                 215                 220

Val Pro Ala Phe Cys Gly Glu Thr Ile Leu Val Asn Gly Lys Ala Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Asp Gly Glu
            260                 265                 270

Phe Ile Gln Ile Gly Ser Asp Gly Gly Leu Leu Pro Arg Ser Val Lys
            275                 280                 285

Leu Asn Ser Phe Ser Leu Ala Pro Ala Glu Arg Tyr Asp Ile Ile Ile
            290                 295                 300

Asp Phe Thr Ala Tyr Glu Gly Gln Ser Ile Ile Leu Ala Asn Ser Glu
305                 310                 315                 320

Gly Cys Gly Gly Asp Ala Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln Asn Glu Arg Ile His Asn
            355                 360                 365

Ile Arg Thr Leu Lys Leu Ala Gly Thr Gln Asp Glu Tyr Gly Arg Pro
370                 375                 380

Val Leu Leu Leu Asn Asn Lys Arg Trp His Asp Pro Val Thr Glu Thr
385                 390                 395                 400

Pro Lys Ala Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
            420                 425                 430

Arg Arg Pro Phe Asp Ile Ala Arg Tyr Gln Glu Arg Gly Glu Leu Ser
            435                 440                 445

Tyr Thr Gly Pro Ala Val Pro Pro Pro Ser Glu Lys Gly Trp Lys
            450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
            500                 505                 510

Lys

<210> SEQ ID NO 18
<211> LENGTH: 513
<212> TYPE: PRT
<213> ORGANISM: Bacillus spec

<400> SEQUENCE: 18

Met Thr Leu Glu Lys Phe Val Asp Ala Leu Pro Ile Pro Glu Thr Leu
1               5                   10                  15

Lys Pro Val Gln Gln Thr Lys Glu Lys Thr Tyr Tyr Glu Val Thr Met
            20                  25                  30
```

```
Glu Glu Cys Ala His Lys Leu His Arg Asp Leu Pro Pro Thr Arg Leu
         35                  40                  45

Trp Gly Tyr Asn Cys Gln Phe Pro Gly Pro Thr Ile Glu Val Asn Arg
 50                  55                  60

Asn Glu Asn Val Tyr Val Lys Trp Met Asn His Leu Ser Ser Thr His
 65                  70                  75                  80

Phe Leu Pro Val Asp His Thr Ile His His Ser Asp Ser Gln His Glu
                 85                  90                  95

Glu Pro Glu Val Lys Thr Val Val His Leu His Gly Gly Val Thr Pro
            100                 105                 110

Glu Asp Ser Asp Gly Tyr Pro Glu Ala Trp Phe Thr Lys Asp Phe Glu
            115                 120                 125

Gln Thr Gly Pro Tyr Phe Lys Arg Glu Ile Tyr His Tyr Pro Asn Gln
130                 135                 140

Gln Arg Gly Ala Ala Leu Trp Tyr His Asp His Ala Met Ala Leu Thr
145                 150                 155                 160

Arg Leu Asn Val Tyr Ala Gly Leu Ile Gly Ala Tyr Leu Ile His Asp
                165                 170                 175

Pro Lys Glu Lys Arg Leu Lys Leu Pro Ser Gly Glu Tyr Asp Val Pro
            180                 185                 190

Leu Leu Ile Thr Asp Arg Thr Ile Asn Gly Asp Gly Ser Leu Phe Tyr
            195                 200                 205

Pro Asn Gly Pro Glu Asn Pro Ser Pro Ser Leu Pro Asn Pro Ser Ile
210                 215                 220

Val Pro Ala Phe Cys Gly Glu Thr Ile Leu Val Asn Gly Lys Ala Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Asp Gly Glu
            260                 265                 270

Phe Ile Gln Ile Gly Ser Asp Gly Gly Leu Leu Pro Arg Ser Val Lys
            275                 280                 285

Leu Asn Ser Phe Ser Leu Ala Pro Ala Glu Arg Tyr Asp Ile Ile Ile
290                 295                 300

Asp Phe Thr Ala Tyr Glu Gly Gln Ser Ile Ile Leu Ala Asn Ser Glu
305                 310                 315                 320

Gly Cys Gly Gly Asp Ala Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln Asn Glu Arg Ile His Asn
            355                 360                 365

Ile Arg Thr Leu Lys Leu Ala Gly Thr Gln Asp Glu Tyr Gly Arg Pro
370                 375                 380

Val Leu Leu Leu Asn Asn Lys Arg Trp His Asp Pro Val Thr Glu Thr
385                 390                 395                 400

Pro Lys Ala Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
            420                 425                 430

Arg Arg Pro Phe Asp Ile Ala Arg Tyr Gln Glu Arg Gly Glu Leu Ser
            435                 440                 445

Tyr Thr Gly Pro Ala Val Pro Pro Pro Ser Glu Lys Gly Trp Lys
```

```
            450                 455                 460
Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                    485                 490                 495

His Glu Asp Tyr Asp Met Met Arg Pro Met Asp Ile Thr Asp Pro His
                500                 505                 510

Lys

<210> SEQ ID NO 19
<211> LENGTH: 513
<212> TYPE: PRT
<213> ORGANISM: Bacillus spec

<400> SEQUENCE: 19

Met Thr Leu Glu Lys Phe Val Asp Ala Leu Pro Ile Pro Glu Thr Leu
1               5                   10                  15

Lys Pro Val Gln Gln Thr Lys Glu Lys Thr Tyr Tyr Glu Val Thr Met
                20                  25                  30

Glu Glu Cys Ala His Lys Leu His Arg Asp Leu Pro Pro Thr Arg Leu
            35                  40                  45

Trp Gly Tyr Asn Cys Gln Phe Pro Gly Pro Thr Ile Glu Val Asn Arg
        50                  55                  60

Asn Glu Asn Val Tyr Val Lys Trp Met Asn His Leu Ser Ser Thr His
65                  70                  75                  80

Phe Leu Pro Val Asp His Thr Ile His His Ser Asp Ser Gln His Glu
                85                  90                  95

Glu Pro Glu Val Lys Thr Val Val His Leu His Gly Gly Val Thr Pro
            100                 105                 110

Glu Asp Ser Asp Gly Tyr Pro Glu Ala Trp Phe Thr Lys Asp Phe Glu
        115                 120                 125

Gln Thr Gly Pro Tyr Phe Lys Arg Glu Ile Tyr His Tyr Pro Asn Gln
    130                 135                 140

Gln Arg Gly Ala Gly Leu Trp Tyr His Asp His Ala Met Ala Leu Thr
145                 150                 155                 160

Arg Leu Asn Val Tyr Ala Gly Leu Ile Gly Ala Tyr Leu Ile His Asp
                165                 170                 175

Pro Lys Glu Lys Arg Leu Lys Leu Pro Ser Gly Glu Tyr Asp Val Pro
            180                 185                 190

Leu Leu Ile Thr Asp Arg Thr Ile Asn Gly Asp Gly Ser Leu Phe Tyr
        195                 200                 205

Pro Asn Gly Pro Glu Asn Pro Ser Pro Ser Leu Pro Asn Pro Ser Ile
    210                 215                 220

Val Pro Ala Phe Cys Gly Glu Thr Ile Leu Val Asn Gly Lys Ala Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Asp Gly Glu
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Tyr Asp Ile Ile Ile
    290                 295                 300

Asp Phe Thr Ala Tyr Glu Gly Gln Ser Ile Ile Leu Ala Asn Ser Glu
```

```
            305                 310                 315                 320

Gly Cys Gly Gly Asp Ala Asn Pro Glu Thr Asp Ala Asn Ile Met Gln
                325                 330                 335

Phe Arg Val Thr Lys Pro Leu Ala Gln Lys Asp Glu Ser Arg Lys Pro
                340                 345                 350

Lys Tyr Leu Ala Ser Tyr Pro Ser Val Gln Asn Glu Arg Ile His Asn
                355                 360                 365

Ile Arg Thr Leu Lys Leu Ala Gly Thr Gln Asp Glu Tyr Gly Arg Pro
            370                 375                 380

Val Leu Leu Leu Asn Asn Lys Arg Trp His Asp Pro Val Thr Glu Thr
385                 390                 395                 400

Pro Lys Ala Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
                420                 425                 430

Arg Arg Pro Phe Asp Ile Ala Arg Tyr Gln Glu Arg Gly Glu Leu Ser
                435                 440                 445

Tyr Thr Gly Pro Ala Val Pro Pro Pro Ser Glu Lys Gly Trp Lys
            450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
                500                 505                 510

Lys

<210> SEQ ID NO 20
<211> LENGTH: 513
<212> TYPE: PRT
<213> ORGANISM: Bacillus spec

<400> SEQUENCE: 20

Met Thr Leu Glu Lys Phe Val Asp Ala Leu Pro Ile Pro Glu Thr Leu
1               5                   10                  15

Lys Pro Val Gln Gln Thr Lys Glu Lys Thr Tyr Tyr Glu Val Thr Met
                20                  25                  30

Glu Glu Cys Ala His Lys Leu His Arg Asp Leu Pro Pro Thr Arg Leu
            35                  40                  45

Trp Gly Tyr Asn Cys Gln Phe Pro Gly Pro Thr Ile Glu Val Asn Arg
    50                  55                  60

Asn Glu Asn Val Tyr Val Lys Trp Met Asn His Leu Ser Ser Thr His
65                  70                  75                  80

Phe Leu Pro Val Asp His Thr Ile His His Ser Asp Ser Gln His Glu
                85                  90                  95

Glu Pro Glu Val Lys Thr Val His Leu His Gly Gly Val Thr Pro
                100                 105                 110

Glu Asp Ser Asp Gly Tyr Pro Glu Ala Trp Phe Thr Lys Asp Phe Glu
            115                 120                 125

Gln Thr Gly Pro Tyr Phe Lys Arg Glu Ile Tyr Tyr Pro Asn Gln
            130                 135                 140

Gln Arg Gly Ala Ser Leu Trp Tyr His Asp His Ala Met Ala Leu Thr
145                 150                 155                 160

Arg Leu Asn Val Tyr Ala Gly Leu Ile Gly Ala Tyr Leu Ile His Asp
```

```
                165                 170                 175
Pro Lys Glu Lys Arg Leu Lys Leu Pro Ser Gly Glu Tyr Asp Val Pro
            180                 185                 190

Leu Leu Ile Thr Asp Arg Thr Ile Asn Gly Asp Gly Ser Leu Phe Tyr
        195                 200                 205

Pro Asn Gly Pro Glu Asn Pro Ser Pro Ser Leu Pro Asn Pro Ser Ile
    210                 215                 220

Val Pro Ala Phe Cys Gly Glu Thr Ile Leu Val Asn Gly Lys Ala Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Asp Gly Glu
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Tyr Asp Ile Ile Ile
    290                 295                 300

Asp Phe Thr Ala Tyr Glu Gly Gln Ser Ile Ile Leu Ala Asn Ser Glu
305                 310                 315                 320

Gly Cys Gly Gly Asp Ala Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln Asn Glu Arg Ile His Asn
        355                 360                 365

Ile Arg Thr Leu Lys Leu Ala Gly Thr Gln Asp Glu Tyr Gly Arg Pro
    370                 375                 380

Val Leu Leu Leu Asn Asn Lys Arg Trp His Asp Pro Val Thr Glu Thr
385                 390                 395                 400

Pro Lys Ala Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
            420                 425                 430

Arg Arg Pro Phe Asp Ile Ala Arg Tyr Gln Glu Arg Gly Glu Leu Ser
        435                 440                 445

Tyr Thr Gly Pro Ala Val Pro Pro Ser Glu Lys Gly Trp Lys
    450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
            500                 505                 510

Lys

<210> SEQ ID NO 21
<211> LENGTH: 513
<212> TYPE: PRT
<213> ORGANISM: Bacillus spec

<400> SEQUENCE: 21

Met Thr Leu Glu Lys Phe Val Asp Ala Leu Pro Ile Pro Glu Thr Leu
1               5                   10                  15

Lys Pro Val Gln Gln Thr Lys Glu Lys Thr Tyr Tyr Glu Val Thr Met
```

-continued

```
             20                  25                  30
Glu Glu Cys Ala His Lys Leu His Arg Asp Leu Pro Pro Thr Arg Leu
         35                  40                  45
Trp Gly Tyr Asn Cys Gln Phe Pro Gly Pro Thr Ile Glu Val Asn Arg
 50                  55                  60
Asn Glu Asn Val Tyr Val Lys Trp Met Asn His Leu Ser Ser Thr His
 65                  70                  75                  80
Phe Leu Pro Val Asp His Thr Ile His His Ser Asp Ser Gln His Glu
                 85                  90                  95
Glu Pro Glu Val Lys Thr Val Val His Leu His Gly Val Thr Pro
                100                 105                 110
Glu Asp Ser Asp Gly Tyr Pro Glu Ala Trp Phe Thr Lys Asp Phe Glu
                115                 120                 125
Gln Thr Gly Pro Tyr Phe Lys Arg Glu Ile Tyr His Tyr Pro Asn Gln
                130                 135                 140
Gln Arg Gly Ala Cys Leu Trp Tyr His Asp His Ala Met Ala Leu Thr
145                 150                 155                 160
Arg Leu Asn Val Tyr Ala Gly Leu Ile Gly Ala Tyr Leu Ile His Asp
                165                 170                 175
Pro Lys Glu Lys Arg Leu Lys Leu Pro Ser Gly Glu Tyr Asp Val Pro
                180                 185                 190
Leu Leu Ile Thr Asp Arg Thr Ile Asn Gly Asp Gly Ser Leu Phe Tyr
                195                 200                 205
Pro Asn Gly Pro Glu Asn Pro Ser Pro Ser Leu Pro Asn Pro Ser Ile
                210                 215                 220
Val Pro Ala Phe Cys Gly Glu Thr Ile Leu Val Asn Gly Lys Ala Trp
225                 230                 235                 240
Pro Tyr Leu Glu Val Glu Pro Arg Lys Tyr Arg Phe Arg Val Ile Asn
                245                 250                 255
Ala Ser Asn Thr Arg Thr Tyr Asn Leu Ser Leu Asp Asn Asp Gly Glu
                260                 265                 270
Phe Ile Gln Ile Gly Ser Asp Gly Gly Leu Leu Pro Arg Ser Val Lys
                275                 280                 285
Leu Asn Ser Phe Ser Leu Ala Pro Ala Glu Arg Tyr Asp Ile Ile Ile
                290                 295                 300
Asp Phe Thr Ala Tyr Glu Gly Gln Ser Ile Ile Leu Ala Asn Ser Glu
305                 310                 315                 320
Gly Cys Gly Gly Asp Ala Asn Pro Glu Thr Asp Ala Asn Ile Met Gln
                325                 330                 335
Phe Arg Val Thr Lys Pro Leu Ala Gln Lys Asp Glu Ser Arg Lys Pro
                340                 345                 350
Lys Tyr Leu Ala Ser Tyr Pro Ser Val Gln Asn Glu Arg Ile His Asn
                355                 360                 365
Ile Arg Thr Leu Lys Leu Ala Gly Thr Gln Asp Glu Tyr Gly Arg Pro
                370                 375                 380
Val Leu Leu Leu Asn Asn Lys Arg Trp His Asp Pro Val Thr Glu Thr
385                 390                 395                 400
Pro Lys Ala Gly Thr Thr Glu Ile Trp Ser Ile Ile Asn Pro Thr Arg
                405                 410                 415
Gly Thr His Pro Ile His Leu His Leu Val Ser Phe Arg Val Leu Asp
                420                 425                 430
Arg Arg Pro Phe Asp Ile Ala Arg Tyr Gln Glu Arg Gly Glu Leu Ser
                435                 440                 445
```

```
Tyr Thr Gly Pro Ala Val Pro Pro Pro Ser Glu Lys Gly Trp Lys
        450                 455                 460

Asp Thr Ile Gln Ala His Ala Gly Glu Val Leu Arg Ile Ala Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
                500                 505                 510

Lys

<210> SEQ ID NO 22
<211> LENGTH: 513
<212> TYPE: PRT
<213> ORGANISM: Bacillus spec

<400> SEQUENCE: 22

Met Thr Leu Glu Lys Phe Val Asp Ala Leu Pro Ile Pro Glu Thr Leu
1               5                   10                  15

Lys Pro Val Gln Gln Thr Lys Glu Lys Thr Tyr Tyr Glu Val Thr Met
                20                  25                  30

Glu Glu Cys Ala His Lys Leu His Arg Asp Leu Pro Pro Thr Arg Leu
            35                  40                  45

Trp Gly Tyr Asn Cys Gln Phe Pro Gly Pro Thr Ile Glu Val Asn Arg
        50                  55                  60

Asn Glu Asn Val Tyr Val Lys Trp Met Asn His Leu Ser Ser Thr His
65                  70                  75                  80

Phe Leu Pro Val Asp His Thr Ile His His Ser Asp Ser Gln His Glu
                85                  90                  95

Glu Pro Glu Val Lys Thr Val Val His Leu His Gly Gly Val Thr Pro
            100                 105                 110

Glu Asp Ser Asp Gly Tyr Pro Glu Ala Trp Phe Thr Lys Asp Phe Glu
        115                 120                 125

Gln Thr Gly Pro Tyr Phe Lys Arg Glu Ile Tyr His Tyr Pro Asn Gln
130                 135                 140

Gln Arg Gly Ala Asp Leu Trp Tyr His Asp His Ala Met Ala Leu Thr
145                 150                 155                 160

Arg Leu Asn Val Tyr Ala Gly Leu Ile Gly Ala Tyr Leu Ile His Asp
                165                 170                 175

Pro Lys Glu Lys Arg Leu Lys Leu Pro Ser Gly Glu Tyr Asp Val Pro
            180                 185                 190

Leu Leu Ile Thr Asp Arg Thr Ile Asn Gly Asp Gly Ser Leu Phe Tyr
        195                 200                 205

Pro Asn Gly Pro Glu Asn Pro Ser Pro Ser Leu Asn Pro Ser Ile
210                 215                 220

Val Pro Ala Phe Cys Gly Glu Thr Ile Leu Val Asn Gly Lys Ala Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Asp Gly Glu
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Tyr Asp Ile Ile Ile
        290                 295                 300
```

```
Asp Phe Thr Ala Tyr Glu Gly Gln Ser Ile Ile Leu Ala Asn Ser Glu
305                 310                 315                 320

Gly Cys Gly Gly Asp Ala Asn Pro Glu Thr Asp Ala Asn Ile Met Gln
            325                 330                 335

Phe Arg Val Thr Lys Pro Leu Ala Gln Lys Asp Glu Ser Arg Lys Pro
                340                 345                 350

Lys Tyr Leu Ala Ser Tyr Pro Ser Val Gln Asn Glu Arg Ile His Asn
            355                 360                 365

Ile Arg Thr Leu Lys Leu Ala Gly Thr Gln Asp Glu Tyr Gly Arg Pro
        370                 375                 380

Val Leu Leu Asn Asn Lys Arg Trp His Asp Pro Val Thr Glu Thr
385                 390                 395                 400

Pro Lys Ala Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
                420                 425                 430

Arg Arg Pro Phe Asp Ile Ala Arg Tyr Gln Glu Arg Gly Glu Leu Ser
            435                 440                 445

Tyr Thr Gly Pro Ala Val Pro Pro Pro Ser Glu Lys Gly Trp Lys
450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
            500                 505                 510

Lys

<210> SEQ ID NO 23
<211> LENGTH: 513
<212> TYPE: PRT
<213> ORGANISM: Bacillus spec

<400> SEQUENCE: 23

Met Thr Leu Glu Lys Phe Val Asp Ala Leu Pro Ile Pro Glu Thr Leu
1               5                   10                  15

Lys Pro Val Gln Gln Thr Lys Glu Lys Thr Tyr Tyr Glu Val Thr Met
                20                  25                  30

Glu Glu Cys Ala His Lys Leu His Arg Asp Leu Pro Pro Thr Arg Leu
            35                  40                  45

Trp Gly Tyr Asn Cys Gln Phe Pro Gly Pro Thr Ile Glu Val Asn Arg
        50                  55                  60

Asn Glu Asn Val Tyr Val Lys Trp Met Asn Leu Ser Ser Thr His
65                  70                  75                  80

Phe Leu Pro Val Asp His Thr Ile His His Ser Asp Ser Gln His Glu
                85                  90                  95

Glu Pro Glu Val Lys Thr Val Val His Leu His Gly Gly Val Thr Pro
                100                 105                 110

Glu Asp Ser Asp Gly Tyr Pro Glu Ala Trp Phe Thr Lys Asp Phe Glu
            115                 120                 125

Gln Thr Gly Pro Tyr Phe Lys Arg Glu Ile Tyr His Tyr Pro Asn Gln
        130                 135                 140

Gln Arg Gly Ala Asn Leu Trp Tyr His Asp His Ala Met Ala Leu Thr
145                 150                 155                 160
```

Arg Leu Asn Val Tyr Ala Gly Leu Ile Gly Ala Tyr Leu Ile His Asp
            165                 170                 175

Pro Lys Glu Lys Arg Leu Lys Leu Pro Ser Gly Glu Tyr Asp Val Pro
            180                 185                 190

Leu Leu Ile Thr Asp Arg Thr Ile Asn Gly Asp Gly Ser Leu Phe Tyr
            195                 200                 205

Pro Asn Gly Pro Glu Asn Pro Ser Pro Ser Leu Pro Asn Pro Ser Ile
            210                 215                 220

Val Pro Ala Phe Cys Gly Glu Thr Ile Leu Val Asn Gly Lys Ala Trp
225                 230                 235                 240

Pro Tyr Leu Glu Val Glu Pro Arg Lys Tyr Arg Phe Arg Val Ile Asn
            245                 250                 255

Ala Ser Asn Thr Arg Thr Tyr Asn Leu Ser Leu Asp Asn Asp Gly Glu
            260                 265                 270

Phe Ile Gln Ile Gly Ser Asp Gly Gly Leu Leu Pro Arg Ser Val Lys
            275                 280                 285

Leu Asn Ser Phe Ser Leu Ala Pro Ala Glu Arg Tyr Asp Ile Ile Ile
            290                 295                 300

Asp Phe Thr Ala Tyr Glu Gly Gln Ser Ile Ile Leu Ala Asn Ser Glu
305                 310                 315                 320

Gly Cys Gly Gly Asp Ala Asn Pro Glu Thr Asp Ala Asn Ile Met Gln
            325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln Asn Glu Arg Ile His Asn
            355                 360                 365

Ile Arg Thr Leu Lys Leu Ala Gly Thr Gln Asp Glu Tyr Gly Arg Pro
            370                 375                 380

Val Leu Leu Leu Asn Asn Lys Arg Trp His Asp Pro Val Thr Glu Thr
385                 390                 395                 400

Pro Lys Ala Gly Thr Thr Glu Ile Trp Ser Ile Ile Asn Pro Thr Arg
            405                 410                 415

Gly Thr His Pro Ile His Leu His Leu Val Ser Phe Arg Val Leu Asp
            420                 425                 430

Arg Arg Pro Phe Asp Ile Ala Arg Tyr Gln Glu Arg Gly Glu Leu Ser
            435                 440                 445

Tyr Thr Gly Pro Ala Val Pro Pro Pro Ser Glu Lys Gly Trp Lys
            450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
            485                 490                 495

His Glu Asp Tyr Asp Met Met Arg Pro Met Asp Ile Thr Asp Pro His
            500                 505                 510

Lys

<210> SEQ ID NO 24
<211> LENGTH: 513
<212> TYPE: PRT
<213> ORGANISM: Bacillus spec

<400> SEQUENCE: 24

Met Thr Leu Glu Lys Phe Val Asp Ala Leu Pro Ile Pro Glu Thr Leu
1               5                   10                  15

Lys Pro Val Gln Gln Thr Lys Glu Lys Thr Tyr Tyr Glu Val Thr Met
            20                  25                  30

Glu Glu Cys Ala His Lys Leu His Arg Asp Leu Pro Pro Thr Arg Leu
        35                  40                  45

Trp Gly Tyr Asn Cys Gln Phe Pro Gly Pro Thr Ile Glu Val Asn Arg
    50                  55                  60

Asn Glu Asn Val Tyr Val Lys Trp Met Asn His Leu Ser Ser Thr His
65                  70                  75                  80

Phe Leu Pro Val Asp His Thr Ile His His Ser Asp Ser Gln His Glu
                85                  90                  95

Glu Pro Glu Val Lys Thr Val Val His Leu His Gly Gly Val Thr Pro
            100                 105                 110

Glu Asp Ser Asp Gly Tyr Pro Glu Ala Trp Phe Thr Lys Asp Phe Glu
        115                 120                 125

Gln Thr Gly Pro Tyr Phe Lys Arg Glu Ile Tyr His Tyr Pro Asn Gln
    130                 135                 140

Gln Arg Gly Ala Val Leu Trp Tyr His Asp His Ala Met Ala Leu Thr
145                 150                 155                 160

Arg Leu Asn Val Tyr Ala Gly Leu Ile Gly Ala Tyr Leu Ile His Asp
                165                 170                 175

Pro Lys Glu Lys Arg Leu Lys Leu Pro Ser Gly Glu Tyr Asp Val Pro
            180                 185                 190

Leu Leu Ile Thr Asp Arg Thr Ile Asn Gly Asp Gly Ser Leu Phe Tyr
        195                 200                 205

Pro Asn Gly Pro Glu Asn Pro Ser Pro Ser Leu Pro Asn Pro Ser Ile
    210                 215                 220

Val Pro Ala Phe Cys Gly Glu Thr Ile Leu Val Asn Gly Lys Ala Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Asp Gly Glu
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Tyr Asp Ile Ile Ile
    290                 295                 300

Asp Phe Thr Ala Tyr Glu Gly Gln Ser Ile Ile Leu Ala Asn Ser Glu
305                 310                 315                 320

Gly Cys Gly Gly Asp Ala Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln Asn Glu Arg Ile His Asn
        355                 360                 365

Ile Arg Thr Leu Lys Leu Ala Gly Thr Gln Asp Glu Tyr Gly Arg Pro
    370                 375                 380

Val Leu Leu Leu Asn Asn Lys Arg Trp His Asp Pro Val Thr Glu Thr
385                 390                 395                 400

Pro Lys Ala Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
            420                 425                 430

```
Arg Arg Pro Phe Asp Ile Ala Arg Tyr Gln Glu Arg Gly Glu Leu Ser
        435                 440                 445

Tyr Thr Gly Pro Ala Val Pro Pro Pro Ser Glu Lys Gly Trp Lys
450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
            500                 505                 510

Lys

<210> SEQ ID NO 25
<211> LENGTH: 24
<212> TYPE: DNA
<213> ORGANISM: Bacillus spec

<400> SEQUENCE: 25
gaaattaata cgactcacta tagg                                          24

<210> SEQ ID NO 26
<211> LENGTH: 30
<212> TYPE: DNA
<213> ORGANISM: BACILLUS SPEC

<400> SEQUENCE: 26
agcaccgcgt tgctgattcg gataatgata                                    30

<210> SEQ ID NO 27
<211> LENGTH: 33
<212> TYPE: DNA
<213> ORGANISM: BACILLUS SPEC

<400> SEQUENCE: 27
cgaatcagca acgcggtgct accttgtggt atc                                33

<210> SEQ ID NO 28
<211> LENGTH: 27
<212> TYPE: DNA
<213> ORGANISM: BACILLUS SPEC

<400> SEQUENCE: 28
ggttatgcta gttattgctc agcggtg                                       27

<210> SEQ ID NO 29
<211> LENGTH: 33
<212> TYPE: DNA
<213> ORGANISM: BACILLUS SPEC

<400> SEQUENCE: 29
cgaatcagca gcgcggcgct accttgtggt atc                                33

<210> SEQ ID NO 30
<211> LENGTH: 30
<212> TYPE: DNA
<213> ORGANISM: BACILLUS SPEC

<400> SEQUENCE: 30
agcgccgcgc tgctgattcg gataatgata                                    30

<210> SEQ ID NO 31
```

```
<211> LENGTH: 24
<212> TYPE: DNA
<213> ORGANISM: BACILLUS SPEC

<400> SEQUENCE: 31
gccccgcgct gtttgtttgg ataa                                          24

<210> SEQ ID NO 32
<211> LENGTH: 37
<212> TYPE: DNA
<213> ORGANISM: Bacillus spec

<400> SEQUENCE: 32
tccaaacaaa cagcgcgggg ctacgttatg gtatcac                            37

<210> SEQ ID NO 33
<211> LENGTH: 37
<212> TYPE: DNA
<213> ORGANISM: Bacillus spec

<400> SEQUENCE: 33
tccaaacaaa cagcgcgggg ctccgttatg gtatcac                            37

<210> SEQ ID NO 34
<211> LENGTH: 37
<212> TYPE: DNA
<213> ORGANISM: Bacillus spec

<400> SEQUENCE: 34
tccaaacaaa cagcgcgggg ctgcgttatg gtatcac                            37

<210> SEQ ID NO 35
<211> LENGTH: 37
<212> TYPE: DNA
<213> ORGANISM: Bacillus spec

<400> SEQUENCE: 35
tccaaacaaa cagcgcgggg ctggtttatg gtatcac                            37

<210> SEQ ID NO 36
<211> LENGTH: 37
<212> TYPE: DNA
<213> ORGANISM: Bacillus spec

<400> SEQUENCE: 36
tccaaacaaa cagcgcgggg cttctttatg gtatcac                            37

<210> SEQ ID NO 37
<211> LENGTH: 37
<212> TYPE: DNA
<213> ORGANISM: Bacillus spec

<400> SEQUENCE: 37
tccaaacaaa cagcgcgggg cttgtttatg gtatcac                            37

<210> SEQ ID NO 38
<211> LENGTH: 37
<212> TYPE: DNA
<213> ORGANISM: Bacillus spec

<400> SEQUENCE: 38
tccaaacaaa cagcgcgggg ctgatttatg gtatcac                            37
```

-continued

```
<210> SEQ ID NO 39
<211> LENGTH: 37
<212> TYPE: DNA
<213> ORGANISM: Bacillus spec

<400> SEQUENCE: 39
tccaaacaaa cagcgcgggg ctaacttatg gtatcac                              37

<210> SEQ ID NO 40
<211> LENGTH: 37
<212> TYPE: DNA
<213> ORGANISM: Bacillus spec

<400> SEQUENCE: 40
tccaaacaaa cagcgcgggg ctgtgttatg gtatcac                              37

<210> SEQ ID NO 41
<211> LENGTH: 30
<212> TYPE: DNA
<213> ORGANISM: Bacillus spec

<400> SEQUENCE: 41
agcaccgcgc tgctgattcg gataatgata                                      30

<210> SEQ ID NO 42
<211> LENGTH: 43
<212> TYPE: DNA
<213> ORGANISM: Bacillus spec

<400> SEQUENCE: 42
cgaatcagca gcgcggtgct actttgtggt atcacgatca cgc                       43

<210> SEQ ID NO 43
<211> LENGTH: 43
<212> TYPE: DNA
<213> ORGANISM: Bacillus spec

<400> SEQUENCE: 43
cgaatcagca gcgcggtgct ccgttgtggt atcacgatca cgc                       43

<210> SEQ ID NO 44
<211> LENGTH: 43
<212> TYPE: DNA
<213> ORGANISM: Bacillus spec

<400> SEQUENCE: 44
cgaatcagca gcgcggtgct gcgttgtggt atcacgatca cgc                       43

<210> SEQ ID NO 45
<211> LENGTH: 43
<212> TYPE: DNA
<213> ORGANISM: Bacillus spec

<400> SEQUENCE: 45
cgaatcagca gcgcggtgct ggtttgtggt atcacgatca cgc                       43

<210> SEQ ID NO 46
<211> LENGTH: 43
<212> TYPE: DNA
<213> ORGANISM: Bacillus spec

<400> SEQUENCE: 46
cgaatcagca gcgcggtgct tctttgtggt atcacgatca cgc                       43
```

<210> SEQ ID NO 47
<211> LENGTH: 43
<212> TYPE: DNA
<213> ORGANISM: Bacillus spec

<400> SEQUENCE: 47
cgaatcagca gcgcggtgct tgtttgtggt atcacgatca cgc          43

<210> SEQ ID NO 48
<211> LENGTH: 43
<212> TYPE: DNA
<213> ORGANISM: Bacillus spec

<400> SEQUENCE: 48
cgaatcagca gcgcggtgct gatttgtggt atcacgatca cgc          43

<210> SEQ ID NO 49
<211> LENGTH: 43
<212> TYPE: DNA
<213> ORGANISM: Bacillus spec

<400> SEQUENCE: 49
cgaatcagca gcgcggtgct aacttgtggt atcacgatca cgc          43

<210> SEQ ID NO 50
<211> LENGTH: 43
<212> TYPE: DNA
<213> ORGANISM: Bacillus spec

<400> SEQUENCE: 50
cgaatcagca gcgcggtgct gtgttgtggt atcacgatca cgc          43

<210> SEQ ID NO 51
<211> LENGTH: 513
<212> TYPE: PRT
<213> ORGANISM: Bacillus spec

<400> SEQUENCE: 51

Met Thr Leu Glu Lys Phe Val Asp Ala Leu Pro Ile Pro Asp Thr Leu
1               5                   10                  15

Lys Pro Val Gln Gln Thr Thr Glu Lys Thr Tyr Tyr Glu Val Thr Met
                20                  25                  30

Glu Glu Cys Ala His Gln Leu His Arg Asp Leu Pro Thr Arg Leu
            35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Glu His
65              70                  75                  80

Phe Leu Pro Ile Asp His Thr Ile His His Ser Asp Ser Gln His Glu
                85                  90                  95

Glu Pro Glu Val Lys Thr Val Val His Leu His Gly Gly Val Thr Pro
            100                 105                 110

Asp Asp Ser Asp Gly Tyr Pro Glu Ala Trp Phe Ser Lys Asp Phe Glu
        115                 120                 125

Gln Thr Gly Pro Tyr Phe Lys Arg Glu Val Tyr His Tyr Pro Asn Gln
    130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp 165                 170                 175
Pro Lys Glu Lys Arg Leu Lys Leu Pro Ser Gly Glu Tyr Asp Val Pro
                180                 185                 190

Leu Leu Ile Thr Asp Arg Thr Ile Asn Glu Asp Gly Ser Leu Phe Tyr
                195                 200                 205

Pro Ser Gly Pro Glu Asn Pro Ser Pro Ser Leu Pro Lys Pro Ser Ile
    210                 215                 220

Val Pro Ala Phe Cys Gly Asp Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Glu
                260                 265                 270

Phe Ile Gln Ile Gly Ser Asp Gly Gly Leu Leu Pro Arg Ser Val Lys
                275                 280                 285

Leu Asn Ser Phe Ser Leu Ala Pro Ala Glu Arg Tyr Asp Ile Ile Ile
            290                 295                 300

Asp Phe Thr Ala Tyr Glu Gly Gln Ser Ile Ile Leu Ala Asn Ser Glu
305                 310                 315                 320

Gly Cys Gly Gly Asp Ala Asn Pro Glu Thr Asp Ala Asn Ile Met Gln
                325                 330                 335

Phe Arg Val Thr Lys Pro Leu Ala Gln Lys Asp Glu Ser Arg Lys Pro
                340                 345                 350

Lys Tyr Leu Ala Ser Tyr Pro Ser Val Gln Asn Glu Arg Ile Gln Asn
            355                 360                 365

Ile Arg Thr Leu Lys Leu Ala Gly Thr Gln Asp Glu Tyr Gly Arg Pro
        370                 375                 380

Val Leu Leu Leu Asn Asn Lys Arg Trp His Asp Pro Val Thr Glu Ala
385                 390                 395                 400

Pro Lys Ala Gly Thr Thr Glu Ile Trp Ser Ile Val Asn Pro Thr Gln
                405                 410                 415

Gly Thr His Pro Ile His Leu His Leu Val Ser Phe Arg Val Leu Asp
                420                 425                 430

Arg Arg Pro Phe Asp Ile Ala Arg Tyr Gln Glu Arg Gly Glu Leu Ser
            435                 440                 445

Tyr Thr Gly Pro Ala Val Pro Pro Pro Ser Glu Lys Gly Trp Lys
    450                 455                 460

Asp Thr Ile Gln Ala His Ala Gly Glu Val Leu Arg Ile Ala Val Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
            500                 505                 510

Lys

<210> SEQ ID NO 52
<211> LENGTH: 513
<212> TYPE: PRT
<213> ORGANISM: Bacillus spec

<400> SEQUENCE: 52

Met Thr Leu Glu Lys Phe Ala Asp Ala Leu Pro Ile Pro Asp Thr Leu
1               5                   10                  15

Lys Pro Val Gln Gln Thr Thr Glu Lys Thr Tyr Tyr Glu Val Thr Met

-continued

```
               20                  25                  30
Glu Glu Cys Ala His Gln Leu His Arg Asp Leu Pro Pro Thr Arg Leu
             35                  40                  45

Trp Gly Tyr Asn Gly Leu Phe Pro Gly Pro Thr Ile Glu Val Lys Arg
 50                  55                  60

Asn Glu Asn Val Tyr Val Lys Trp Met Asn Asn Leu Pro Ser Glu His
 65                  70                  75                  80

Phe Leu Pro Ile Asp His Thr Ile His His Ser Asp Ser Gln His Glu
                 85                  90                  95

Glu Pro Glu Val Lys Thr Val Val His Leu His Gly Gly Val Thr Pro
            100                 105                 110

Asp Asp Ser Asp Gly Tyr Pro Glu Ala Trp Phe Ser Lys Asp Phe Glu
            115                 120                 125

Gln Thr Gly Pro Tyr Phe Lys Arg Glu Val Tyr His Tyr Pro Asn Gln
            130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Gly Glu Tyr Asp Val Pro
            180                 185                 190

Leu Leu Ile Thr Asp Arg Thr Ile Asn Glu Asp Gly Ser Leu Phe Tyr
            195                 200                 205

Pro Ser Gly Pro Glu Asn Pro Ser Pro Ser Leu Pro Lys Pro Ser Ile
            210                 215                 220

Val Pro Ala Phe Cys Gly Asp Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Glu
            260                 265                 270

Phe Ile Gln Ile Gly Ser Asp Gly Gly Leu Leu Pro Arg Ser Val Lys
            275                 280                 285

Leu Asn Ser Phe Ser Leu Ala Pro Ala Glu Arg Tyr Asp Ile Ile Ile
            290                 295                 300

Asp Phe Thr Ala Tyr Glu Gly Gln Ser Ile Ile Leu Ala Asn Ser Glu
305                 310                 315                 320

Gly Cys Gly Gly Asp Ala Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln Asn Glu Arg Ile Gln Asn
            355                 360                 365

Ile Arg Thr Leu Lys Leu Ala Gly Thr Gln Asp Glu Tyr Gly Arg Pro
            370                 375                 380

Val Leu Leu Leu Asn Asn Lys Arg Trp His Asp Pro Val Thr Glu Ala
385                 390                 395                 400

Pro Lys Ala Gly Thr Thr Glu Ile Trp Ser Ile Val Asn Pro Thr Gln
                405                 410                 415

Gly Thr His Pro Ile His Leu His Leu Val Ser Phe Arg Val Leu Asp
            420                 425                 430

Arg Arg Pro Phe Asp Ile Ala Arg Tyr Gln Glu Arg Gly Glu Leu Ser
            435                 440                 445
```

```
Tyr Thr Gly Pro Ala Val Pro Pro Pro Ser Glu Lys Gly Trp Lys
        450                 455                 460

Asp Thr Ile Gln Ala His Ala Gly Glu Val Leu Arg Ile Ala Val Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro Arg
                500                 505                 510

Lys

<210> SEQ ID NO 53
<211> LENGTH: 513
<212> TYPE: PRT
<213> ORGANISM: Bacillus spec

<400> SEQUENCE: 53

Met Thr Leu Glu Lys Phe Ala Asp Ala Leu Pro Ile Pro Asp Thr Leu
1               5                   10                  15

Lys Pro Val Gln Gln Thr Lys Glu Lys Thr Tyr Tyr Glu Val Thr Met
            20                  25                  30

Glu Glu Cys Thr His Gln Leu His Arg Asp Leu Pro Pro Thr Arg Leu
        35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Glu His
65                  70                  75                  80

Phe Leu Pro Ile Asp His Thr Ile His His Ser Asp Ser Gln His Glu
                85                  90                  95

Glu Pro Glu Val Lys Thr Val Val His Leu His Gly Gly Val Thr Pro
            100                 105                 110

Asp Asp Ser Asp Gly Tyr Pro Glu Ala Trp Phe Ser Lys Asp Phe Glu
        115                 120                 125

Gln Thr Gly Pro Tyr Phe Lys Arg Glu Val Tyr His Tyr Pro Asn Gln
130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Gly Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Gly Pro Glu Asn Pro Ser Pro Ser Leu Pro Asn Pro Ser Ile
    210                 215                 220

Val Pro Ala Phe Cys Gly Glu Thr Ile Leu Val Asn Gly Lys Ala Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Glu
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Tyr Asp Ile Ile Ile
    290                 295                 300
```

```
Asp Phe Thr Ala Tyr Glu Gly Gln Ser Ile Ile Leu Ala Asn Ser Glu
305                 310                 315                 320

Gly Cys Gly Gly Asp Val Asn Pro Glu Thr Asp Ala Asn Val Met Gln
                325                 330                 335

Phe Arg Val Thr Lys Pro Leu Gln Gln Lys Asp Glu Ser Arg Lys Pro
            340                 345                 350

Lys Tyr Leu Ala Ser Tyr Pro Ser Val Gln Asn Glu Arg Ile Gln Asn
            355                 360                 365

Ile Arg Thr Leu Lys Leu Ala Gly Thr Gln Asp Glu Tyr Gly Arg Pro
370                 375                 380

Val Leu Leu Asn Asn Lys Arg Trp His Asp Pro Val Thr Glu Ala
385                 390                 395                 400

Pro Lys Ala Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
                420                 425                 430

Arg Arg Pro Phe Asp Ile Ala Arg Tyr Gln Glu Arg Gly Glu Leu Ser
                435                 440                 445

Tyr Thr Gly Pro Ala Val Pro Pro Pro Ser Glu Lys Gly Trp Lys
450                 455                 460

Asp Thr Ile Gln Ala His Ala Gly Glu Val Leu Arg Ile Ala Val Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro Arg
                500                 505                 510

Lys

<210> SEQ ID NO 54
<211> LENGTH: 513
<212> TYPE: PRT
<213> ORGANISM: Bacillus spec

<400> SEQUENCE: 54

Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
                20                  25                  30

Glu Glu Cys Ala His Gln Leu His Arg Asp Leu Pro Pro Thr Arg Leu
            35                  40                  45

Trp Gly Tyr Asn Gly Leu Phe Pro Gly Pro Thr Ile Glu Val Lys Arg
50                  55                  60

Asn Glu Asn Val Tyr Val Lys Trp Met Asn Asn Leu Pro Ser Glu His
65                  70                  75                  80

Phe Leu Pro Ile Asp His Thr Ile His His Ser Asp Ser Gln His Glu
                85                  90                  95

Glu Pro Glu Val Lys Thr Val Val His Leu His Gly Gly Val Thr Pro
                100                 105                 110

Asp Asp Ser Asp Gly Tyr Pro Glu Ala Trp Phe Ser Lys Asp Phe Glu
            115                 120                 125

Gln Thr Gly Pro Tyr Phe Lys Arg Glu Val Tyr His Tyr Pro Asn Gln
            130                 135                 140

Gln Arg Gly Ala Ile Leu Trp Tyr His Asp His Ala Met Ala Leu Thr
145                 150                 155                 160
```

Arg Leu Asn Val Tyr Ala Gly Leu Val Gly Ala Tyr Ile Ile His Asp
            165                 170                 175

Pro Lys Glu Lys Arg Leu Lys Leu Pro Ser Gly Glu Tyr Asp Val Pro
            180                 185                 190

Leu Leu Leu Thr Asp Arg Thr Ile Asn Glu Asp Gly Ser Leu Phe Tyr
            195                 200                 205

Pro Ser Gly Pro Glu Asn Pro Ser Pro Ser Leu Pro Asn Pro Ser Ile
            210                 215                 220

Val Pro Ala Phe Cys Gly Glu Thr Ile Leu Val Asn Gly Lys Ala Trp
225                 230                 235                 240

Pro Tyr Phe Glu Val Glu Pro Arg Lys Tyr Arg Phe Arg Val Ile Asn
            245                 250                 255

Ala Ser Asn Thr Arg Thr Tyr Asn Leu Ser Leu Asp Asn Gly Gly Ala
            260                 265                 270

Phe Ile Gln Ile Gly Ser Asp Gly Gly Leu Leu Pro Arg Ser Val Lys
            275                 280                 285

Leu Asn Ser Phe Ser Leu Ala Pro Ala Glu Arg Tyr Asp Ile Ile Ile
            290                 295                 300

Asp Phe Thr Ala Tyr Glu Gly Gln Ser Ile Ile Leu Ala Asn Ser Glu
305                 310                 315                 320

Gly Cys Gly Gly Gly Val Asn Pro Glu Thr Asp Ala Asn Ile Met Gln
            325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln Asn Glu Lys Ile Gln Asn
            355                 360                 365

Ile Arg Thr Leu Lys Leu Ala Gly Thr Gln Asp Glu Tyr Gly Arg Pro
            370                 375                 380

Val Leu Leu Leu Asn Asn Lys Arg Trp His Asp Pro Val Thr Glu Ala
385                 390                 395                 400

Pro Lys Ala Gly Thr Thr Glu Ile Trp Ser Ile Val Asn Pro Thr Arg
            405                 410                 415

Gly Thr His Pro Ile His Leu His Leu Val Ser Phe Arg Val Leu Asp
            420                 425                 430

Arg Arg Pro Phe Asp Ile Ala Arg Tyr Gln Glu Arg Gly Glu Leu Ser
            435                 440                 445

Tyr Thr Gly Pro Ala Val Pro Pro Pro Ser Glu Lys Gly Trp Lys
            450                 455                 460

Asp Thr Ile Gln Ala His Ala Gly Glu Val Leu Arg Ile Ala Val Thr
465                 470                 475                 480

Phe Gly Pro Tyr Ser Gly Arg Tyr Val Trp His Cys His Ile Leu Glu
            485                 490                 495

His Glu Asp Tyr Asp Met Met Arg Pro Met Asp Ile Thr Glu Pro Arg
            500                 505                 510

Lys

<210> SEQ ID NO 55
<211> LENGTH: 513
<212> TYPE: PRT
<213> ORGANISM: Bacillus spec

<400> SEQUENCE: 55

Met Thr Leu Glu Lys Phe Val Asp Ala Leu Pro Ile Pro Asp Thr Leu
1               5                   10                  15

```
Lys Pro Val Gln Gln Ser Lys Glu Lys Thr Tyr Tyr Glu Val Thr Met
             20                  25                  30

Glu Glu Cys Thr His Gln Leu His Arg Asp Leu Pro Pro Thr Arg Leu
         35                  40                  45

Trp Gly Tyr Asn Gly Leu Phe Pro Gly Pro Thr Ile Glu Val Lys Arg
     50                  55                  60

Asn Glu Asn Val Tyr Val Lys Trp Met Asn Asn Leu Pro Ser Thr His
 65                  70                  75                  80

Phe Leu Pro Val Asp His Thr Ile His His Ser Asp Ser Gln His Glu
                 85                  90                  95

Glu Pro Glu Val Lys Thr Val Val His Leu His Gly Gly Val Thr Pro
             100                 105                 110

Asp Asp Ser Asp Gly Tyr Pro Glu Ala Trp Phe Ser Lys Asp Phe Glu
         115                 120                 125

Gln Thr Gly Pro Tyr Phe Lys Arg Glu Val Tyr His Tyr Pro Asn Gln
     130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                 165                 170                 175

Pro Lys Glu Lys Arg Leu Lys Leu Pro Ser Gly Glu Tyr Asp Val Pro
             180                 185                 190

Leu Leu Ile Thr Asp Arg Thr Ile Asn Glu Asp Gly Ser Leu Phe Tyr
         195                 200                 205

Pro Ser Gly Pro Glu Asn Pro Ser Pro Ser Leu Pro Asn Pro Ser Ile
     210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
                 245                 250                 255

Ala Ser Asn Thr Arg Thr Tyr Asn Leu Ser Leu Asp Asn Gly Gly Glu
             260                 265                 270

Phe Ile Gln Val Gly Ser Asp Gly Gly Leu Leu Pro Arg Ser Val Lys
         275                 280                 285

Leu Asn Ser Phe Ser Leu Ala Pro Ala Glu Arg Tyr Asp Ile Ile Ile
     290                 295                 300

Asp Phe Thr Ala Tyr Glu Gly Glu Ser Ile Ile Leu Ala Asn Ser Ala
305                 310                 315                 320

Gly Cys Gly Gly Asp Val Asn Pro Glu Thr Asp Ala Asn Ile Met Gln
                 325                 330                 335

Phe Lys Val Thr Lys Pro Leu Ala Gln Gln Asp Glu Ser Arg Lys Pro
             340                 345                 350

Lys Tyr Leu Ala Ser Tyr Pro Ser Val Gln His Glu Arg Ile Gln Asn
         355                 360                 365

Ile Arg Thr Leu Lys Leu Ala Gly Thr Gln Asp Lys Tyr Gly Arg Pro
     370                 375                 380

Val Leu Leu Leu Asn Asn Lys Arg Trp His Asp Pro Val Thr Glu Ala
385                 390                 395                 400

Pro Lys Ala Gly Thr Thr Glu Ile Trp Ser Ile Ile Asn Pro Thr Arg
                 405                 410                 415

Gly Thr His Pro Ile His Leu His Leu Val Ser Phe Arg Val Leu Asp
             420                 425                 430
```

```
Arg Arg Pro Phe Asp Ile Ala Arg Tyr Gln Glu Ser Gly Glu Leu Ser
            435                 440                 445

Tyr Thr Gly Pro Ala Ile Pro Pro Pro Ser Glu Lys Gly Trp Lys
    450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
            500                 505                 510

Lys

<210> SEQ ID NO 56
<211> LENGTH: 515
<212> TYPE: PRT
<213> ORGANISM: Bacillus spec

<400> SEQUENCE: 56

Met Lys Met Thr Leu Glu Lys Phe Val Asp Ala Leu Pro Ile Pro Asp
1               5                   10                  15

Thr Leu Lys Pro Val Gln Gln Ser Lys Glu Lys Thr Tyr Tyr Glu Val
            20                  25                  30

Thr Met Glu Glu Cys Thr His Gln Leu His Arg Asp Leu Pro Pro Thr
        35                  40                  45

Arg Leu Trp Gly Tyr Asn Gly Leu Phe Pro Gly Pro Thr Ile Glu Val
    50                  55                  60

Lys Arg Asn Glu Asn Val Tyr Val Lys Trp Met Asn Asn Leu Pro Ser
65                  70                  75                  80

Thr His Phe Leu Pro Ile Asp His Thr Ile His His Ser Asp Ser Gln
                85                  90                  95

His Glu Glu Pro Glu Val Lys Thr Val Val His Leu His Gly Gly Val
            100                 105                 110

Thr Pro Asp Asp Ser Asp Gly Tyr Pro Glu Ala Trp Phe Ser Lys Asp
        115                 120                 125

Phe Glu Gln Thr Gly Pro Tyr Phe Lys Arg Glu Val Tyr His Tyr Pro
    130                 135                 140

Asn Gln Gln Arg Gly Ala Ile Leu Trp Tyr His Asp His Ala Met Ala
145                 150                 155                 160

Leu Thr Arg Leu Asn Val Tyr Ala Gly Leu Val Gly Ala Tyr Ile Ile
                165                 170                 175

His Asp Pro Lys Glu Lys Arg Leu Lys Leu Pro Ser Asp Glu Tyr Asp
            180                 185                 190

Val Pro Leu Leu Ile Thr Asp Arg Thr Ile Asn Glu Asp Gly Ser Leu
        195                 200                 205

Phe Tyr Pro Ser Ala Pro Glu Asn Pro Ser Pro Ser Leu Pro Asn Pro
    210                 215                 220

Ser Ile Val Pro Ala Phe Cys Gly Glu Thr Ile Leu Val Asn Gly Lys
225                 230                 235                 240

Val Trp Pro Tyr Leu Glu Val Glu Pro Arg Lys Tyr Arg Phe Arg Val
                245                 250                 255

Ile Asn Ala Ser Asn Thr Arg Thr Tyr Asn Leu Ser Leu Asp Asn Gly
            260                 265                 270

Gly Glu Phe Ile Gln Ile Gly Ser Asp Gly Gly Leu Leu Pro Arg Ser
        275                 280                 285
```

```
Val Lys Leu Asn Ser Phe Ser Leu Ala Pro Ala Glu Arg Tyr Asp Ile
    290                 295                 300

Ile Ile Asp Phe Thr Ala Tyr Glu Gly Glu Ser Ile Ile Leu Ala Asn
305                 310                 315                 320

Ser Ala Gly Cys Gly Gly Asp Val Asn Pro Glu Thr Asp Ala Asn Ile
                325                 330                 335

Met Gln Phe Arg Val Thr Lys Pro Leu Ala Gln Lys Asp Glu Ser Arg
            340                 345                 350

Lys Pro Lys Tyr Leu Ala Ser Tyr Pro Ser Val Gln His Glu Arg Ile
        355                 360                 365

Gln Asn Ile Arg Thr Leu Lys Leu Ala Gly Thr Gln Asp Glu Tyr Gly
    370                 375                 380

Arg Pro Val Leu Leu Asn Asn Lys Arg Trp His Asp Pro Val Thr
385                 390                 395                 400

Glu Ala Pro Lys Val Gly Thr Thr Glu Ile Trp Ser Ile Ile Asn Pro
                405                 410                 415

Thr Arg Gly Thr His Pro Ile His Leu His Leu Val Ser Phe Arg Val
            420                 425                 430

Leu Asp Arg Arg Pro Phe Asp Ile Ala Arg Tyr Gln Glu Ser Gly Glu
        435                 440                 445

Leu Ser Tyr Thr Gly Pro Ala Val Pro Pro Pro Ser Glu Lys Gly
    450                 455                 460

Trp Lys Asp Thr Ile Gln Ala His Ala Gly Glu Val Leu Arg Ile Ala
465                 470                 475                 480

Ala Thr Phe Gly Pro Tyr Ser Gly Arg Tyr Val Trp His Cys His Ile
                485                 490                 495

Leu Glu His Glu Asp Tyr Asp Met Met Arg Pro Met Asp Ile Thr Asp
            500                 505                 510

Pro His Lys
        515

<210> SEQ ID NO 57
<211> LENGTH: 513
<212> TYPE: PRT
<213> ORGANISM: Bacillus spec

<400> SEQUENCE: 57

Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
            20                  25                  30

Glu Glu Cys Thr His Gln Leu His Arg Asp Leu Pro Pro Thr Arg Leu
        35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Thr His
65                  70                  75                  80

Phe Leu Pro Ile Asp His Thr Ile His His Ser Asp Ser Gln His Glu
                85                  90                  95

Glu Pro Glu Val Lys Thr Val His Leu His Gly Gly Val Thr Pro
            100                 105                 110

Asp Asp Ser Asp Gly Tyr Pro Glu Ala Trp Phe Ser Lys Asp Phe Glu
        115                 120                 125

Gln Thr Gly Pro Tyr Phe Lys Arg Glu Val Tyr His Tyr Pro Asn Gln
    130                 135                 140
```

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
            165                 170                 175

Pro Lys Glu Lys Arg Leu Lys Leu Pro Ser Asp Glu Tyr Asp Val Pro
        180                 185                 190

Leu Leu Ile Thr Asp Arg Thr Ile Asn Glu Asp Gly Ser Leu Phe Tyr
    195                 200                 205

Pro Ser Ala Pro Glu Asn Pro Ser Pro Ser Leu Pro Asn Pro Ser Ile
210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
            245                 250                 255

Ala Ser Asn Thr Arg Thr Tyr Asn Leu Ser Leu Asp Asn Gly Gly Glu
        260                 265                 270

Phe Ile Gln Ile Gly Ser Asp Gly Gly Leu Leu Pro Arg Ser Val Lys
    275                 280                 285

Leu Asn Ser Phe Ser Leu Ala Pro Ala Glu Arg Tyr Asp Ile Ile Ile
290                 295                 300

Asp Phe Thr Ala Tyr Glu Gly Glu Ser Ile Ile Leu Ala Asn Ser Ala
305                 310                 315                 320

Gly Cys Gly Gly Asp Val Asn Pro Glu Thr Asp Ala Asn Ile Met Gln
            325                 330                 335

Phe Arg Val Thr Lys Pro Leu Ala Gln Lys Asp Glu Ser Arg Lys Pro
        340                 345                 350

Lys Tyr Leu Ala Ser Tyr Pro Ser Val Gln His Glu Arg Ile Gln Asn
    355                 360                 365

Ile Arg Thr Leu Lys Leu Ala Gly Thr Gln Asp Glu Tyr Gly Arg Pro
370                 375                 380

Val Leu Leu Leu Asn Asn Lys Arg Trp His Asp Pro Val Thr Glu Ala
385                 390                 395                 400

Pro Lys Val Gly Thr Thr Glu Ile Trp Ser Ile Ile Asn Pro Thr Arg
            405                 410                 415

Gly Thr His Pro Ile His Leu His Leu Val Ser Phe Arg Val Leu Asp
        420                 425                 430

Arg Arg Pro Phe Asp Ile Ala Arg Tyr Gln Glu Ser Gly Glu Leu Ser
    435                 440                 445

Tyr Thr Gly Pro Ala Val Pro Pro Pro Ser Glu Lys Gly Trp Lys
    450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
            485                 490                 495

His Glu Asp Tyr Asp Met Met Arg Pro Met Asp Ile Thr Asp Pro His
        500                 505                 510

Lys

<210> SEQ ID NO 58
<211> LENGTH: 513
<212> TYPE: PRT
<213> ORGANISM: Bacillus spec

<400> SEQUENCE: 58

-continued

```
Met Thr Leu Glu Lys Phe Val Asp Ala Leu Pro Ile Pro Asp Thr Leu
1               5                   10                  15
Lys Pro Val Gln Gln Ser Lys Glu Lys Thr Tyr Tyr Glu Val Thr Met
            20                  25                  30
Glu Glu Cys Thr His Gln Ile His Arg Asp Leu Pro Pro Thr Arg Leu
        35                  40                  45
Trp Gly Tyr Asn Gly Leu Phe Pro Gly Pro Thr Ile Glu Val Lys Arg
    50                  55                  60
Asn Glu Asn Val Tyr Val Lys Trp Met Asn Asn Leu Pro Ser Thr His
65                  70                  75                  80
Phe Leu Pro Val Asp His Thr Ile His His Ser Asp Ser Gln His Glu
                85                  90                  95
Glu Pro Glu Val Lys Thr Val His Leu His Gly Gly Val Thr Pro
            100                 105                 110
Asp Asp Ser Asp Gly Tyr Pro Glu Ala Trp Phe Ser Lys Asp Phe Glu
        115                 120                 125
Gln Thr Gly Pro Tyr Phe Lys Arg Glu Val Tyr His Tyr Pro Asn Gln
    130                 135                 140
Gln Arg Gly Ala Ile Leu Trp Tyr His Asp His Ala Met Ala Leu Thr
145                 150                 155                 160
Arg Leu Asn Val Tyr Ala Gly Leu Val Gly Ala Tyr Ile Ile His Asp
                165                 170                 175
Pro Lys Glu Lys Arg Leu Lys Leu Pro Ser Gly Glu Tyr Asp Val Pro
            180                 185                 190
Leu Leu Ile Thr Asp Arg Thr Ile Asn Glu Asp Gly Ser Leu Phe Tyr
        195                 200                 205
Pro Ser Ala Pro Glu Asn Pro Ser Pro Ser Leu Pro Asn Pro Ser Ile
    210                 215                 220
Val Pro Ala Phe Cys Gly Glu Thr Ile Leu Val Asn Gly Lys Val Trp
225                 230                 235                 240
Pro Tyr Leu Glu Val Glu Pro Arg Lys Tyr Arg Phe Arg Val Ile Asn
                245                 250                 255
Ala Ser Asn Thr Arg Thr Tyr Asn Leu Ser Leu Asp Asn Gly Gly Glu
            260                 265                 270
Phe Ile Gln Val Gly Ser Asp Gly Gly Leu Leu Pro Arg Ser Val Lys
        275                 280                 285
Leu Asn Ser Phe Ser Leu Ala Pro Ala Glu Arg Tyr Asp Ile Ile Ile
    290                 295                 300
Asp Phe Thr Ala Tyr Glu Gly Glu Ser Ile Ile Leu Ala Asn Ser Ala
305                 310                 315                 320
Gly Cys Gly Gly Asp Val Asn Pro Glu Thr Asp Ala Asn Ile Met Gln
                325                 330                 335
Phe Arg Val Thr Lys Pro Leu Ala Gln Gln Asp Glu Ser Arg Lys Pro
            340                 345                 350
Lys Tyr Leu Ala Ser Tyr Pro Ser Val Gln His Glu Arg Ile Gln Asn
        355                 360                 365
Ile Arg Thr Leu Lys Leu Ala Gly Thr Gln Asp Glu Tyr Gly Arg Pro
    370                 375                 380
Val Leu Leu Leu Asn Asn Lys Arg Trp His Asp Pro Val Thr Glu Ala
385                 390                 395                 400
Pro Lys Ala Gly Thr Thr Glu Ile Trp Ser Ile Ile Asn Pro Thr Arg
                405                 410                 415
```

-continued

```
Gly Thr His Pro Ile His Leu His Leu Val Ser Phe Arg Val Leu Asp
            420                 425                 430

Arg Arg Pro Phe Asp Ile Ala Arg Tyr Gln Glu Ser Gly Glu Leu Ser
        435                 440                 445

Tyr Thr Gly Pro Ala Ile Pro Pro Pro Ser Glu Lys Gly Trp Lys
    450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro Asn
            500                 505                 510

Lys

<210> SEQ ID NO 59
<211> LENGTH: 513
<212> TYPE: PRT
<213> ORGANISM: Bacillus spec

<400> SEQUENCE: 59

Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
            20                  25                  30

Glu Glu Cys Thr His Gln Leu His Arg Asp Leu Pro Pro Thr Arg Leu
        35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Thr His
65                  70                  75                  80

Phe Leu Pro Ile Asp His Thr Ile His Ser Asp Ser Gln His Glu
                85                  90                  95

Glu Ser Glu Val Lys Thr Val Val His Leu His Gly Gly Val Thr Pro
            100                 105                 110

Asp Asp Ser Asp Gly Tyr Pro Glu Ala Trp Phe Ser Lys Asp Phe Glu
        115                 120                 125

Gln Thr Gly Pro Tyr Phe Lys Arg Glu Val Tyr His Tyr Pro Asn Gln
    130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Asp Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Ala Pro Glu Asn Pro Ser Pro Ser Leu Pro Asn Pro Ser Ile
    210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Glu
            260                 265                 270
```

```
Phe Ile Gln Ile Gly Ser Asp Gly Leu Leu Pro Arg Ser Val Lys
            275                 280                 285

Leu Asn Ser Phe Ser Leu Ala Pro Ala Glu Arg Tyr Asp Ile Ile Ile
    290                 295                 300

Asp Phe Thr Ala Tyr Glu Gly Glu Ser Ile Ile Leu Ala Asn Ser Ala
305                 310                 315                 320

Gly Cys Gly Gly Asp Val Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln His Glu Arg Ile Gln Asn
        355                 360                 365

Ile Arg Thr Leu Lys Leu Ala Gly Thr Gln Asp Glu Tyr Gly Arg Pro
    370                 375                 380

Val Leu Leu Leu Asn Asn Lys Arg Trp His Asp Pro Val Thr Glu Ala
385                 390                 395                 400

Pro Lys Val Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
            420                 425                 430

Arg Arg Pro Phe Asp Ile Ala Arg Tyr Gln Glu Ser Gly Glu Leu Ser
        435                 440                 445

Tyr Thr Gly Pro Ala Val Pro Pro Pro Ser Glu Lys Gly Trp Lys
    450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
            500                 505                 510

Lys

<210> SEQ ID NO 60
<211> LENGTH: 515
<212> TYPE: PRT
<213> ORGANISM: Bacillus spec

<400> SEQUENCE: 60

Met Lys Met Thr Leu Glu Lys Phe Val Asp Ala Leu Pro Ile Pro Asp
1               5                   10                  15

Thr Leu Lys Pro Val Gln Gln Ser Lys Glu Lys Thr Tyr Tyr Glu Val
            20                  25                  30

Thr Met Glu Glu Cys Thr His Gln Leu His Arg Asp Leu Pro Pro Thr
        35                  40                  45

Arg Leu Trp Gly Tyr Asn Gly Leu Phe Pro Gly Pro Thr Ile Glu Val
    50                  55                  60

Lys Arg Asn Glu Asn Val Tyr Val Lys Trp Met Asn Asn Leu Pro Ser
65                  70                  75                  80

Thr His Phe Leu Pro Ile Asp His Thr Ile His His Ser Asp Ser Gln
                85                  90                  95

His Glu Glu Ser Glu Val Lys Thr Val Val His Leu His Gly Gly Val
            100                 105                 110

Thr Pro Asp Asp Ser Asp Gly Tyr Pro Glu Ala Trp Phe Ser Lys Asp
        115                 120                 125
```

Phe Glu Gln Thr Gly Pro Tyr Phe Lys Arg Glu Val Tyr His Tyr Pro
130                 135                 140

Asn Gln Gln Arg Gly Ala Ile Leu Trp Tyr His Asp His Ala Met Ala
145                 150                 155                 160

Leu Thr Arg Leu Asn Val Tyr Ala Gly Leu Val Gly Ala Tyr Ile Ile
                165                 170                 175

His Asp Pro Lys Glu Lys Arg Leu Lys Leu Pro Ser Asp Glu Tyr Asp
            180                 185                 190

Val Pro Leu Leu Ile Thr Asp Arg Thr Ile Asn Glu Asp Gly Ser Leu
        195                 200                 205

Phe Tyr Pro Ser Ala Pro Glu Asn Pro Ser Pro Ser Leu Pro Asn Pro
210                 215                 220

Ser Ile Val Pro Ala Phe Cys Gly Glu Thr Ile Leu Val Asn Gly Lys
225                 230                 235                 240

Val Trp Pro Tyr Leu Glu Val Glu Pro Arg Lys Tyr Arg Phe Arg Val
                245                 250                 255

Ile Asn Ala Ser Asn Thr Arg Thr Tyr Asn Leu Ser Leu Asp Asn Gly
            260                 265                 270

Gly Glu Phe Ile Gln Ile Gly Ser Asp Gly Gly Leu Leu Pro Arg Ser
        275                 280                 285

Val Lys Leu Asn Ser Phe Ser Leu Ala Pro Ala Glu Arg Tyr Asp Ile
290                 295                 300

Ile Ile Asp Phe Thr Ala Tyr Glu Gly Glu Ser Ile Ile Leu Ala Asn
305                 310                 315                 320

Ser Ala Gly Cys Gly Gly Asp Val Asn Pro Glu Thr Asp Ala Asn Ile
                325                 330                 335

Met Gln Phe Arg Val Thr Lys Pro Leu Ala Gln Lys Asp Glu Ser Arg
            340                 345                 350

Lys Pro Lys Tyr Leu Ala Ser Tyr Pro Ser Val Gln His Glu Arg Ile
        355                 360                 365

Gln Asn Ile Arg Thr Leu Lys Leu Ala Gly Thr Gln Asp Glu Tyr Gly
370                 375                 380

Arg Pro Val Leu Leu Leu Asn Asn Lys Arg Trp His Asp Pro Val Thr
385                 390                 395                 400

Glu Ala Pro Lys Val Gly Thr Thr Glu Ile Trp Ser Ile Ile Asn Pro
                405                 410                 415

Thr Arg Gly Thr His Pro Ile His Leu His Leu Val Ser Phe Arg Val
            420                 425                 430

Leu Asp Arg Arg Pro Phe Asp Ile Ala Arg Tyr Gln Glu Ser Gly Glu
        435                 440                 445

Leu Ser Tyr Thr Gly Pro Ala Val Pro Pro Pro Ser Glu Lys Gly
450                 455                 460

Trp Lys Asp Thr Ile Gln Ala His Ala Gly Glu Val Leu Arg Ile Ala
465                 470                 475                 480

Ala Thr Phe Gly Pro Tyr Ser Gly Arg Tyr Val Trp His Cys His Ile
                485                 490                 495

Leu Glu His Glu Asp Tyr Asp Met Met Arg Pro Met Asp Ile Thr Asp
            500                 505                 510

Pro His Lys
        515

<210> SEQ ID NO 61
<211> LENGTH: 515
<212> TYPE: PRT

<213> ORGANISM: Bacillus spec

<400> SEQUENCE: 61

```
Met Lys Met Thr Leu Glu Lys Phe Val Asp Ala Leu Pro Ile Pro Asp
1               5                   10                  15

Thr Leu Lys Pro Val Gln Gln Ser Lys Glu Lys Thr Tyr Tyr Glu Val
            20                  25                  30

Thr Met Glu Glu Cys Thr His Gln Leu His Arg Asp Leu Pro Pro Thr
        35                  40                  45

Arg Leu Trp Gly Tyr Asn Gly Leu Phe Pro Gly Pro Thr Ile Glu Val
    50                  55                  60

Lys Arg Asn Glu Asn Val Tyr Val Lys Trp Met Asn Asn Leu Pro Ser
65                  70                  75                  80

Thr His Phe Leu Pro Ile Asp His Thr Ile His His Ser Asp Ser Gln
                85                  90                  95

His Glu Glu Pro Glu Val Lys Thr Val Val His Leu His Gly Gly Val
            100                 105                 110

Thr Pro Asp Asp Ser Asp Gly Tyr Pro Glu Ala Trp Phe Ser Lys Asp
        115                 120                 125

Phe Glu Gln Thr Gly Pro Tyr Phe Lys Arg Glu Val Tyr His Tyr Pro
    130                 135                 140

Asn Gln Gln Arg Gly Ala Ile Leu Trp Tyr His Asp His Ala Met Ala
145                 150                 155                 160

Leu Thr Arg Leu Asn Val Tyr Ala Gly Leu Val Gly Ala Tyr Ile Ile
                165                 170                 175

His Asp Pro Lys Glu Lys Arg Leu Lys Leu Pro Ser Asp Glu Tyr Asp
            180                 185                 190

Val Pro Leu Leu Ile Thr Asp Arg Thr Ile Asn Glu Asp Gly Ser Leu
        195                 200                 205

Phe Tyr Pro Ser Ala Pro Glu Asn Pro Ser Pro Ser Leu Pro Asn Pro
    210                 215                 220

Ser Ile Val Pro Ala Phe Cys Gly Glu Thr Ile Leu Val Asn Gly Lys
225                 230                 235                 240

Val Trp Pro Tyr Leu Glu Val Glu Pro Arg Lys Tyr Arg Phe Arg Val
                245                 250                 255

Ile Asn Ala Ser Asn Thr Arg Thr Tyr Asn Leu Ser Leu Asp Asn Gly
            260                 265                 270

Gly Asp Phe Ile Gln Ile Gly Ser Asp Gly Gly Leu Leu Pro Arg Ser
        275                 280                 285

Val Lys Leu Asn Ser Phe Ser Leu Ala Pro Ala Glu Arg Tyr Asp Ile
    290                 295                 300

Ile Ile Asp Phe Thr Ala Tyr Glu Gly Glu Ser Ile Ile Leu Ala Asn
305                 310                 315                 320

Ser Ala Gly Cys Gly Gly Asp Val Asn Pro Glu Thr Asp Ala Asn Ile
                325                 330                 335

Met Gln Phe Arg Val Thr Lys Pro Leu Ala Gln Lys Asp Glu Ser Arg
            340                 345                 350

Lys Pro Lys Tyr Leu Ala Ser Tyr Pro Ser Val Gln His Glu Arg Ile
        355                 360                 365

Gln Asn Ile Arg Thr Leu Lys Leu Ala Gly Thr Gln Asp Glu Tyr Gly
    370                 375                 380

Arg Pro Val Leu Leu Leu Asn Asn Lys Arg Trp His Asp Pro Val Thr
385                 390                 395                 400
```

```
Glu Thr Pro Lys Val Gly Thr Thr Glu Ile Trp Ser Ile Ile Asn Pro
                405                 410                 415

Thr Arg Gly Thr His Pro Ile His Leu His Leu Val Ser Phe Arg Val
            420                 425                 430

Leu Asp Arg Arg Pro Phe Asp Ile Ala Arg Tyr Gln Glu Ser Gly Glu
        435                 440                 445

Leu Ser Tyr Thr Gly Pro Ala Val Pro Pro Pro Ser Glu Lys Gly
    450                 455                 460

Trp Lys Asp Thr Ile Gln Ala His Ala Gly Glu Val Leu Arg Ile Ala
465                 470                 475                 480

Ala Thr Phe Gly Pro Tyr Ser Gly Arg Tyr Val Trp His Cys His Ile
                485                 490                 495

Leu Glu His Glu Asp Tyr Asp Met Met Arg Pro Met Asp Ile Thr Asp
                500                 505                 510

Pro His Lys
        515

<210> SEQ ID NO 62
<211> LENGTH: 513
<212> TYPE: PRT
<213> ORGANISM: Bacillus spec

<400> SEQUENCE: 62

Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
                20                  25                  30

Glu Glu Cys Thr His Gln Leu His Arg Asp Leu Pro Pro Thr Arg Leu
            35                  40                  45

Trp Gly Tyr Asn Gly Leu Phe Pro Gly Pro Thr Ile Glu Val Lys Arg
        50                  55                  60

Asn Glu Asn Val Tyr Val Lys Trp Met Asn Asn Leu Pro Ser Thr His
65                  70                  75                  80

Phe Leu Pro Ile Asp His Thr Ile His His Ser Asp Ser Gln His Glu
                85                  90                  95

Glu Pro Glu Val Lys Thr Val Val His Leu His Gly Gly Val Thr Pro
                100                 105                 110

Asp Asp Ser Asp Gly Tyr Pro Glu Ala Trp Phe Ser Lys Asp Phe Glu
            115                 120                 125

Gln Thr Gly Pro Tyr Phe Lys Arg Glu Val Tyr His Tyr Pro Asn Gln
        130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Asp Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Ala Pro Glu Asn Pro Ser Pro Ser Leu Pro Asn Pro Ser Ile
    210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255
```

```
Ala Ser Asn Thr Arg Thr Tyr Asn Leu Ser Leu Asp Asn Gly Gly Asp
            260                 265                 270

Phe Ile Gln Ile Gly Ser Asp Gly Leu Leu Pro Arg Ser Val Lys
        275                 280                 285

Leu Asn Ser Phe Ser Leu Ala Pro Ala Glu Arg Tyr Asp Ile Ile Ile
    290                 295                 300

Asp Phe Thr Ala Tyr Glu Gly Glu Ser Ile Ile Leu Ala Asn Ser Ala
305                 310                 315                 320

Gly Cys Gly Gly Asp Val Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln His Glu Arg Ile Gln Asn
        355                 360                 365

Ile Arg Thr Leu Lys Leu Ala Gly Thr Gln Asp Glu Tyr Gly Arg Pro
    370                 375                 380

Val Leu Leu Leu Asn Asn Lys Arg Trp His Asp Pro Val Thr Glu Thr
385                 390                 395                 400

Pro Lys Val Gly Thr Thr Glu Ile Trp Ser Ile Asn Pro Thr Arg
            405                 410                 415

Gly Thr His Pro Ile His Leu His Leu Val Ser Phe Arg Val Leu Asp
        420                 425                 430

Arg Arg Pro Phe Asp Ile Ala Arg Tyr Gln Glu Ser Gly Glu Leu Ser
    435                 440                 445

Tyr Thr Gly Pro Ala Val Pro Pro Pro Ser Glu Lys Gly Trp Lys
            450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
            485                 490                 495

His Glu Asp Tyr Asp Met Met Arg Pro Met Asp Ile Thr Asp Pro His
                500                 505                 510

Lys

<210> SEQ ID NO 63
<211> LENGTH: 513
<212> TYPE: PRT
<213> ORGANISM: Bacillus spec

<400> SEQUENCE: 63

Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
            20                  25                  30

Glu Glu Cys Thr His Gln Leu His Arg Asp Leu Leu Pro Thr Arg Leu
        35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Thr His
65                  70                  75                  80

Phe Leu Pro Ile Asp His Thr Ile His His Ser Asp Ser Gln His Glu
            85                  90                  95

Glu Pro Glu Val Lys Thr Val Val His Leu His Gly Gly Val Thr Pro
            100                 105                 110
```

```
Asp Asp Ser Asp Gly Tyr Pro Glu Ala Trp Phe Ser Lys Asp Phe Glu
        115                 120                 125
Gln Thr Gly Pro Tyr Phe Lys Arg Glu Val Tyr His Tyr Pro Asn Gln
        130                 135                 140
Gln Arg Gly Ala Ile Leu Trp Tyr His Asp His Ala Met Ala Leu Thr
145                 150                 155                 160
Arg Leu Asn Val Tyr Ala Gly Leu Val Gly Ala Tyr Ile Ile His Asp
                165                 170                 175
Pro Lys Glu Lys Arg Leu Lys Leu Pro Ser Asp Glu Tyr Asp Val Pro
                180                 185                 190
Leu Leu Ile Thr Asp Arg Thr Ile Asn Glu Asp Gly Ser Leu Phe Tyr
                195                 200                 205
Pro Ser Ala Pro Glu Asn Pro Ser Pro Ser Leu Pro Asn Pro Ser Ile
        210                 215                 220
Val Pro Ala Phe Cys Gly Glu Thr Ile Leu Val Asn Gly Lys Val Trp
225                 230                 235                 240
Pro Tyr Leu Glu Val Glu Pro Arg Lys Tyr Arg Phe Arg Val Ile Asn
                245                 250                 255
Ala Ser Asn Thr Arg Thr Tyr Asn Leu Ser Leu Asp Asn Gly Gly Glu
                260                 265                 270
Phe Ile Gln Ile Gly Ala Asp Gly Gly Leu Leu Pro Arg Ser Val Lys
                275                 280                 285
Leu Asn Ser Phe Ser Leu Ala Pro Ala Glu Arg Tyr Asp Ile Ile Ile
        290                 295                 300
Asp Phe Thr Ala Tyr Glu Gly Glu Ser Ile Ile Leu Ala Asn Ser Ala
305                 310                 315                 320
Gly Cys Gly Gly Asp Val Asn Pro Glu Thr Asp Ala Asn Ile Met Gln
                325                 330                 335
Phe Arg Val Thr Lys Pro Leu Ala Gln Lys Asp Glu Ser Arg Lys Pro
                340                 345                 350
Lys Tyr Leu Ala Ser Tyr Pro Ser Val Gln His Glu Arg Ile Gln Asn
        355                 360                 365
Ile Arg Thr Leu Lys Leu Ala Gly Thr Gln Asp Glu Tyr Gly Arg Pro
        370                 375                 380
Val Leu Leu Leu Asn Asn Lys Arg Trp His Asp Pro Val Thr Glu Ala
385                 390                 395                 400
Pro Lys Val Gly Thr Thr Glu Ile Trp Ser Ile Ile Asn Pro Thr Arg
                405                 410                 415
Gly Thr His Pro Ile His Leu His Leu Val Ser Phe Arg Val Leu Asp
                420                 425                 430
Arg Arg Pro Phe Asp Ile Ala Arg Tyr Gln Glu Ser Gly Glu Leu Ser
        435                 440                 445
Tyr Thr Gly Pro Ala Val Pro Pro Pro Ser Glu Lys Gly Trp Lys
        450                 455                 460
Asp Thr Ile Gln Ala His Ala Gly Glu Val Leu Arg Ile Ala Ala Thr
465                 470                 475                 480
Phe Gly Pro Tyr Ser Gly Arg Tyr Val Trp His Cys His Ile Leu Glu
                485                 490                 495
His Glu Asp Tyr Asp Met Met Arg Pro Met Asp Ile Thr Asp Pro His
                500                 505                 510
Lys
```

```
<210> SEQ ID NO 64
<211> LENGTH: 513
<212> TYPE: PRT
<213> ORGANISM: Bacillus spec

<400> SEQUENCE: 64

Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
            20                  25                  30

Glu Glu Cys Thr His Gln Leu His Arg Asp Leu Pro Pro Thr Arg Leu
        35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Thr His
65                  70                  75                  80

Phe Leu Pro Ile Asp His Thr Ile His His Ser Asp Ser Gln His Glu
                85                  90                  95

Glu Pro Glu Val Lys Thr Val Val His Leu His Gly Val Thr Pro
            100                 105                 110

Asp Asp Ser Asp Gly Tyr Pro Glu Ala Trp Phe Ser Lys Asp Phe Glu
            115                 120                 125

Gln Thr Gly Pro Tyr Phe Lys Arg Glu Val Tyr His Tyr Pro Asn Gln
        130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Asp Glu Tyr Asp Val Pro
            180                 185                 190

Leu Leu Ile Thr Asp Arg Thr Ile Asn Glu Asp Gly Ser Leu Phe Tyr
            195                 200                 205

Pro Ser Ala Pro Glu Asn Pro Ser Pro Ser Leu Pro Asn Pro Ser Ile
        210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Asp
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Tyr Asp Ile Ile Ile
    290                 295                 300

Asp Phe Thr Ala Tyr Glu Gly Glu Ser Ile Ile Leu Ala Asn Ser Ala
305                 310                 315                 320

Gly Cys Gly Gly Asp Val Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln His Glu Arg Ile Gln Asn
        355                 360                 365

Ile Arg Thr Leu Lys Leu Ala Gly Thr Gln Asp Glu Tyr Gly Arg Pro
    370                 375                 380
```

```
Val Leu Leu Asn Asn Lys Arg Trp His Asp Pro Val Thr Glu Thr
385                 390                 395                 400

Pro Lys Val Gly Thr Thr Glu Ile Trp Ser Ile Ile Asn Pro Thr Arg
            405                 410                 415

Gly Thr His Pro Ile His Leu His Leu Val Ser Phe Arg Val Leu Asp
                420                 425                 430

Arg Arg Pro Phe Asp Ile Ala Arg Tyr Gln Glu Ser Gly Glu Leu Ser
            435                 440                 445

Tyr Thr Gly Pro Ala Val Pro Pro Pro Ser Glu Lys Gly Trp Lys
    450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Asp Asp Tyr Asp Met Met Arg Pro Met Asp Ile Thr Asp Pro His
                500                 505                 510

Lys

<210> SEQ ID NO 65
<211> LENGTH: 513
<212> TYPE: PRT
<213> ORGANISM: Bacillus spec

<400> SEQUENCE: 65

Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
            20                  25                  30

Glu Glu Cys Thr His Gln Leu His Arg Asp Leu Pro Pro Thr Arg Leu
        35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Thr His
65                  70                  75                  80

Phe Leu Pro Ile Asp His Thr Ile His His Ser Asp Ser Gln His Glu
                85                  90                  95

Glu Pro Glu Val Lys Thr Val Val His Leu His Gly Gly Val Thr Pro
            100                 105                 110

Asp Asp Ser Asn Gly Tyr Pro Glu Ala Trp Phe Ser Lys Asp Phe Glu
        115                 120                 125

Gln Thr Gly Pro Tyr Phe Lys Arg Glu Val Tyr His Tyr Pro Asn Gln
    130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Asp Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Ala Pro Glu Asn Pro Ser Pro Ser Leu Pro Asn Pro Ser Ile
    210                 215                 220

Val Pro Ala Phe Cys Gly Glu Thr Ile Leu Val Asn Gly Lys Val Trp
225                 230                 235                 240
```

```
Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Asp
            260                 265                 270

Phe Ile Gln Ile Gly Ser Asp Gly Leu Leu Pro Arg Ser Val Lys
        275                 280                 285

Leu Asn Ser Phe Ser Leu Ala Pro Ala Glu Arg Tyr Asp Ile Ile Ile
    290                 295                 300

Asp Phe Thr Ala Tyr Glu Gly Glu Ser Ile Ile Leu Ala Asn Ser Ala
305                 310                 315                 320

Gly Cys Gly Gly Asp Val Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln His Glu Arg Ile Gln Asn
        355                 360                 365

Ile Arg Thr Leu Lys Leu Ala Gly Thr Gln Asp Glu Tyr Gly Arg Pro
    370                 375                 380

Val Leu Leu Leu Asn Asn Lys Arg Trp His Asp Pro Val Thr Glu Thr
385                 390                 395                 400

Pro Lys Val Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
            420                 425                 430

Arg Arg Pro Phe Asp Ile Ala Arg Tyr Gln Glu Ser Gly Glu Leu Ser
        435                 440                 445

Tyr Thr Gly Pro Ala Val Pro Pro Pro Ser Glu Lys Gly Trp Lys
    450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
            500                 505                 510

Lys

<210> SEQ ID NO 66
<211> LENGTH: 513
<212> TYPE: PRT
<213> ORGANISM: Bacillus spec

<400> SEQUENCE: 66

Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
                20                  25                  30

Glu Glu Cys Thr His Gln Leu His Arg Asp Leu Pro Pro Thr Arg Leu
            35                  40                  45

Trp Gly Tyr Asn Gly Leu Phe Pro Gly Pro Thr Ile Glu Val Lys Arg
        50                  55                  60

Asn Glu Asn Val Tyr Val Lys Trp Met Asn Asn Leu Pro Ser Thr His
65                  70                  75                  80

Phe Leu Pro Ile Asp His Thr Ile His His Ser Asp Ser Gln His Glu
                85                  90                  95
```

```
Glu Pro Glu Val Lys Thr Val Val His Leu His Gly Gly Val Thr Pro
                100                 105                 110

Asp Asp Ser Ala Gly Tyr Pro Glu Ala Trp Phe Ser Lys Asp Phe Glu
            115                 120                 125

Gln Thr Gly Pro Tyr Phe Lys Arg Glu Val Tyr His Tyr Pro Asn Gln
        130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Asp Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Ala Pro Glu Asn Pro Ser Pro Ser Leu Pro Asn Pro Ser Ile
210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Asp
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Tyr Asp Ile Ile Ile
        290                 295                 300

Asp Phe Thr Ala Tyr Glu Gly Glu Ser Ile Ile Leu Ala Asn Ser Ala
305                 310                 315                 320

Gly Cys Gly Gly Asp Val Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln His Glu Arg Ile Gln Asn
        355                 360                 365

Ile Arg Thr Leu Lys Leu Ala Gly Thr Gln Asp Glu Tyr Gly Arg Pro
        370                 375                 380

Val Leu Leu Leu Asn Asn Lys Arg Trp His Asp Pro Val Thr Glu Thr
385                 390                 395                 400

Pro Lys Val Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
            420                 425                 430

Arg Arg Pro Phe Asp Ile Ala Arg Tyr Gln Glu Ser Gly Glu Leu Ser
        435                 440                 445

Tyr Thr Gly Pro Ala Val Pro Pro Ser Glu Lys Gly Trp Lys
        450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
            500                 505                 510

Lys
```

<210> SEQ ID NO 67
<211> LENGTH: 513
<212> TYPE: PRT
<213> ORGANISM: Bacillus spec

<400> SEQUENCE: 67

```
Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
            20                  25                  30

Glu Glu Cys Thr His Gln Leu His Arg Asp Leu Pro Pro Thr Arg Leu
        35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Thr Arg
65                  70                  75                  80

Phe Leu Pro Ile Asp His Thr Ile His His Ser Asp Ser Gln His Glu
                85                  90                  95

Glu Pro Glu Val Lys Thr Val His Leu His Gly Gly Val Thr Pro
            100                 105                 110

Asp Asp Ser Asp Gly Tyr Pro Glu Ala Trp Phe Ser Lys Asp Phe Glu
        115                 120                 125

Gln Thr Gly Pro Tyr Phe Lys Arg Glu Val Tyr His Tyr Pro Asn Gln
    130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Asp Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Ala Pro Glu Asn Pro Ser Pro Ser Leu Pro Asn Pro Ser Ile
    210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Glu
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Tyr Asp Ile Ile Ile
    290                 295                 300

Asp Phe Thr Ala Tyr Glu Gly Glu Ser Ile Ile Leu Ala Asn Ser Ala
305                 310                 315                 320

Gly Cys Gly Gly Asp Val Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln His Glu Arg Ile Gln Asn
        355                 360                 365

Ile Arg Thr Leu Lys Leu Ala Gly Thr Gln Gly Glu Tyr Gly Arg Pro
```

```
            370                 375                 380
Val Leu Leu Leu Asn Asn Lys Arg Trp His Asp Pro Val Thr Glu Ala
385                 390                 395                 400

Pro Lys Val Gly Thr Ala Glu Ile Trp Ser Ile Ile Asn Pro Thr Arg
                405                 410                 415

Gly Thr His Pro Ile His Leu His Leu Val Ser Phe Arg Val Leu Asp
                420                 425                 430

Arg Arg Pro Phe Asp Ile Ala Arg Tyr Gln Glu Ser Gly Glu Leu Ser
            435                 440                 445

Tyr Thr Gly Pro Ala Val Pro Pro Pro Ser Glu Lys Gly Trp Lys
450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
                500                 505                 510

Lys

<210> SEQ ID NO 68
<211> LENGTH: 513
<212> TYPE: PRT
<213> ORGANISM: Bacillus spec

<400> SEQUENCE: 68

Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
            20                  25                  30

Glu Glu Cys Ala His Gln Leu His Arg Asp Leu Pro Pro Thr Arg Leu
        35                  40                  45

Trp Gly Tyr Asn Gly Glu Phe Pro Gly Pro Thr Ile Glu Val Lys Arg
    50                  55                  60

Asn Glu Asn Val Tyr Val Lys Trp Met Asn Asn Leu Pro Ser Glu His
65                  70                  75                  80

Phe Leu Pro Ile Asp His Thr Ile His His Ser Asp Ser Gln His Glu
                85                  90                  95

Glu Pro Glu Val Arg Thr Val Val His Leu His Gly Gly Val Thr Pro
            100                 105                 110

Asp Asp Ser Asp Gly Tyr Pro Glu Ala Trp Phe Ser Lys Asp Leu Glu
        115                 120                 125

Gln Thr Gly Pro Tyr Phe Lys Arg Glu Val Tyr His Tyr Pro Asn Gln
    130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Gly Val Tyr Gly Val Pro
        180                 185                 190

Leu Leu Ile Thr Asp Arg Thr Ile Asn Glu Asp Gly Ser Leu Phe Tyr
    195                 200                 205

Pro Ser Gly Pro Glu Asn Pro Ser Pro Ser Leu Pro Asn Pro Ser Ile
210                 215                 220

Val Pro Ala Phe Cys Gly Glu Thr Ile Leu Val Asn Gly Lys Ala Trp
```

-continued

```
                225                 230                 235                 240
        Pro Tyr Phe Glu Val Glu Pro Arg Lys Tyr Arg Phe Arg Val Ile Asn
                        245                 250                 255

Ala Ser Asn Thr Arg Thr Tyr Asn Leu Ser Leu Asp Asn Gly Gly Ala
                    260                 265                 270

Phe Ile Gln Ile Gly Ser Asp Gly Gly Leu Leu Pro Arg Ser Val Lys
                    275                 280                 285

Leu Asn Ser Phe Ser Leu Ala Pro Ala Glu Arg Tyr Asp Ile Ile Ile
                290                 295                 300

Asp Phe Thr Ala Tyr Glu Gly Gln Ser Ile Thr Leu Ala Asn Asn Glu
        305                 310                 315                 320

Gly Cys Gly Gly Gly Val Asn Pro Glu Thr Asp Ala Asn Ile Met Gln
                        325                 330                 335

Phe Arg Val Thr Lys Pro Leu Ala Gln Lys Asp Glu Ser Arg Lys Pro
                        340                 345                 350

Lys Tyr Leu Ala Ser Tyr Pro Ser Val Gln Asn Glu Lys Ile Gln Asn
                    355                 360                 365

Ile Arg Thr Leu Lys Leu Ala Gly Thr Gln Asp Glu Tyr Gly Arg Pro
                    370                 375                 380

Val Leu Leu Asn Asn Lys Arg Trp His Asp Pro Val Thr Asp Ala
        385                 390                 395                 400

Pro Lys Ala Gly Thr Thr Glu Ile Trp Ser Ile Val Asn Pro Thr Arg
                        405                 410                 415

Gly Thr His Pro Ile His Leu His Leu Val Ser Phe Arg Val Leu Asp
                        420                 425                 430

Arg Arg Pro Phe Asp Ile Ala Arg Tyr Gln Glu Arg Gly Glu Leu Ser
                        435                 440                 445

Tyr Thr Gly Pro Ala Val Pro Pro Pro Ser Glu Lys Gly Trp Lys
                    450                 455                 460

Asp Thr Ile Gln Ala His Ala Gly Glu Val Leu Arg Ile Ala Val Thr
        465                 470                 475                 480

Phe Gly Pro Tyr Ser Gly Arg Tyr Val Trp His Cys His Ile Leu Glu
                        485                 490                 495

His Glu Asp Tyr Asp Met Met Arg Pro Met Asp Ile Thr Asp Pro His
                    500                 505                 510

Lys
```

<210> SEQ ID NO 69
<211> LENGTH: 513
<212> TYPE: PRT
<213> ORGANISM: Bacillus spec
<220> FEATURE:
<221> NAME/KEY: misc_feature
<222> LOCATION: (35)..(35)
<223> OTHER INFORMATION: Xaa can be any naturally occurring amino acid

<400> SEQUENCE: 69

```
Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
                20                  25                  30

Glu Glu Xaa Thr His Gln Leu His Arg Asp Leu Pro Pro Thr Arg Leu
            35                  40                  45

Trp Gly Tyr Asn Gly Leu Phe Pro Gly Pro Thr Ile Glu Val Lys Arg
        50                  55                  60
```

-continued

Asn Glu Asn Val Tyr Val Lys Trp Met Asn Asn Leu Pro Ser Thr His
 65                  70                  75                  80

Phe Leu Pro Ile Asp His Thr Ile His His Ser Asp Ser Gln His Glu
             85                  90                  95

Glu Pro Glu Val Lys Thr Val Val His Leu His Gly Val Thr Pro
            100                 105                 110

Asp Asp Ser Asp Gly Tyr Pro Glu Ala Trp Phe Ser Lys Asp Phe Glu
        115                 120                 125

Gln Thr Gly Pro Tyr Phe Lys Arg Glu Val Tyr Tyr Pro Asn Gln
        130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Asp Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Ala Pro Glu Asn Pro Ser Pro Ser Leu Pro Asn Pro Ser Ile
210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Asp
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Tyr Asp Ile Ile Ile
        290                 295                 300

Asp Phe Thr Ala Tyr Glu Gly Glu Ser Ile Ile Leu Ala Asn Ser Ala
305                 310                 315                 320

Gly Cys Gly Gly Asp Val Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln His Glu Arg Ile Gln Asn
        355                 360                 365

Ile Arg Thr Leu Lys Leu Ala Gly Thr Gln Asp Glu Tyr Gly Arg Pro
        370                 375                 380

Val Leu Leu Leu Asn Asn Lys Arg Trp His Asp Pro Val Thr Glu Thr
385                 390                 395                 400

Pro Lys Val Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
            420                 425                 430

Arg Arg Pro Phe Asp Ile Ala Arg Tyr Gln Glu Ser Gly Glu Leu Ser
        435                 440                 445

Tyr Thr Gly Pro Ala Val Pro Pro Pro Ser Glu Lys Gly Trp Lys
        450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu

```
                      485                 490                 495
His Glu Asp Tyr Asp Met Met Arg Pro Met Asp Ile Thr Asp Pro His
                500                 505                 510

Lys

<210> SEQ ID NO 70
<211> LENGTH: 513
<212> TYPE: PRT
<213> ORGANISM: Bacillus spec

<400> SEQUENCE: 70

Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
                20                  25                  30

Glu Glu Cys Thr His Gln Leu His Arg Asp Leu Pro Pro Thr Arg Leu
            35                  40                  45

Trp Gly Tyr Asn Gly Leu Phe Pro Gly Pro Thr Ile Glu Val Lys Arg
        50                  55                  60

Asn Glu Asn Val Tyr Val Lys Trp Met Asn Asn Leu Pro Ser Thr His
65                  70                  75                  80

Phe Leu Pro Ile Asp His Thr Ile His His Ser Asp Ser Gln His Glu
                85                  90                  95

Glu Pro Glu Val Lys Thr Val Val His Leu His Gly Val Thr Pro
            100                 105                 110

Asp Asp Ser Asp Gly Tyr Pro Glu Ala Trp Phe Ser Lys Asp Phe Glu
        115                 120                 125

Gln Thr Gly Pro Tyr Phe Lys Arg Glu Val Tyr His Tyr Pro Asn Gln
    130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Asp Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Ala Pro Glu Asn Pro Ser Pro Ser Leu Pro Asn Pro Ser Ile
    210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Asp
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Cys Asp Ile Ile Ile
    290                 295                 300

Asp Phe Thr Ala Tyr Glu Gly Glu Ser Ile Ile Leu Ala Asn Ser Ala
305                 310                 315                 320

Gly Cys Gly Gly Asp Val Asn Pro Glu Thr Asp Ala Asn Ile Met Gln
                325                 330                 335

Phe Arg Val Thr Lys Pro Leu Ala Gln Lys Asp Glu Ser Arg Lys Pro
```

```
                340                 345                 350
Lys Tyr Leu Ala Ser Tyr Pro Ser Val Gln His Glu Arg Ile Gln Asn
                355                 360                 365

Ile Arg Thr Leu Lys Leu Ala Gly Thr Gln Asp Glu Tyr Gly Arg Pro
        370                 375                 380

Val Leu Leu Asn Asn Lys Arg Trp His Asp Pro Val Thr Glu Thr
385                 390                 395                 400

Pro Lys Val Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
                420                 425                 430

Arg Arg Pro Phe Asp Ile Ala Arg Tyr Gln Glu Ser Gly Glu Leu Ser
            435                 440                 445

Tyr Thr Gly Thr Ala Val Pro Pro Pro Ser Glu Lys Gly Trp Lys
        450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
                500                 505                 510

Lys
```

<210> SEQ ID NO 71
<211> LENGTH: 513
<212> TYPE: PRT
<213> ORGANISM: Bacillus spec
<220> FEATURE:
<221> NAME/KEY: misc_feature
<222> LOCATION: (35)..(35)
<223> OTHER INFORMATION: Xaa can be any naturally occurring amino acid

<400> SEQUENCE: 71

```
Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
                20                  25                  30

Glu Glu Xaa Thr His Gln Leu His Arg Asp Leu Pro Pro Thr Arg Leu
            35                  40                  45

Trp Gly Tyr Asn Gly Leu Phe Pro Gly Pro Thr Ile Glu Val Lys Arg
        50                  55                  60

Asn Glu Asn Val Tyr Val Lys Trp Met Asn Asn Leu Pro Ser Thr His
65                  70                  75                  80

Phe Leu Pro Ile Asp His Thr Ile His His Ser Asp Ser Gln His Glu
                85                  90                  95

Glu Pro Glu Val Lys Thr Val Val His Leu His Gly Gly Val Thr Pro
                100                 105                 110

Asp Asp Ser Glu Gly Tyr Pro Glu Ala Trp Phe Ser Lys Asp Phe Glu
            115                 120                 125

Gln Thr Gly Pro Tyr Phe Lys Arg Glu Val Tyr His Tyr Pro Asn Gln
        130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175
```

```
Pro Lys Glu Lys Arg Leu Lys Leu Pro Ser Asp Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Ala Pro Glu Asn Pro Ser Pro Ser Leu Pro Asn Pro Ser Ile
    210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Asp
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Tyr Asp Ile Ile Ile
    290                 295                 300

Asp Phe Thr Ala Tyr Glu Gly Glu Ser Ile Ile Leu Ala Asn Ser Ala
305                 310                 315                 320

Gly Cys Gly Gly Asp Val Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln His Glu Arg Ile Gln Asn
        355                 360                 365

Ile Arg Thr Leu Lys Leu Ala Gly Thr Gln Asp Glu Tyr Gly Arg Pro
    370                 375                 380

Val Leu Leu Leu Asn Asn Lys Arg Trp His Asp Pro Val Thr Glu Thr
385                 390                 395                 400

Pro Lys Val Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
            420                 425                 430

Arg Arg Pro Phe Asp Ile Ala Arg Tyr Gln Glu Ser Gly Glu Leu Ser
        435                 440                 445

Tyr Thr Gly Pro Ala Val Pro Pro Pro Ser Glu Lys Gly Trp Lys
    450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
            500                 505                 510

Lys

<210> SEQ ID NO 72
<211> LENGTH: 513
<212> TYPE: PRT
<213> ORGANISM: Bacillus spec
<220> FEATURE:
<221> NAME/KEY: misc_feature
<222> LOCATION: (35)..(35)
<223> OTHER INFORMATION: Xaa can be any naturally occurring amino acid

<400> SEQUENCE: 72

Met Thr Leu Glu Lys Phe Val Asp Ala Leu Pro Ile Pro Asp Thr Leu
1               5                   10                  15
```

```
Lys Pro Val Gln Gln Ser Lys Glu Lys Thr Tyr Tyr Glu Val Thr Met
                 20                  25                  30

Glu Glu Xaa Thr His Gln Leu His Arg Asp Leu Pro Pro Thr Arg Leu
             35                  40                  45

Trp Gly Tyr Asn Gly Leu Phe Pro Gly Pro Thr Ile Glu Val Lys Arg
 50                  55                  60

Asn Glu Asn Val Tyr Val Lys Trp Met Asn Asn Leu Pro Ser Thr His
 65                  70                  75                  80

Phe Leu Pro Ile Asp His Thr Ile His His Ser Asp Ser Gln His Glu
                 85                  90                  95

Glu Pro Glu Val Lys Thr Val Val His Leu His Gly Gly Val Thr Pro
                100                 105                 110

Asp Asp Ser Asp Gly Tyr Pro Glu Ala Trp Phe Ser Lys Asp Phe Glu
            115                 120                 125

Gln Thr Gly Pro Tyr Phe Lys Arg Glu Val Tyr His Tyr Pro Asn Gln
130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Asp Glu Tyr Asp Val Pro
            180                 185                 190

Leu Leu Ile Thr Asp Arg Thr Ile Asn Glu Asp Gly Ser Leu Phe Tyr
            195                 200                 205

Pro Ser Ala Pro Glu Asn Pro Ser Pro Ser Leu Pro Asn Pro Ser Ile
    210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Asp
                260                 265                 270

Phe Ile Gln Ile Gly Ser Asp Gly Gly Leu Leu Pro Arg Ser Val Lys
                275                 280                 285

Leu Asn Ser Phe Ser Leu Ala Pro Ala Glu Arg Tyr Asp Ile Ile Ile
    290                 295                 300

Asp Phe Thr Ala Tyr Glu Gly Glu Ser Ile Ile Leu Ala Asn Ser Ala
305                 310                 315                 320

Gly Cys Gly Gly Asp Val Asn Pro Glu Thr Asp Ala Asn Ile Met Gln
                325                 330                 335

Phe Arg Val Thr Lys Pro Leu Ala Gln Lys Asp Glu Ser Arg Lys Pro
                340                 345                 350

Lys Tyr Leu Ala Ser Tyr Pro Ser Val Gln His Glu Arg Ile Gln Asn
                355                 360                 365

Ile Arg Thr Leu Lys Leu Ala Gly Thr Gln Asp Glu Tyr Gly Arg Pro
                370                 375                 380

Val Leu Leu Leu Asn Asn Lys Arg Trp His Asp Pro Val Thr Glu Thr
385                 390                 395                 400

Pro Lys Val Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
                420                 425                 430
```

```
Arg Arg Pro Phe Asp Ile Ala Arg Tyr Gln Glu Ser Gly Glu Leu Ser
            435                 440                 445

Tyr Thr Gly Pro Ala Val Pro Pro Pro Ser Glu Lys Gly Trp Lys
450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ala Leu Glu
                485                 490                 495

His Glu Asp Tyr Asp Met Met Arg Pro Met Asp Ile Thr Asp Pro His
            500                 505                 510

Lys

<210> SEQ ID NO 73
<211> LENGTH: 513
<212> TYPE: PRT
<213> ORGANISM: Bacillus spec
<220> FEATURE:
<221> NAME/KEY: misc_feature
<222> LOCATION: (35)..(35)
<223> OTHER INFORMATION: Xaa can be any naturally occurring amino acid

<400> SEQUENCE: 73

Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
            20                  25                  30

Glu Glu Xaa Thr His Gln Leu His Arg Asp Leu Pro Pro Thr Arg Leu
            35                  40                  45

Trp Gly Tyr Asn Gly Leu Phe Pro Gly Pro Thr Ile Glu Val Lys Arg
50                  55                  60

Asn Glu Asn Val Tyr Val Lys Trp Met Asn Asn Leu Pro Ser Thr His
65                  70                  75                  80

Phe Leu Pro Ile Asp His Thr Ile His His Ser Asp Ser Gln His Glu
                85                  90                  95

Glu Pro Glu Val Lys Thr Val Val His Leu His Gly Gly Val Thr Pro
            100                 105                 110

Asp Asp Ser Asp Gly Tyr Pro Glu Ala Trp Phe Ser Lys Asp Phe Glu
            115                 120                 125

Gln Thr Gly Pro Tyr Phe Lys Arg Glu Val Tyr His Tyr Pro Asn Gln
130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Asp Glu Tyr Asp Val Pro
            180                 185                 190

Leu Leu Ile Thr Asp Arg Thr Ile Asn Glu Asp Gly Ser Leu Phe Tyr
            195                 200                 205

Pro Ser Ala Pro Glu Asn Pro Ser Pro Ser Leu Pro Asn Pro Ser Ile
210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Asp
            260                 265                 270
```

```
Phe Ile Gln Ile Gly Ser Asp Gly Gly Leu Pro Arg Ser Val Lys
            275                 280                 285

Leu Asn Ser Phe Ser Leu Ala Pro Ala Glu Arg Tyr Asp Ile Ile Ile
    290                 295                 300

Asp Phe Thr Ala Tyr Glu Gly Glu Ser Ile Ile Leu Ala Asn Ser Ala
305                 310                 315                 320

Gly Cys Gly Gly Asp Val Asn Pro Glu Thr Asp Ala Asn Ile Met Gln
                325                 330                 335

Phe Arg Val Thr Lys Pro Leu Ala Gln Lys Asp Glu Ser Arg Lys Pro
                340                 345                 350

Lys Tyr Leu Ala Ser Tyr Pro Ser Val Gln His Glu Arg Ile Gln Asn
            355                 360                 365

Ile Arg Thr Leu Lys Leu Ala Gly Thr Gln Asp Glu Tyr Gly Arg Pro
    370                 375                 380

Val Leu Leu Leu Asn Asn Lys Arg Trp His Asp Pro Val Thr Glu Thr
385                 390                 395                 400

Pro Lys Val Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
                420                 425                 430

Arg Arg Pro Phe Asp Ile Ala Arg Tyr Gln Glu Ser Gly Glu Leu Ser
            435                 440                 445

Tyr Thr Gly Pro Ala Val Pro Pro Pro Ser Glu Lys Gly Trp Lys
    450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Thr Asp Tyr Asp Met Met Arg Pro Met Asp Ile Thr Asp Pro His
                500                 505                 510

Lys

<210> SEQ ID NO 74
<211> LENGTH: 513
<212> TYPE: PRT
<213> ORGANISM: Bacillus spec

<400> SEQUENCE: 74

Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
            20                  25                  30

Glu Glu Cys Thr His Gln Leu His Arg Asp Leu Pro Pro Thr Arg Leu
        35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Thr His
65                  70                  75                  80

Phe Leu Pro Ile Asp His Thr Ile His His Ser Asp Ser Gln His Glu
                85                  90                  95

Glu Ser Glu Val Lys Thr Val Val His Leu His Gly Gly Val Thr Pro
            100                 105                 110

Asp Asp Ser Asp Gly Tyr Pro Glu Ala Trp Phe Ser Lys Asp Phe Glu
        115                 120                 125
```

Gln Thr Gly Pro Tyr Phe Lys Arg Glu Val Tyr His Tyr Pro Asn Gln
                130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Asp Glu Tyr Asp Val Pro
                180                 185                 190

Leu Leu Ile Thr Asp Arg Thr Ile Asn Glu Asp Gly Ser Leu Phe Tyr
                195                 200                 205

Pro Ser Ala Pro Glu Asn Pro Ser Pro Ser Leu Pro Asn Pro Ser Ile
210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Glu
                260                 265                 270

Phe Ile Gln Val Gly Ser Asp Gly Gly Leu Leu Pro Arg Ser Val Lys
                275                 280                 285

Leu Asn Ser Phe Ser Leu Ala Pro Ala Glu Arg Tyr Asp Ile Ile Ile
290                 295                 300

Asp Phe Thr Ala Tyr Glu Gly Glu Ser Ile Ile Leu Ala Asn Ser Ala
305                 310                 315                 320

Gly Cys Gly Gly Asp Val Asn Pro Glu Thr Asp Ala Asn Ile Met Gln
                325                 330                 335

Phe Arg Val Thr Lys Pro Leu Ala Gln Lys Asp Glu Ser Arg Lys Pro
                340                 345                 350

Glu Tyr Leu Ala Ser Tyr Pro Ser Val Gln His Glu Arg Ile Gln Asn
                355                 360                 365

Ile Arg Thr Leu Lys Leu Ala Gly Thr Gln Asp Glu Tyr Gly Arg Pro
                370                 375                 380

Val Leu Leu Leu Asn Asn Lys Arg Trp His Asp Pro Val Thr Gly Ala
385                 390                 395                 400

Pro Lys Val Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
                420                 425                 430

Arg Arg Pro Phe Asp Ile Ala Arg Tyr Gln Glu Ser Gly Glu Leu Ser
                435                 440                 445

Tyr Thr Gly Pro Ala Val Pro Pro Pro Ser Glu Glu Gly Trp Lys
450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Arg His
                500                 505                 510

Lys

<210> SEQ ID NO 75
<211> LENGTH: 513
<212> TYPE: PRT

-continued

```
<213> ORGANISM: Bacillus spec

<400> SEQUENCE: 75

Met Thr Leu Glu Lys Phe Val Asp Ala Leu Pro Ile Pro Glu Thr Leu
 1               5                  10                  15

Lys Pro Val Gln Gln Thr Lys Glu Lys Thr Tyr Tyr Glu Val Thr Met
            20                  25                  30

Glu Glu Cys Ala His Lys Leu His Arg Asp Leu Pro Pro Thr Arg Leu
        35                  40                  45

Trp Gly Tyr Asn Cys Gln Phe Pro Gly Pro Thr Ile Glu Val Asn Arg
    50                  55                  60

Asn Glu Asn Val Tyr Val Lys Trp Met Asn His Leu Ser Ser Thr His
65                  70                  75                  80

Phe Leu Pro Val Asp His Thr Ile His His Ser Asp Ser Gln His Glu
                85                  90                  95

Glu Pro Glu Val Lys Thr Val Val His Leu His Gly Gly Val Thr Pro
            100                 105                 110

Glu Asp Ser Asp Gly Tyr Pro Glu Ala Trp Phe Thr Lys Asp Phe Glu
        115                 120                 125

Gln Thr Gly Pro Tyr Phe Lys Arg Glu Ile Tyr His Tyr Pro Asn Gln
    130                 135                 140

Gln Arg Gly Ala Ile Leu Trp Tyr His Asp His Ala Met Ala Leu Thr
145                 150                 155                 160

Arg Leu Asn Val Tyr Ala Gly Leu Ile Gly Ala Tyr Leu Ile His Asp
                165                 170                 175

Pro Lys Glu Lys Arg Leu Lys Leu Pro Ser Gly Glu Tyr Asp Val Pro
            180                 185                 190

Leu Leu Ile Thr Asp Arg Thr Ile Asn Gly Asp Gly Ser Leu Phe Tyr
        195                 200                 205

Pro Asn Gly Pro Glu Asn Pro Ser Pro Ser Leu Pro Asn Pro Ser Ile
    210                 215                 220

Val Pro Ala Phe Cys Gly Glu Thr Ile Leu Val Asn Gly Lys Ala Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Asp Gly Glu
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Tyr Asp Ile Ile Ile
    290                 295                 300

Asp Phe Thr Ala Tyr Glu Gly Gln Ser Ile Ile Leu Ala Asn Ser Glu
305                 310                 315                 320

Gly Cys Gly Gly Asp Ala Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln Asn Glu Arg Ile His Asn
        355                 360                 365

Ile Arg Thr Leu Lys Leu Ala Gly Thr Gln Asp Glu Tyr Gly Arg Pro
    370                 375                 380

Val Leu Leu Leu Asn Asn Lys Arg Trp His Asp Pro Val Thr Glu Thr
385                 390                 395                 400
```

-continued

```
Pro Lys Ala Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
            420                 425                 430

Arg Arg Pro Phe Asp Ile Ala Arg Tyr Gln Glu Arg Gly Glu Leu Ser
        435                 440                 445

Tyr Thr Gly Pro Ala Val Pro Pro Pro Ser Glu Lys Gly Trp Lys
    450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
                500                 505                 510

Lys

<210> SEQ ID NO 76
<211> LENGTH: 513
<212> TYPE: PRT
<213> ORGANISM: Bacillus spec

<400> SEQUENCE: 76

Met Thr Leu Glu Lys Phe Val Asp Ala Leu Pro Ile Pro Asp Thr Leu
1               5                  10                  15

Lys Pro Val Gln Gln Ser Lys Asp Ser Thr Tyr Tyr Glu Val Thr Met
                20                  25                  30

Glu Glu Cys Tyr His Gln Leu His Arg Asp Leu Pro Pro Thr Arg Leu
            35                  40                  45

Trp Gly Tyr Asn Gly Leu Phe Pro Gly Pro Thr Ile Lys Ala Lys Arg
        50                  55                  60

Asn Glu Asn Val Tyr Val Lys Trp Met Asn Asn Leu Pro Ser Glu His
65                  70                  75                  80

Phe Leu Pro Ile Asp His Thr Ile His His Ser Asp Ser Gln His Ala
                85                  90                  95

Glu Pro Glu Val Lys Thr Val Val His Leu His Gly Gly Val Thr Pro
                100                 105                 110

Asp Asp Ser Asp Gly Tyr Pro Glu Ala Trp Phe Ser Lys Asp Phe Glu
            115                 120                 125

Gln Thr Gly Pro Tyr Phe Lys Arg Glu Val Tyr His Tyr Pro Asn Gln
    130                 135                 140

Gln Arg Gly Ala Ile Leu Trp Tyr His Asp His Ala Met Ala Leu Thr
145                 150                 155                 160

Arg Leu Asn Val Tyr Ala Gly Leu Ile Gly Ala Tyr Ile Ile His Glu
                165                 170                 175

Pro Lys Glu Lys Arg Leu Lys Leu Pro Ser Gly Glu Tyr Asp Val Pro
                180                 185                 190

Leu Leu Ile Thr Asp Arg Thr Ile Asn Glu Asp Gly Ser Leu Phe Tyr
            195                 200                 205

Pro Ser Gly Pro Glu Asn Pro Ser Pro Ser Leu Pro Asn Pro Ser Ile
    210                 215                 220

Val Pro Ala Phe Cys Gly Asp Thr Ile Leu Val Asn Gly Lys Ala Trp
225                 230                 235                 240

Pro Tyr Met Glu Val Glu Pro Arg Lys Tyr Arg Phe Arg Val Ile Asn
                245                 250                 255
```

Ala Ser Asn Thr Arg Thr Tyr Asn Leu Ser Leu Asp Asn Gly Gly Glu
            260                 265                 270

Phe Ile Gln Ile Gly Ser Asp Gly Leu Leu Pro Arg Ser Val Lys
        275                 280                 285

Leu Asn Ser Phe Ser Ile Ala Pro Ala Glu Arg Phe Asp Ile Leu Ile
    290                 295                 300

Asp Phe Ala Ala Phe Glu Gly Gln Ser Ile Ile Leu Ala Asn Ser Glu
305                 310                 315                 320

Gly Cys Gly Gly Asp Val Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln His Glu Arg Ile Gln Asn
        355                 360                 365

Leu Arg Thr Leu Lys Leu Ala Gly Thr Gln Asp Gln Tyr Gly Arg Pro
    370                 375                 380

Val Leu Leu Leu Asn Asn Lys Arg Trp His Asp Pro Val Thr Glu Ala
385                 390                 395                 400

Pro Lys Val Gly Ser Thr Glu Ile Trp Ser Ile Ile Asn Pro Thr Arg
                405                 410                 415

Gly Thr His Pro Ile His Leu His Leu Val Ser Phe Arg Val Leu Asp
            420                 425                 430

Arg Arg Pro Phe Asp Thr Ala Arg Phe Glu Glu Arg Gly Glu Leu Ala
        435                 440                 445

Tyr Thr Gly Pro Ala Val Pro Pro Pro Ser Glu Lys Gly Trp Lys
    450                 455                 460

Asp Thr Val Gln Ser His Ala Gly Glu Val Leu Arg Ile Ala Val Thr
465                 470                 475                 480

Phe Gly Pro Tyr Thr Gly Arg Tyr Val Trp His Cys His Ile Leu Glu
                485                 490                 495

His Glu Asp Tyr Asp Met Met Arg Pro Met Asp Ile Thr Asp Pro His
            500                 505                 510

Lys

<210> SEQ ID NO 77
<211> LENGTH: 513
<212> TYPE: PRT
<213> ORGANISM: Bacillus spec

<400> SEQUENCE: 77

Met Thr Leu Glu Lys Phe Ala Asp Ala Leu Pro Ile Pro Asp Thr Leu
1               5                   10                  15

Lys Pro Val Gln Gln Ser Lys Asp Ser Thr Tyr Tyr Glu Val Thr Met
            20                  25                  30

Glu Glu Cys Tyr His Gln Leu His Arg Asp Leu Pro Pro Thr Arg Leu
        35                  40                  45

Trp Gly Tyr Asn Gly Leu Phe Pro Gly Pro Thr Ile Glu Ala Asn Arg
    50                  55                  60

Asn Glu Asn Val Tyr Val Lys Trp Met Asn Asn Leu Pro Ser Glu His
65                  70                  75                  80

Phe Leu Pro Ile Asp His Thr Ile His His Ser Asp Ser Gln His Ala
                85                  90                  95

Glu Pro Glu Val Lys Thr Val Val His Leu His Gly Gly Val Thr Pro
            100                 105                 110

```
Asp Asp Ser Asp Gly Tyr Pro Glu Ala Trp Phe Ser Lys Asp Phe Glu
            115                 120                 125

Gln Thr Gly Pro Tyr Phe Lys Arg Glu Val Tyr His Tyr Pro Asn Gln
        130                 135                 140

Gln Arg Gly Ala Ile Leu Trp Tyr His Asp His Ala Met Ala Leu Thr
145                 150                 155                 160

Arg Leu Asn Val Tyr Ala Gly Leu Ile Gly Ala Tyr Ile Ile Tyr Asp
                165                 170                 175

Pro Lys Glu Lys Arg Leu Lys Leu Pro Ser Gly Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Gly Pro Glu Asn Pro Ser Pro Ser Leu Pro Asn Pro Ser Ile
    210                 215                 220

Val Pro Ala Phe Cys Gly Asp Thr Ile Leu Val Asn Gly Lys Ala Trp
225                 230                 235                 240

Pro Tyr Met Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Glu
            260                 265                 270

Phe Ile Gln Ile Gly Ser Asp Gly Gly Leu Leu Pro Arg Ser Val Lys
        275                 280                 285

Leu Asn Ser Phe Ser Ile Ala Pro Ala Glu Arg Phe Asp Ile Leu Ile
    290                 295                 300

Asp Phe Ala Ala Phe Glu Gly Gln Ser Ile Ile Leu Ala Asn Ser Glu
305                 310                 315                 320

Gly Cys Gly Gly Asp Val Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln His Glu Arg Ile Gln Asn
        355                 360                 365

Leu Arg Thr Leu Lys Leu Ala Gly Thr Gln Asp Gln Tyr Gly Arg Pro
    370                 375                 380

Val Leu Leu Leu Asn Asn Lys Arg Trp His Asp Pro Val Thr Glu Ala
385                 390                 395                 400

Pro Lys Ala Gly Ser Thr Glu Val Trp Ser Ile Ile Asn Pro Thr Arg
                405                 410                 415

Gly Thr His Pro Ile His Leu His Leu Val Ser Phe Arg Val Leu Asp
            420                 425                 430

Arg Arg Pro Phe Asp Thr Ala Arg Phe Glu Glu Arg Gly Glu Leu Phe
        435                 440                 445

Tyr Thr Gly Pro Ala Val Pro Pro Pro Ser Glu Lys Gly Trp Lys
    450                 455                 460

Asp Thr Val Gln Ser His Ala Gly Glu Val Leu Arg Ile Ala Val Thr
465                 470                 475                 480

Phe Gly Pro Tyr Thr Gly Arg Tyr Val Trp His Cys His Ile Leu Glu
                485                 490                 495

His Glu Asp Tyr Asp Met Met Arg Pro Met Asp Val Ile Asp Pro His
            500                 505                 510

Lys
```

<210> SEQ ID NO 78

```
<211> LENGTH: 507
<212> TYPE: PRT
<213> ORGANISM: Bacillus spec
<220> FEATURE:
<221> NAME/KEY: misc_feature
<222> LOCATION: (34)..(34)
<223> OTHER INFORMATION: Xaa can be any naturally occurring amino acid

<400> SEQUENCE: 78

Thr Leu Glu Lys Phe Val Asp Ala Leu Pro Ile Pro Asp Thr Leu Lys
1               5                   10                  15

Pro Val Gln Gln Ser Lys Glu Lys Thr Tyr Tyr Glu Val Thr Met Glu
            20                  25                  30

Glu Xaa Cys Thr His Gln Leu His Arg Asp Leu Pro Pro Thr Arg Leu
        35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Thr His
65                  70                  75                  80

Phe Leu Pro Ile Asp His Thr Ile His Ser Glu Glu Pro Glu Val
                85                  90                  95

Lys Thr Val Val His Leu His Gly Gly Val Thr Pro Asp Asp Ser Asp
            100                 105                 110

Gly Tyr Pro Glu Ala Trp Phe Ser Lys Asp Phe Glu Gln Thr Gly Pro
        115                 120                 125

Tyr Phe Lys Arg Glu Val Tyr His Tyr Pro Asn Gln Gln Arg Gly Ala
    130                 135                 140

Ile Leu Trp Tyr His Asp His Ala Met Ala Leu Thr Arg Leu Asn Val
145                 150                 155                 160

Tyr Ala Gly Leu Val Gly Ala Tyr Ile Ile His Asp Pro Lys Glu Lys
                165                 170                 175

Arg Leu Lys Leu Pro Ser Asp Glu Tyr Asp Val Pro Leu Leu Ile Thr
            180                 185                 190

Asp Arg Thr Ile Asn Glu Asp Gly Ser Leu Phe Tyr Pro Ser Ala Pro
        195                 200                 205

Glu Asn Pro Ser Pro Ser Leu Pro Asn Pro Ser Ile Val Pro Ala Phe
    210                 215                 220

Cys Gly Glu Thr Ile Leu Val Asn Gly Lys Val Trp Pro Tyr Leu Glu
225                 230                 235                 240

Val Glu Pro Arg Lys Tyr Arg Phe Arg Val Ile Asn Ala Ser Asn Thr
                245                 250                 255

Arg Thr Tyr Asn Leu Ser Leu Asp Asn Gly Gly Asp Phe Ile Gln Ile
            260                 265                 270

Gly Ser Asp Gly Gly Leu Leu Pro Arg Ser Val Lys Leu Asn Ser Phe
        275                 280                 285

Ser Leu Ala Pro Ala Glu Arg Tyr Asp Ile Ile Ile Asp Phe Thr Ala
    290                 295                 300

Tyr Glu Gly Glu Ser Ile Ile Leu Ala Asn Ser Ala Gly Cys Gly Gly
305                 310                 315                 320

Asp Val Asn Pro Glu Thr Asp Ala Asn Ile Met Gln Phe Arg Val Thr
                325                 330                 335

Lys Pro Leu Ala Gln Lys Asp Glu Ser Arg Lys Pro Lys Tyr Leu Ala
            340                 345                 350

Ser Tyr Pro Ser Val Gln His Glu Arg Ile Gln Asn Ile Arg Thr Leu
        355                 360                 365
```

-continued

```
Lys Leu Ala Gly Thr Gln Asp Glu Tyr Gly Arg Pro Val Leu Leu Leu
370                 375                 380

Asn Asn Lys Arg Trp His Asp Pro Val Thr Glu Thr Pro Lys Val Gly
385                 390                 395                 400

Thr Thr Glu Ile Trp Ser Ile Ile Asn Pro Thr Arg Gly Thr His Pro
                405                 410                 415

Ile His Leu His Leu Val Ser Phe Arg Val Leu Asp Arg Arg Pro Phe
                420                 425                 430

Asp Ile Ala Arg Tyr Gln Glu Ser Gly Glu Leu Ser Tyr Thr Gly Pro
                435                 440                 445

Ala Val Pro Pro Pro Ser Glu Lys Gly Trp Lys Asp Thr Ile Gln
450                 455                 460

Ala His Ala Gly Glu Val Leu Arg Ile Ala Ala Thr Phe Gly Pro Tyr
465                 470                 475                 480

Ser Gly Arg Tyr Val Trp His Cys His Ile Leu Glu His Leu Asp Tyr
                485                 490                 495

Asp Met Met Arg Pro Met Asp Ile Thr Asp Pro
                500                 505

<210> SEQ ID NO 79
<211> LENGTH: 511
<212> TYPE: PRT
<213> ORGANISM: Bacillus spec

<400> SEQUENCE: 79

Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
                20                  25                  30

Glu Glu Cys Thr His Gln Leu His Arg Asp Leu Pro Pro Thr Arg Leu
            35                  40                  45

Trp Gly Tyr Asn Gly Leu Phe Pro Gly Pro Thr Ile Glu Val Lys Arg
50                  55                  60

Asn Glu Asn Val Tyr Val Lys Trp Met Asn Asn Leu Pro Ser Thr His
65              70                  75                  80

Phe Leu Pro Ile Asp His Thr Ile His Ser Asp Ser Gln His Glu
                85                  90                  95

Glu Pro Glu Val Lys Thr Val His Leu His Gly Gly Val Thr Pro
            100                 105                 110

Asp Asp Ser Asp Gly Tyr Pro Glu Ala Trp Phe Ser Lys Asp Phe Glu
        115                 120                 125

Gln Thr Gly Pro Tyr Phe Lys Arg Glu Val Tyr His Tyr Pro Asn Gln
130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Asp Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Ala Pro Glu Asn Pro Ser Pro Ser Leu Pro Asn Pro Ser Ile
210                 215                 220

Val Pro Ala Phe Cys Gly Glu Thr Ile Leu Val Asn Gly Lys Val Trp
225                 230                 235                 240
```

```
Pro Tyr Leu Glu Val Glu Pro Arg Lys Tyr Arg Phe Arg Val Ile Asn
            245                 250                 255

Ala Ser Asn Thr Arg Thr Tyr Asn Leu Ser Leu Asp Asn Gly Gly Asp
            260                 265                 270

Phe Ile Gln Ile Gly Ser Asp Gly Leu Leu Pro Arg Ser Val Lys
            275                 280                 285

Leu Asn Ser Phe Ser Leu Ala Pro Ala Glu Arg Tyr Asp Ile Ile Ile
290                 295                 300

Asp Phe Thr Ala Tyr Glu Gly Glu Ser Ile Ile Leu Ala Asn Ser Ala
305                 310                 315                 320

Gly Cys Gly Gly Asp Val Asn Pro Glu Thr Asp Ala Asn Ile Met Gln
            325                 330                 335

Phe Arg Val Thr Lys Pro Leu Ala Gln Lys Thr Lys Ala Glu Ser Arg
            340                 345                 350

Ser Thr Ser Pro His Thr Leu Arg Tyr Ser Met Lys Asp Thr Asn Ile
            355                 360                 365

Arg Thr Leu Lys Leu Ala Gly Thr Gln Asp Glu Tyr Gly Arg Pro Val
            370                 375                 380

Leu Leu Leu Asn Asn Lys Arg Trp His Asp Pro Val Thr Glu Thr Pro
385                 390                 395                 400

Lys Val Gly Thr Thr Glu Ile Trp Ser Ile Ile Asn Arg His Ala Glu
            405                 410                 415

His Ile Leu Ile His Leu His Leu Val Ser Phe Arg Val Leu Asp Arg
            420                 425                 430

Arg Pro Phe Asp Ile Ala Arg Tyr Gln Glu Ser Gly Glu Leu Ser Tyr
            435                 440                 445

Thr Val Arg Cys Pro Ala Ala Ala Ser Glu Lys Gly Trp Lys Asp Thr
            450                 455                 460

Ile Gln Ala His Ala Gly Glu Val Leu Arg Ile Ala Ala Thr Phe Gly
465                 470                 475                 480

Pro Tyr Ser Gly Arg Tyr Val Trp His Cys His Ile Leu Glu His Glu
            485                 490                 495

Asp Tyr Asp Met Met Arg Pro Met Asp Ile Thr Asp Pro His Lys
            500                 505                 510

<210> SEQ ID NO 80
<211> LENGTH: 513
<212> TYPE: PRT
<213> ORGANISM: Bacillus spec

<400> SEQUENCE: 80

Met Asn Leu Glu Lys Phe Ala Asp Met Leu Pro Ile Pro Glu Val Leu
1               5                   10                  15

Lys Pro His Gln Gln Thr Lys Glu Ser Thr Tyr Tyr Glu Val Thr Met
            20                  25                  30

Lys Glu Phe Tyr Gln Lys Leu His Arg Asp Leu Pro Pro Thr Arg Leu
            35                  40                  45

Trp Gly Tyr Asn Gly Leu Phe Pro Gly Pro Thr Ile Glu Val Asn Arg
        50                  55                  60

Asn Glu Asn Val Gln Ile Lys Trp Met Asn Asp Leu Pro Asp Gln His
65                  70                  75                  80

Phe Leu Pro Ile Asp His Thr Ile His His Ser Glu Gly His His Gln
            85                  90                  95

Glu Pro Glu Val Lys Thr Val Val His Leu His Gly Gly Ala Thr Pro
```

```
                  100                 105                 110
Tyr Asp Ser Asp Gly Tyr Pro Glu Ala Trp Phe Ser Lys Gly Phe Gln
            115                 120                 125

Glu Thr Gly Pro Tyr Phe Ser Arg Glu Ile Tyr His Tyr Pro Asn Gln
        130                 135                 140

Gln Arg Gly Ala Ile Leu Trp Tyr His Asp His Ala Met Ala Leu Thr
145                 150                 155                 160

Arg Leu Asn Val Tyr Ala Gly Leu Ala Gly Val Tyr Ile Ile His Asp
                165                 170                 175

Pro Lys Glu Lys Arg Leu Lys Leu Pro Ala Gly Glu Tyr Asp Val Pro
            180                 185                 190

Leu Met Ile Met Asp Arg Thr Ile Asn Glu Asp Gly Ser Leu Phe Tyr
        195                 200                 205

Pro Ser Gly Pro Glu Asn Pro Ser Pro Thr Leu Pro Thr Pro Ser Ile
    210                 215                 220

Val Pro Ala Phe Cys Gly Asp Thr Ile Leu Val Asn Gly Lys Ala Trp
225                 230                 235                 240

Pro Tyr Met Glu Val Glu Pro Arg Ala Tyr Arg Phe Arg Ile Val Asn
                245                 250                 255

Ala Ser Asn Thr Arg Thr Tyr Asn Leu Ser Leu Asp Asn Gly Gly Glu
            260                 265                 270

Phe Leu Gln Val Gly Ser Asp Gly Gly Leu Leu Pro Arg Ser Val Lys
        275                 280                 285

Leu Ser Ser Ile Ser Leu Ala Pro Ala Glu Arg Phe Asp Ile Ile Ile
    290                 295                 300

Asp Phe Ala Ala Phe Glu Gly Gln Ser Ile Val Leu Ala Asn Ser Glu
305                 310                 315                 320

Gly Cys Gly Gly Pro Ala Asn Pro Glu Ser Asp Ala Asn Val Met Gln
                325                 330                 335

Phe Arg Val Ile Lys Pro Leu Lys Glu Lys Asp Glu Ser Arg Lys Pro
            340                 345                 350

Arg Phe Leu Thr Asn Leu Pro Pro Val Thr Asp Glu Lys Ile Gln Asn
        355                 360                 365

Leu Arg Thr Leu Lys Leu Thr Gly Thr Gln Asp Glu Tyr Gly Arg Pro
    370                 375                 380

Val Leu Leu Leu Asn Asn Lys Arg Trp Ser Asp Pro Val Thr Glu Ala
385                 390                 395                 400

Pro Lys Leu Gly Thr Ser Glu Ile Trp Ser Ile Ile Asn Pro Thr Arg
                405                 410                 415

Gly Thr His Pro Ile His Leu His Leu Ile Ser Phe Arg Val Leu Asp
            420                 425                 430

Arg Arg Pro Phe Asp Thr Ala Lys Tyr Ala Glu Thr Gly Asn Val Val
        435                 440                 445

Phe Thr Gly Pro Ala Val Pro Pro Pro Ser Glu Lys Gly Trp Lys
    450                 455                 460

Asp Thr Val Gln Ser His Ala Gly Glu Val Ile Arg Ile Met Ala Lys
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Val Val Asp Pro Asn
            500                 505                 510

Gln
```

<210> SEQ ID NO 81
<211> LENGTH: 513
<212> TYPE: PRT
<213> ORGANISM: Bacillus spec

<400> SEQUENCE: 81

```
Met Asn Leu Glu Lys Phe Ala Asp Met Leu Pro Ile Pro Glu Val Leu
1               5                   10                  15
Lys Pro His Gln Gln Thr Lys Glu Ser Thr Tyr Tyr Glu Val Thr Met
            20                  25                  30
Lys Glu Phe Tyr Gln Lys Leu His Arg Asp Leu Pro Pro Thr Arg Leu
        35                  40                  45
Trp Gly Tyr Asn Ser Leu Phe Pro Gly Pro Thr Ile Glu Val Asn Arg
    50                  55                  60
Asn Glu Asn Val Gln Ile Lys Trp Met Asn Asp Leu Pro Asp Gln His
65                  70                  75                  80
Phe Leu Pro Ile Asp His Thr Ile His His Ser Glu Gly His His Gln
                85                  90                  95
Glu Pro Glu Val Lys Thr Val Val His Leu His Gly Gly Ala Thr Pro
            100                 105                 110
Tyr Asp Ser Asp Gly Tyr Pro Glu Ala Trp Phe Ser Lys Gly Phe Gln
        115                 120                 125
Glu Thr Gly Pro Tyr Phe Ser Arg Glu Ile Tyr His Tyr Pro Asn Gln
    130                 135                 140
Gln Arg Gly Ala Ile Leu Trp Tyr His Asp His Ala Met Ala Leu Thr
145                 150                 155                 160
Arg Leu Asn Val Tyr Ala Gly Leu Ala Gly Val Tyr Ile Ile His Asp
                165                 170                 175
Pro Lys Glu Lys Arg Leu Lys Leu Pro Ala Gly Glu Tyr Asp Val Pro
            180                 185                 190
Leu Met Ile Met Asp Arg Thr Ile Asn Glu Asp Gly Ser Leu Phe Tyr
        195                 200                 205
Pro Ser Gly Pro Glu Asn Pro Ser Pro Thr Leu Pro Thr Pro Ser Ile
    210                 215                 220
Val Pro Ala Phe Cys Gly Asp Thr Ile Leu Val Asn Gly Lys Ala Trp
225                 230                 235                 240
Pro Tyr Met Glu Val Glu Pro Arg Ala Tyr Arg Phe Arg Ile Val Asn
                245                 250                 255
Ala Ser Asn Thr Arg Thr Tyr Asn Leu Ser Leu Asp Asn Gly Gly Glu
            260                 265                 270
Phe Leu Gln Val Gly Ser Asp Gly Gly Leu Leu Pro Arg Ser Val Lys
        275                 280                 285
Leu Ser Ser Ile Ser Leu Ala Pro Ala Glu Arg Phe Asp Ile Ile Ile
    290                 295                 300
Asp Phe Ala Ala Phe Glu Gly Gln Ser Ile Val Leu Ala Asn Ser Glu
305                 310                 315                 320
Gly Cys Gly Gly Pro Ala Asn Pro Glu Ser Asp Ala Asn Val Met Gln
                325                 330                 335
Phe Arg Val Ile Lys Pro Leu Lys Glu Lys Asp Glu Ser Arg Lys Pro
            340                 345                 350
Arg Phe Leu Thr Asn Leu Pro Pro Val Thr Asp Glu Lys Ile Gln Asn
        355                 360                 365
Leu Arg Thr Leu Lys Leu Thr Gly Thr Gln Asp Glu Tyr Gly Arg Pro
    370                 375                 380
```

```
Val Leu Leu Leu Asn Asn Lys Arg Trp Ser Asp Pro Val Thr Glu Ala
385                 390                 395                 400

Pro Lys Leu Gly Thr Ser Glu Ile Trp Ser Ile Ile Asn Pro Thr Arg
            405                 410                 415

Gly Thr His Pro Ile His Leu His Leu Ile Ser Phe Arg Val Leu Asp
            420                 425                 430

Arg Arg Pro Phe Asp Thr Ala Lys Tyr Ala Glu Thr Gly Asn Val Val
            435                 440                 445

Phe Thr Gly Pro Ala Val Pro Pro Pro Ser Glu Lys Gly Trp Lys
            450                 455                 460

Asp Thr Val Gln Ser His Ala Gly Glu Val Ile Arg Ile Met Ala Lys
465                 470                 475                 480

Phe Gly Pro Tyr Ser Gly Arg Tyr Val Trp His Cys His Ile Leu Glu
            485                 490                 495

His Glu Asp Tyr Asp Met Met Arg Pro Met Asp Val Val Asp Pro Asn
            500                 505                 510

Gln

<210> SEQ ID NO 82
<211> LENGTH: 512
<212> TYPE: PRT
<213> ORGANISM: Bacillus spec

<400> SEQUENCE: 82

Met Ala Leu Glu Lys Phe Ala Asp Glu Leu Pro Ile Ile Glu Thr Leu
1               5                   10                  15

Gln Pro Gln Lys Lys Ser Asp Gly Ser Thr Tyr Tyr Glu Val Thr Met
                20                  25                  30

Lys Glu Cys Phe His Lys Leu His Arg Asp Leu Pro Pro Thr Arg Leu
            35                  40                  45

Trp Gly Tyr Asn Gly Leu Phe Pro Gly Pro Thr Ile Asp Val Asn Lys
    50                  55                  60

Asp Glu Asn Val Tyr Ile Lys Trp Met Asn Asp Leu Pro Asp Lys His
65                  70                  75                  80

Phe Leu Pro Val Asp His Thr Ile His His Ser Glu Ser Gly His Gln
                85                  90                  95

Glu Pro Asp Val Lys Thr Val His Leu His Gly Gly Ala Thr Pro
                100                 105                 110

Pro Asp Ser Asp Gly Tyr Pro Glu Ala Trp Phe Thr Lys Asp Phe Lys
            115                 120                 125

Glu Thr Gly Pro Tyr Phe Glu Lys Glu Val Tyr His Tyr Pro Asn Lys
130                 135                 140

Gln Arg Gly Ala Leu Leu Trp Tyr His Asp His Ala Met Ala Ile Thr
145                 150                 155                 160

Arg Leu Asn Val Tyr Ala Gly Leu Ala Gly Met Tyr Ile Ile Arg Glu
                165                 170                 175

Arg Lys Glu Lys Gln Leu Lys Leu Pro Ser Gly Glu Tyr Asp Val Pro
                180                 185                 190

Leu Met Ile Leu Asp Arg Thr Leu Asn Asp Asp Gly Ser Leu Ser Tyr
            195                 200                 205

Pro Ser Gly Pro Ala Asn Pro Ser Glu Thr Leu Pro Asp Pro Ser Ile
    210                 215                 220

Val Pro Phe Phe Cys Gly Asn Thr Ile Leu Val Asn Gly Lys Ala Trp
225                 230                 235                 240
```

```
Pro Tyr Met Glu Val Glu Pro Arg Thr Tyr Arg Phe Arg Ile Leu Asn
            245                 250                 255

Ala Ser Asn Thr Arg Thr Phe Ser Leu Ser Leu Asn Asn Gly Gly Lys
        260                 265                 270

Phe Ile Gln Ile Gly Ser Asp Gly Gly Leu Leu Pro Arg Ser Val Lys
    275                 280                 285

Thr Gln Ser Ile Ser Leu Ala Pro Ala Glu Arg Tyr Asp Val Leu Ile
290                 295                 300

Asp Phe Ser Ala Phe Asp Gly Glu His Ile Ile Leu Thr Asn Gly Thr
305                 310                 315                 320

Gly Cys Gly Gly Asp Ala Asp Pro Asp Thr Ala Asn Val Met Gln
                325                 330                 335

Phe Arg Val Thr Lys Pro Leu Lys Gly Glu Asp Thr Ser Arg Lys Pro
            340                 345                 350

Lys Tyr Leu Ser Thr Met Pro Asn Val Thr Ser Lys Arg Ile His Asn
        355                 360                 365

Ile Arg Thr Leu Lys Leu Thr Asn Thr Gln Asp Lys Tyr Gly Arg Pro
    370                 375                 380

Val Leu Thr Leu Asn Asn Lys Arg Trp His Asp Pro Val Thr Glu Ala
385                 390                 395                 400

Pro Lys Leu Gly Thr Thr Glu Ile Trp Ser Ile Ile Asn Pro Met Gly
                405                 410                 415

Gly Thr His Pro Ile His Leu His Leu Val Ser Phe Gln Ile Leu Asp
            420                 425                 430

Arg Arg Pro Phe Asp Leu Glu Arg Tyr Asn Lys Phe Gly Asp Ile Val
        435                 440                 445

Tyr Thr Gly Pro Ala Val Pro Pro Pro Ser Glu Lys Gly Trp Lys
    450                 455                 460

Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
                485                 490                 495

His Glu Asp Tyr Asp Met Met Arg Pro Met Asp Val Thr Asp Lys Gln
            500                 505                 510

<210> SEQ ID NO 83
<211> LENGTH: 512
<212> TYPE: PRT
<213> ORGANISM: Bacillus spec

<400> SEQUENCE: 83

Met Ala Leu Glu Lys Phe Ala Asp Glu Leu Pro Ile Ile Glu Thr Leu
1               5                   10                  15

Gln Pro Gln Lys Lys Ser Asp Gly Ser Thr Tyr Tyr Glu Val Thr Met
            20                  25                  30

Lys Glu Cys Phe His Lys Leu His Arg Asp Leu Pro Pro Thr Arg Leu
        35                  40                  45

Trp Gly Tyr Asn Gly Leu Phe Pro Gly Pro Thr Ile Asp Val Asn Gln
    50                  55                  60

Asp Glu Asn Val Tyr Ile Lys Trp Met Asn Asp Leu Pro Asp Lys His
65                  70                  75                  80

Phe Leu Pro Val Asp His Thr Ile His Ser Glu Ser Gly His Gln
                85                  90                  95

Glu Pro Asp Val Lys Thr Val Val His Leu His Gly Gly Ala Thr Pro
```

```
            100                 105                 110
Pro Asp Ser Asp Gly Tyr Pro Glu Ala Trp Phe Thr Lys Asp Phe Lys
            115                 120                 125

Glu Thr Gly Pro Tyr Phe Glu Arg Glu Val Tyr His Tyr Pro Asn Lys
            130                 135                 140

Gln Arg Gly Ala Leu Leu Trp Tyr His Asp His Ala Met Ala Ile Thr
145                 150                 155                 160

Arg Leu Asn Val Tyr Ala Gly Leu Ala Gly Met Tyr Ile Ile Arg Glu
                165                 170                 175

Arg Lys Glu Lys Gln Leu Lys Leu Pro Ser Gly Glu Tyr Asp Val Pro
            180                 185                 190

Leu Met Ile Leu Asp Arg Thr Leu Asn Asp Asp Gly Ser Leu Ser Tyr
            195                 200                 205

Pro Ser Gly Pro Ala Asn Pro Ser Glu Thr Leu Pro Asp Pro Ser Ile
            210                 215                 220

Val Pro Phe Phe Cys Gly Asn Thr Ile Leu Val Asn Gly Lys Ala Trp
225                 230                 235                 240

Pro Tyr Met Glu Val Glu Pro Arg Thr Tyr Arg Phe Arg Ile Leu Asn
                245                 250                 255

Ala Ser Asn Thr Arg Thr Phe Ser Leu Ser Leu Asn Asn Gly Gly Lys
                260                 265                 270

Phe Ile Gln Ile Gly Ser Asp Gly Gly Leu Leu Pro Arg Ser Val Lys
            275                 280                 285

Thr Gln Ser Ile Ser Leu Ala Pro Ala Glu Arg Tyr Asp Val Leu Ile
            290                 295                 300

Asp Phe Ser Ala Phe Asp Gly Glu His Ile Ile Leu Thr Asn Gly Thr
305                 310                 315                 320

Gly Cys Gly Gly Asp Ala Asp Pro Asp Thr Ala Asn Val Met Gln
                325                 330                 335

Phe Arg Val Thr Lys Pro Leu Lys Gly Ala Asp Thr Ser Arg Lys Pro
            340                 345                 350

Lys Tyr Leu Ser Thr Met Pro Asn Val Thr Ser Lys Arg Ile His Asn
            355                 360                 365

Ile Arg Thr Leu Lys Leu Thr Asn Thr Gln Asp Lys Tyr Gly Arg Pro
            370                 375                 380

Val Leu Thr Leu Asn Asn Lys Arg Trp His Asp Pro Val Thr Glu Ala
385                 390                 395                 400

Pro Lys Leu Gly Thr Thr Glu Ile Trp Ser Ile Ile Asn Pro Met Gly
            405                 410                 415

Gly Thr His Pro Ile His Leu His Leu Val Ser Phe Gln Ile Leu Asp
            420                 425                 430

Arg Arg Pro Phe Asp Leu Glu Arg Tyr Asn Lys Phe Gly Asp Ile Val
            435                 440                 445

Tyr Thr Gly Pro Ala Val Pro Pro Pro Ser Glu Lys Gly Trp Lys
            450                 455                 460

Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
                485                 490                 495

His Glu Asp Tyr Asp Met Met Arg Pro Met Asp Val Thr Asp Lys Gln
            500                 505                 510

<210> SEQ ID NO 84
```

<211> LENGTH: 512
<212> TYPE: PRT
<213> ORGANISM: Bacillus spec

<400> SEQUENCE: 84

```
Met Ala Leu Glu Lys Phe Ala Asp Glu Leu Pro Ile Ile Glu Thr Leu
1               5                   10                  15

Gln Pro Gln Lys Lys Ser Asp Gly Ser Thr Tyr Tyr Glu Val Thr Met
            20                  25                  30

Lys Glu Cys Phe His Lys Leu His Arg Asp Leu Pro Pro Thr Arg Leu
        35                  40                  45

Trp Gly Tyr Asn Gly Leu Phe Pro Gly Pro Thr Ile Asp Val Asn Gln
    50                  55                  60

Asp Glu Asn Val Tyr Ile Lys Trp Met Asn Asp Leu Pro Asp Lys His
65                  70                  75                  80

Phe Leu Pro Val Asp His Thr Ile His Ser Glu Ser Gly His Gln
                85                  90                  95

Glu Pro Asp Val Lys Thr Val Val His Leu His Gly Gly Ala Thr Pro
            100                 105                 110

Pro Asp Ser Asp Gly Tyr Pro Glu Ala Trp Phe Thr Lys Asp Phe Lys
        115                 120                 125

Glu Thr Gly Pro Tyr Phe Glu Lys Glu Val Tyr His Tyr Pro Asn Lys
    130                 135                 140

Gln Arg Gly Ala Leu Leu Trp Tyr His Asp His Ala Met Ala Ile Thr
145                 150                 155                 160

Arg Leu Asn Val Tyr Ala Gly Leu Ala Gly Met Tyr Ile Ile Arg Glu
                165                 170                 175

Arg Lys Glu Lys Gln Leu Lys Leu Pro Ser Gly Glu Tyr Asp Val Pro
            180                 185                 190

Leu Met Ile Leu Asp Arg Thr Leu Asn Asp Asp Gly Ser Leu Ser Tyr
        195                 200                 205

Pro Ser Gly Pro Ala Asn Pro Ser Glu Thr Leu Pro Asp Pro Ser Ile
    210                 215                 220

Val Pro Phe Phe Cys Gly Asn Thr Ile Leu Val Asn Gly Lys Ala Trp
225                 230                 235                 240

Pro Tyr Met Glu Val Glu Pro Arg Thr Tyr Arg Phe Arg Ile Leu Asn
                245                 250                 255

Ala Ser Asn Thr Arg Thr Phe Ser Leu Ser Leu Asn Asn Gly Gly Lys
            260                 265                 270

Phe Ile Gln Ile Gly Ser Asp Gly Gly Leu Leu Pro Arg Ser Val Lys
        275                 280                 285

Thr Gln Ser Ile Ser Leu Ala Pro Ala Glu Arg Tyr Asp Val Leu Ile
    290                 295                 300

Asp Phe Ser Ala Phe Asp Gly Glu His Ile Ile Leu Thr Asn Gly Thr
305                 310                 315                 320

Gly Cys Gly Gly Asp Ala Asp Pro Asp Thr Ala Asn Val Met Gln
                325                 330                 335

Phe Arg Val Thr Lys Pro Leu Lys Gly Glu Asp Thr Ser Arg Lys Pro
            340                 345                 350

Lys Tyr Leu Ser Thr Met Pro Asn Val Thr Ser Lys Arg Ile His Asn
        355                 360                 365

Ile Arg Thr Leu Lys Leu Thr Asn Thr Gln Asp Lys Tyr Gly Arg Pro
    370                 375                 380

Val Leu Thr Leu Asn Asn Lys Arg Trp His Asp Pro Val Thr Glu Ala
```

```
            385                 390                 395                 400
    Pro Lys Leu Gly Thr Thr Glu Ile Trp Ser Ile Ile Asn Pro Met Gly
                    405                 410                 415

Gly Thr His Pro Ile His Leu His Leu Val Ser Phe Gln Ile Leu Asp
                    420                 425                 430

Arg Arg Pro Phe Asp Leu Glu Arg Tyr Asn Lys Phe Gly Asp Ile Val
                    435                 440                 445

Tyr Thr Gly Pro Ala Val Pro Pro Pro Ser Glu Lys Gly Trp Lys
                    450                 455                 460

Asp Thr Val Gln Ala His Ser Gly Glu Val Ile Arg Ile Ala Ala Thr
    465                 470                 475                 480

Phe Ala Pro Tyr Ser Gly Arg Tyr Val Trp His Cys His Ile Leu Glu
                    485                 490                 495

His Glu Asp Tyr Asp Met Met Arg Pro Met Asp Val Thr Asp Lys Gln
                    500                 505                 510

<210> SEQ ID NO 85
    <211> LENGTH: 512
    <212> TYPE: PRT
    <213> ORGANISM: Bacillus spec

<400> SEQUENCE: 85

Met Ala Leu Glu Lys Phe Ala Asp Glu Leu Pro Ile Ile Glu Thr Leu
    1               5                   10                  15

Gln Pro Gln Lys Lys Ser Asp Gly Ser Thr Tyr Tyr Glu Val Thr Met
                    20                  25                  30

Lys Glu Cys Phe His Lys Leu His Arg Asp Leu Pro Pro Thr Arg Leu
                    35                  40                  45

Trp Gly Tyr Asn Gly Leu Phe Pro Gly Pro Thr Ile Asp Val Asn Gln
                50                  55                  60

Asp Glu Asn Val Tyr Ile Lys Trp Met Asn Asp Leu Pro Asp Lys His
    65                  70                  75                  80

Phe Leu Pro Val Asp His Thr Ile His His Ser Glu Ser Gly His Gln
                    85                  90                  95

Glu Pro Asp Val Lys Thr Val Val His Leu His Gly Gly Ala Thr Pro
                    100                 105                 110

Pro Asp Ser Asp Gly Tyr Pro Glu Ala Trp Phe Thr Lys Asp Phe Lys
                    115                 120                 125

Glu Thr Gly Pro Tyr Phe Glu Lys Glu Val Tyr His Tyr Pro Asn Lys
                    130                 135                 140

Gln Arg Gly Ala Leu Leu Trp Tyr His Asp His Ala Met Ala Ile Thr
    145                 150                 155                 160

Arg Leu Asn Val Tyr Ala Gly Leu Ala Gly Met Tyr Ile Ile Arg Glu
                    165                 170                 175

Arg Lys Glu Lys Gln Leu Lys Leu Pro Ser Gly Glu Tyr Asp Val Pro
                    180                 185                 190

Leu Met Ile Leu Asp Arg Thr Leu Asn Asp Asp Gly Ser Leu Ser Tyr
                    195                 200                 205

Pro Ser Gly Pro Ala Asn Pro Ser Glu Thr Leu Pro Asp Pro Ser Ile
                    210                 215                 220

Val Pro Phe Phe Cys Gly Asn Thr Ile Leu Val Asn Gly Lys Ala Trp
    225                 230                 235                 240

Pro Tyr Met Glu Val Glu Pro Arg Thr Tyr Arg Phe Arg Ile Leu Asn
                    245                 250                 255
```

Ala Ser Asn Thr Arg Thr Phe Ser Leu Ser Leu Asn Asn Gly Gly Lys
            260                 265                 270

Phe Ile Gln Ile Gly Ser Asp Gly Leu Leu Pro Arg Ser Val Lys
        275                 280                 285

Thr Gln Ser Ile Ser Leu Ala Pro Ala Glu Arg Tyr Asp Val Leu Ile
    290                 295                 300

Asp Phe Ser Ala Phe Asp Gly Glu His Ile Ile Leu Thr Asn Gly Thr
305                 310                 315                 320

Gly Cys Gly Gly Asp Ala Asp Pro Asp Thr Ala Asn Val Met Gln
                325                 330                 335

Phe Arg Val Thr Lys Pro Leu Lys Gly Ala Asp Thr Ser Arg Lys Pro
            340                 345                 350

Lys Tyr Leu Ser Thr Met Pro Asn Val Thr Ser Lys Arg Ile His Asn
            355                 360                 365

Ile Arg Thr Leu Lys Leu Thr Asn Thr Gln Asp Lys Tyr Gly Arg Pro
        370                 375                 380

Val Leu Thr Leu Asn Asn Lys Arg Trp His Asp Pro Val Thr Glu Ala
385                 390                 395                 400

Pro Lys Leu Gly Thr Thr Glu Ile Trp Ser Ile Ile Asn Pro Met Gly
                405                 410                 415

Gly Thr His Pro Ile His Leu His Leu Val Ser Phe Gln Ile Leu Asp
                420                 425                 430

Arg Arg Pro Phe Asp Leu Glu Arg Tyr Asn Lys Phe Gly Asp Ile Val
            435                 440                 445

Tyr Thr Gly Pro Ala Val Pro Pro Pro Ser Glu Lys Gly Trp Lys
        450                 455                 460

Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
                485                 490                 495

His Glu Asp Tyr Asp Met Met Arg Pro Met Asp Val Thr Asp Lys Gln
            500                 505                 510

<210> SEQ ID NO 86
<211> LENGTH: 512
<212> TYPE: PRT
<213> ORGANISM: Bacillus spec

<400> SEQUENCE: 86

Met Ala Leu Glu Lys Phe Ala Asp Glu Leu Pro Ile Ile Glu Thr Leu
1               5                   10                  15

Gln Pro Gln Lys Lys Ser Asp Gly Ser Thr Tyr Tyr Glu Val Thr Met
            20                  25                  30

Lys Glu Cys Phe His Lys Leu His Arg Asp Leu Pro Pro Thr Arg Leu
        35                  40                  45

Trp Gly Tyr Asn Gly Leu Phe Pro Gly Pro Thr Ile Asp Val Asn Gln
    50                  55                  60

Asp Glu Asn Val Tyr Ile Lys Trp Met Asn Asp Leu Pro Asp Lys His
65                  70                  75                  80

Phe Leu Pro Val Asp His Thr Ile His His Ser Glu Ser Gly His Gln
                85                  90                  95

Glu Pro Asp Val Lys Thr Val Val His Leu His Gly Gly Ala Thr Pro
            100                 105                 110

Pro Asp Ser Asp Gly Tyr Pro Glu Ala Trp Phe Thr Lys Asp Phe Lys
        115                 120                 125

Glu Thr Gly Pro Tyr Phe Glu Arg Glu Val Tyr His Tyr Pro Asn Lys
            130                 135                 140

Gln Arg Gly Ala Leu Leu Trp Tyr His Asp His Ala Met Ala Ile Thr
145                 150                 155                 160

Arg Leu Asn Val Tyr Ala Gly Leu Ala Gly Met Tyr Ile Ile Arg Glu
                165                 170                 175

Arg Lys Glu Lys Gln Leu Lys Leu Pro Ser Gly Glu Tyr Asp Val Pro
            180                 185                 190

Leu Met Ile Leu Asp Arg Thr Leu Asn Asp Asp Gly Ser Leu Ser Tyr
            195                 200                 205

Pro Ser Gly Pro Ala Asn Pro Ser Glu Thr Leu Pro Asp Pro Ser Ile
210                 215                 220

Val Pro Phe Phe Cys Gly Asn Thr Ile Leu Val Asn Gly Lys Ala Trp
225                 230                 235                 240

Pro Tyr Met Glu Val Glu Pro Arg Thr Tyr Arg Phe Arg Ile Leu Asn
                245                 250                 255

Ala Ser Asn Thr Arg Thr Phe Ser Leu Ser Leu Asn Asn Gly Gly Lys
                260                 265                 270

Phe Ile Gln Ile Gly Ser Asp Gly Gly Leu Leu Pro Arg Ser Val Lys
            275                 280                 285

Thr Gln Ser Ile Ser Leu Ala Pro Ala Glu Arg Tyr Asp Val Leu Ile
290                 295                 300

Asp Phe Ser Ala Phe Asp Gly Glu His Ile Ile Leu Thr Asn Gly Thr
305                 310                 315                 320

Gly Cys Gly Gly Asp Ala Asp Pro Asp Thr Asp Ala Asn Val Met Gln
                325                 330                 335

Phe Arg Val Thr Lys Pro Leu Lys Gly Ala Glu Thr Ser Arg Lys Pro
            340                 345                 350

Lys Tyr Leu Ser Thr Met Pro Asn Val Thr Ser Lys Arg Ile His Asn
            355                 360                 365

Ile Arg Thr Leu Lys Leu Thr Asn Thr Gln Asp Lys Tyr Gly Arg Pro
370                 375                 380

Val Leu Thr Leu Asn Asn Lys Arg Trp His Asp Pro Val Thr Glu Ala
385                 390                 395                 400

Pro Lys Leu Gly Thr Thr Glu Ile Trp Ser Ile Ile Asn Pro Met Gly
                405                 410                 415

Gly Thr His Pro Ile His Leu His Leu Val Ser Phe Gln Ile Leu Asp
                420                 425                 430

Arg Arg Pro Phe Asp Leu Glu Arg Tyr Asn Lys Phe Gly Asp Ile Val
            435                 440                 445

Tyr Thr Gly Pro Ala Val Pro Pro Pro Ser Glu Lys Gly Trp Lys
450                 455                 460

Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
                485                 490                 495

His Glu Asp Tyr Asp Met Met Arg Pro Met Asp Val Thr Asp Lys Gln
            500                 505                 510

<210> SEQ ID NO 87
<211> LENGTH: 512
<212> TYPE: PRT
<213> ORGANISM: Bacillus spec

<400> SEQUENCE: 87

```
Met Ala Leu Glu Lys Phe Ala Asp Glu Leu Pro Ile Ile Glu Thr Leu
1               5                   10                  15

Gln Pro Gln Lys Lys Ser Asp Gly Ser Thr Tyr Tyr Glu Val Thr Met
            20                  25                  30

Lys Glu Cys Phe His Lys Leu His Arg Asp Leu Pro Pro Thr Arg Leu
        35                  40                  45

Trp Gly Tyr Asn Gly Leu Phe Pro Gly Pro Thr Ile Asp Val Asn Lys
    50                  55                  60

Asp Glu Asn Val Tyr Ile Lys Trp Met Asn Asp Leu Pro Asp Lys His
65                  70                  75                  80

Phe Leu Pro Val Asp His Thr Ile His His Ser Glu Ser Gly His Gln
                85                  90                  95

Glu Pro Asp Val Lys Thr Val Val His Leu His Gly Gly Ala Thr Pro
            100                 105                 110

Pro Asp Ser Asp Gly Tyr Pro Glu Ala Trp Phe Thr Lys Asp Phe Lys
        115                 120                 125

Glu Thr Gly Pro Tyr Phe Glu Arg Glu Val Tyr His Tyr Pro Asn Lys
    130                 135                 140

Gln Arg Gly Ala Leu Leu Trp Tyr His Asp His Ala Met Ala Ile Thr
145                 150                 155                 160

Arg Leu Asn Val Tyr Ala Gly Leu Ala Gly Met Tyr Ile Ile Arg Glu
                165                 170                 175

Arg Lys Glu Lys Gln Leu Lys Leu Pro Ser Gly Glu Tyr Asp Val Pro
            180                 185                 190

Leu Met Ile Leu Asp Arg Thr Leu Asn Asp Asp Gly Ser Leu Ser Tyr
        195                 200                 205

Pro Ser Gly Pro Ala Asn Pro Ser Glu Thr Leu Pro Asp Pro Ser Ile
    210                 215                 220

Val Pro Phe Phe Cys Gly Asn Thr Ile Leu Val Asn Gly Lys Ala Trp
225                 230                 235                 240

Pro Tyr Met Glu Val Glu Pro Arg Thr Tyr Arg Phe Arg Ile Leu Asn
                245                 250                 255

Ala Ser Asn Thr Arg Thr Phe Ser Leu Ser Leu Asn Asn Gly Gly Lys
            260                 265                 270

Phe Ile Gln Ile Gly Ser Asp Gly Gly Leu Leu Pro Arg Ser Val Lys
        275                 280                 285

Thr Gln Ser Ile Ser Leu Ala Pro Ala Glu Arg Tyr Asp Val Leu Ile
    290                 295                 300

Asp Phe Ser Ala Phe Asp Gly Glu His Ile Ile Leu Thr Asn Gly Thr
305                 310                 315                 320

Gly Cys Gly Gly Asp Ala Asp Pro Asp Thr Ala Asn Val Met Gln
                325                 330                 335

Phe Arg Val Thr Lys Pro Leu Lys Gly Ala Asp Thr Ser Arg Lys Pro
            340                 345                 350

Lys Tyr Leu Ser Thr Met Pro Asn Val Thr Ser Lys Arg Ile His Asn
        355                 360                 365

Ile Arg Met Leu Lys Leu Thr Asn Thr Gln Asp Lys Tyr Gly Arg Pro
    370                 375                 380

Val Leu Thr Leu Asn Asn Lys Arg Trp His Asp Pro Val Thr Glu Ala
385                 390                 395                 400

Pro Lys Leu Gly Thr Thr Glu Ile Trp Ser Ile Ile Asn Pro Met Gly
                405                 410                 415
```

Gly Thr His Pro Ile His Leu His Leu Val Ser Phe Gln Ile Leu Asp
            420                 425                 430

Arg Arg Pro Phe Asp Leu Glu Arg Tyr Asn Lys Phe Gly Asp Ile Val
            435                 440                 445

Tyr Thr Gly Pro Ala Val Pro Pro Pro Ser Glu Lys Gly Trp Lys
450                 455                 460

Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
            485                 490                 495

His Glu Asp Tyr Asp Met Met Arg Pro Met Asp Val Thr Asp Lys Gln
            500                 505                 510

<210> SEQ ID NO 88
<211> LENGTH: 512
<212> TYPE: PRT
<213> ORGANISM: Bacillus spec

<400> SEQUENCE: 88

Met Ala Leu Glu Lys Phe Ala Asp Glu Leu Pro Ile Ile Glu Thr Leu
1               5                   10                  15

Gln Pro Gln Lys Lys Ser Asp Gly Ser Thr Tyr Tyr Glu Val Thr Met
            20                  25                  30

Lys Glu Cys Phe His Lys Leu His Arg Asp Leu Pro Pro Thr Arg Leu
            35                  40                  45

Trp Gly Tyr Asn Gly Leu Phe Pro Gly Pro Thr Ile Asp Val Asn Gln
50                  55                  60

Asp Glu Asn Val Tyr Ile Lys Trp Met Asn Asp Leu Pro Asp Lys His
65                  70                  75                  80

Phe Leu Pro Val Asp His Thr Ile His His Ser Glu Ser Gly His Gln
            85                  90                  95

Glu Pro Asp Val Lys Thr Val Val His Leu His Gly Gly Ala Thr Pro
            100                 105                 110

Pro Asp Ser Asp Gly Tyr Pro Glu Ala Trp Phe Thr Lys Asp Phe Lys
            115                 120                 125

Glu Thr Gly Pro Tyr Phe Glu Lys Glu Val Tyr His Tyr Pro Asn Lys
            130                 135                 140

Gln Arg Gly Ala Leu Leu Trp Tyr His Asp His Ala Met Ala Ile Thr
145                 150                 155                 160

Arg Leu Asn Val Phe Ala Gly Leu Ala Gly Met Tyr Ile Ile Arg Glu
            165                 170                 175

Arg Lys Glu Lys Gln Leu Lys Leu Pro Ser Gly Glu Tyr Asp Val Pro
            180                 185                 190

Leu Met Ile Leu Asp Arg Thr Leu Asn Asp Asp Gly Ser Leu Ser Tyr
            195                 200                 205

Pro Ser Gly Pro Ala Asn Pro Ser Glu Thr Leu Pro Asp Pro Ser Ile
            210                 215                 220

Val Pro Phe Phe Cys Gly Asn Thr Ile Leu Val Asn Gly Lys Ala Trp
225                 230                 235                 240

Pro Tyr Met Glu Val Glu Pro Arg Thr Tyr Arg Phe Arg Ile Leu Asn
            245                 250                 255

Ala Ser Asn Thr Arg Thr Phe Ser Leu Ser Leu Asn Asn Gly Gly Lys
            260                 265                 270

Phe Ile Gln Ile Gly Ser Asp Gly Gly Leu Leu Pro Arg Ser Val Lys

```
            275                 280                 285
Thr Gln Ser Ile Ser Leu Ala Pro Ala Glu Arg Tyr Asp Val Leu Ile
    290                 295                 300
Asp Phe Ser Ala Phe Asp Gly Glu His Ile Ile Leu Thr Asn Gly Thr
305                 310                 315                 320
Gly Cys Gly Gly Asp Ala Pro Asp Thr Asp Ala Asn Val Met Gln
                    325                 330                 335
Phe Arg Val Thr Lys Pro Leu Lys Gly Glu Asp Thr Ser Arg Lys Pro
                340                 345                 350
Lys Tyr Leu Ser Thr Met Pro Asn Val Thr Ser Lys Arg Ile His Asn
                355                 360                 365
Ile Arg Thr Leu Lys Leu Thr Asn Thr Gln Asp Lys Tyr Gly Arg Pro
            370                 375                 380
Val Leu Thr Leu Asn Asn Lys Arg Trp His Asp Pro Val Thr Glu Ala
385                 390                 395                 400
Pro Lys Leu Gly Thr Thr Glu Ile Trp Ser Ile Ile Asn Pro Met Gly
                    405                 410                 415
Gly Thr His Pro Ile His Leu His Leu Val Ser Phe Gln Ile Leu Asp
                420                 425                 430
Arg Arg Pro Phe Asp Leu Glu Arg Tyr Asn Lys Phe Gly Asp Ile Val
            435                 440                 445
Tyr Thr Gly Pro Ala Val Pro Pro Pro Ser Glu Lys Gly Trp Lys
                450                 455                 460
Asp Thr Val Gln Ala His Ser Gly Glu Val Ile Arg Ile Ala Ala Thr
465                 470                 475                 480
Phe Ala Pro Tyr Ser Gly Arg Tyr Val Trp His Cys His Ile Leu Glu
                    485                 490                 495
His Glu Asp Tyr Asp Met Met Arg Pro Met Asp Val Thr Asp Lys Gln
                500                 505                 510

<210> SEQ ID NO 89
<211> LENGTH: 512
<212> TYPE: PRT
<213> ORGANISM: Bacillus spec

<400> SEQUENCE: 89

Met Ala Leu Glu Lys Phe Ala Asp Glu Leu Pro Ile Ile Glu Thr Leu
1               5                   10                  15
Gln Pro Gln Lys Lys Ser Asp Gly Ser Thr Tyr Tyr Glu Val Thr Met
                20                  25                  30
Lys Glu Cys Phe His Lys Leu His Arg Asp Leu Pro Pro Thr Arg Leu
            35                  40                  45
Trp Gly Tyr Asn Gly Leu Phe Pro Gly Pro Thr Ile Asp Val Asn Gln
        50                  55                  60
Asp Glu Asn Val Tyr Ile Lys Trp Met Asn Asp Leu Pro Asp Lys His
65                  70                  75                  80
Phe Leu Pro Val Asp His Thr Ile His His Ser Glu Ser Gly His Gln
                    85                  90                  95
Glu Pro Asp Val Lys Thr Val Val His Leu His Gly Gly Ala Thr Pro
                100                 105                 110
Pro Asp Ser Asp Gly Tyr Pro Glu Ala Trp Phe Thr Lys Asp Phe Lys
            115                 120                 125
Glu Thr Gly Pro Tyr Phe Glu Arg Glu Val Tyr His Tyr Pro Asn Lys
        130                 135                 140
```

```
Gln Arg Gly Ala Leu Leu Trp Tyr His Asp His Ala Met Ala Ile Thr
145                 150                 155                 160

Arg Leu Asn Val Tyr Ala Gly Leu Ala Gly Met Tyr Ile Ile Arg Glu
            165                 170                 175

Arg Lys Glu Lys Gln Leu Lys Leu Pro Ser Gly Glu Tyr Asp Val Pro
            180                 185                 190

Leu Met Ile Leu Asp Arg Thr Leu Asn Asp Asp Gly Ser Leu Ser Tyr
        195                 200                 205

Pro Ser Gly Pro Ala Asn Pro Ser Glu Thr Leu Pro Asp Pro Ser Ile
        210                 215                 220

Val Pro Phe Phe Cys Gly Asn Thr Ile Leu Val Asn Gly Lys Ala Trp
225                 230                 235                 240

Pro Tyr Met Glu Val Glu Pro Arg Thr Tyr Arg Phe Arg Ile Leu Asn
            245                 250                 255

Ala Ser Asn Thr Arg Thr Phe Ser Leu Ser Leu Asn Asn Gly Gly Lys
            260                 265                 270

Phe Ile Gln Ile Gly Ser Asp Gly Gly Leu Leu Pro Arg Ser Val Lys
        275                 280                 285

Thr Gln Ser Ile Ser Leu Ala Pro Ala Glu Arg Tyr Asp Val Leu Ile
290                 295                 300

Asp Phe Ser Ala Phe Asp Gly Glu His Ile Ile Leu Thr Asn Gly Thr
305                 310                 315                 320

Gly Cys Gly Gly Asp Ala Pro Asp Thr Asp Ala Asn Val Met Gln
            325                 330                 335

Phe Arg Val Thr Asn Pro Leu Lys Gly Ala Asp Thr Ser Arg Lys Pro
            340                 345                 350

Lys Tyr Leu Ser Thr Met Pro Asn Val Thr Ser Lys Arg Ile His Asn
            355                 360                 365

Ile Arg Thr Leu Lys Leu Thr Asn Thr Gln Asp Lys Tyr Gly Arg Pro
        370                 375                 380

Val Leu Thr Leu Asn Asn Lys Arg Trp His Asp Pro Val Thr Glu Ala
385                 390                 395                 400

Pro Lys Leu Gly Thr Thr Glu Ile Trp Ser Ile Ile Asn Pro Met Gly
            405                 410                 415

Gly Thr His Pro Ile His Leu His Leu Val Ser Phe Gln Ile Leu Asp
            420                 425                 430

Arg Arg Pro Phe Asp Leu Glu Arg Tyr Asn Lys Phe Gly Asp Ile Val
            435                 440                 445

Tyr Thr Gly Pro Ala Val Pro Pro Pro Ser Glu Lys Gly Trp Lys
            450                 455                 460

Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
                485                 490                 495

His Glu Asp Tyr Asp Met Met Arg Pro Met Asp Val Thr Asp Lys Gln
            500                 505                 510

<210> SEQ ID NO 90
<211> LENGTH: 512
<212> TYPE: PRT
<213> ORGANISM: Bacillus spec

<400> SEQUENCE: 90

Met Ala Leu Glu Lys Phe Ala Asp Glu Leu Pro Ile Ile Glu Thr Leu
1               5                   10                  15
```

```
Gln Pro Gln Lys Lys Ser Asp Gly Ser Thr Tyr Tyr Glu Val Thr Met
                20                  25                  30

Lys Glu Cys Phe His Lys Leu His Arg Asp Leu Pro Pro Thr Arg Leu
             35                  40                  45

Trp Gly Tyr Asn Gly Leu Phe Pro Gly Pro Thr Ile Asp Val Asn Gln
 50                  55                  60

Asp Glu Asn Val Tyr Ile Lys Trp Met Asn Asp Leu Pro Asp Lys His
 65                  70                  75                  80

Phe Leu Pro Val Asp His Thr Ile His His Ser Glu Ser Gly His Gln
                 85                  90                  95

Glu Pro Asp Val Lys Thr Val Val His Leu His Gly Gly Ala Thr Pro
                100                 105                 110

Pro Asp Ser Asp Gly Tyr Pro Glu Ala Trp Phe Thr Lys Asp Phe Lys
            115                 120                 125

Glu Thr Gly Pro Tyr Phe Glu Lys Glu Val Tyr His Tyr Pro Asn Lys
        130                 135                 140

Gln Arg Gly Ala Leu Leu Trp Tyr His Asp His Thr Met Ala Ile Thr
145                 150                 155                 160

Arg Leu Asn Val Phe Ala Gly Leu Ala Gly Met Tyr Ile Ile Arg Glu
                165                 170                 175

Arg Lys Glu Lys Gln Leu Lys Leu Pro Ser Gly Glu Tyr Asp Val Pro
            180                 185                 190

Leu Met Ile Leu Asp Arg Thr Leu Asn Asp Asp Gly Ser Leu Ser Tyr
        195                 200                 205

Pro Ser Gly Pro Ala Asn Pro Ser Glu Thr Leu Pro Asp Pro Ser Ile
    210                 215                 220

Val Pro Phe Phe Cys Gly Asn Thr Ile Leu Val Asn Gly Lys Ala Trp
225                 230                 235                 240

Pro Tyr Met Glu Val Glu Pro Arg Thr Tyr Arg Phe Arg Ile Leu Asn
                245                 250                 255

Ala Ser Asn Thr Arg Thr Phe Ser Leu Ser Leu Asn Asn Gly Gly Lys
            260                 265                 270

Phe Ile Gln Ile Gly Ser Asp Gly Gly Leu Leu Pro Arg Ser Val Lys
        275                 280                 285

Thr Gln Ser Ile Ser Leu Ala Pro Ala Glu Arg Tyr Asp Val Leu Ile
    290                 295                 300

Asp Phe Ser Ala Phe Asp Gly Glu His Ile Ile Leu Thr Asn Gly Thr
305                 310                 315                 320

Gly Cys Gly Gly Asp Ala Asp Pro Asp Thr Asp Ala Asn Val Met Gln
                325                 330                 335

Phe Arg Val Thr Lys Pro Leu Lys Gly Glu Asp Thr Ser Arg Lys Pro
            340                 345                 350

Lys Tyr Leu Ser Thr Met Pro Asn Val Thr Ser Lys Arg Ile His Asn
        355                 360                 365

Ile Arg Thr Leu Lys Leu Thr Asn Thr Gln Asp Lys Tyr Gly Arg Pro
    370                 375                 380

Val Leu Thr Leu Asn Asn Lys Arg Trp His Asp Pro Val Thr Glu Ala
385                 390                 395                 400

Pro Lys Leu Gly Thr Thr Glu Ile Trp Ser Ile Ile Asn Pro Met Gly
                405                 410                 415

Gly Thr His Pro Ile His Leu His Leu Val Ser Phe Gln Ile Leu Asp
            420                 425                 430
```

```
Arg Arg Pro Phe Asp Leu Glu Arg Tyr Asn Lys Phe Gly Asp Ile Val
            435                 440                 445

Tyr Thr Gly Pro Ala Val Pro Pro Pro Ser Glu Lys Gly Trp Lys
450                     455                 460

Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
                485                 490                 495

His Glu Asp Tyr Asp Met Met Arg Pro Met Asp Val Thr Asp Lys Gln
            500                 505                 510
```

<210> SEQ ID NO 91
<211> LENGTH: 512
<212> TYPE: PRT
<213> ORGANISM: Bacillus spec

<400> SEQUENCE: 91

```
Met Ala Leu Glu Lys Phe Ala Asp Glu Leu Pro Ile Ile Glu Thr Leu
1               5                   10                  15

Gln Pro Gln Lys Lys Ser Asp Gly Ser Thr Tyr Tyr Glu Val Thr Met
            20                  25                  30

Lys Glu Cys Phe His Lys Leu His Arg Asp Leu Pro Pro Thr Arg Leu
        35                  40                  45

Trp Gly Tyr Asn Gly Leu Phe Pro Gly Pro Thr Ile Asp Val Asn Lys
    50                  55                  60

Asp Glu Asn Val Tyr Ile Lys Trp Met Asn Asp Leu Pro Asp Lys His
65                  70                  75                  80

Phe Leu Pro Val Asp His Thr Ile His His Ser Glu Ser Gly His Gln
                85                  90                  95

Glu Pro Asp Val Lys Thr Val Val His Leu His Gly Gly Ala Thr Pro
            100                 105                 110

Pro Asp Ser Asp Gly Tyr Pro Glu Ala Trp Phe Thr Lys Asp Phe Lys
        115                 120                 125

Glu Thr Gly Pro Tyr Phe Glu Lys Glu Val Tyr His Tyr Pro Asn Lys
    130                 135                 140

Gln Arg Gly Ala Leu Leu Trp Tyr His Asp His Ala Met Ala Ile Thr
145                 150                 155                 160

Arg Leu Asn Val Tyr Ala Gly Leu Ala Gly Met Tyr Ile Ile Arg Glu
                165                 170                 175

Arg Lys Glu Lys Gln Leu Lys Leu Pro Ser Gly Glu Tyr Asp Val Pro
            180                 185                 190

Leu Met Ile Leu Asp Arg Thr Leu Asn Asp Asp Gly Ser Leu Ser Tyr
        195                 200                 205

Pro Ser Gly Pro Ala Asn Pro Ser Glu Thr Leu Pro Asp Pro Ser Ile
    210                 215                 220

Val Pro Phe Phe Cys Gly Asn Thr Ile Leu Val Asn Gly Lys Ala Trp
225                 230                 235                 240

Pro Tyr Met Glu Val Glu Pro Arg Thr Tyr Arg Phe Arg Ile Leu Asn
                245                 250                 255

Ala Ser Asn Thr Arg Thr Phe Ser Leu Ser Leu Asn Asn Gly Gly Lys
            260                 265                 270

Phe Ile Gln Ile Gly Ser Asp Gly Gly Leu Leu Pro Arg Ser Val Lys
        275                 280                 285

Thr Gln Ser Ile Ser Leu Ala Pro Ala Glu Arg Tyr Asp Val Leu Ile
    290                 295                 300
```

```
Asp Phe Ser Ala Phe Asp Gly Glu His Ile Ile Leu Thr Asn Gly Thr
305                 310                 315                 320

Gly Cys Gly Gly Asp Val Pro Asp Thr Asp Ala Asn Val Met Gln
            325                 330                 335

Phe Arg Val Thr Lys Pro Leu Lys Gly Glu Asp Thr Ser Arg Lys Pro
                340                 345                 350

Lys Tyr Leu Ser Thr Met Pro Asn Val Thr Ser Lys Arg Ile His Asn
            355                 360                 365

Ile Arg Thr Leu Lys Leu Thr Asn Thr Gln Asp Lys Tyr Gly Arg Pro
        370                 375                 380

Val Leu Thr Leu Asn Asn Lys Arg Trp His Asp Pro Val Thr Glu Ala
385                 390                 395                 400

Pro Lys Leu Gly Ala Thr Glu Ile Trp Ser Ile Ile Asn Pro Met Gly
                405                 410                 415

Gly Thr His Pro Ile His Leu His Leu Val Ser Phe Gln Ile Leu Asp
            420                 425                 430

Arg Arg Pro Phe Asp Leu Glu Arg Tyr Asn Lys Phe Gly Asp Ile Val
                435                 440                 445

Tyr Thr Gly Pro Ala Val Pro Pro Pro Ser Glu Lys Gly Trp Lys
            450                 455                 460

Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
                485                 490                 495

His Glu Asp Tyr Asp Met Met Arg Pro Met Asp Val Thr Asp Lys Gln
            500                 505                 510

<210> SEQ ID NO 92
<211> LENGTH: 512
<212> TYPE: PRT
<213> ORGANISM: Bacillus spec

<400> SEQUENCE: 92

Met Ala Leu Glu Lys Phe Ala Asp Glu Leu Pro Ile Ile Glu Thr Leu
1               5                   10                  15

Gln Pro Gln Lys Lys Ser Asp Gly Ser Thr Tyr Tyr Glu Val Thr Met
                20                  25                  30

Lys Glu Cys Phe His Lys Leu His Arg Asp Leu Pro Pro Thr Arg Leu
            35                  40                  45

Trp Gly Tyr Asn Gly Leu Phe Pro Gly Pro Thr Ile Asp Val Asn Gln
        50                  55                  60

Asp Glu Asn Val Tyr Ile Lys Trp Met Asn Asp Leu Pro Asp Lys His
65                  70                  75                  80

Phe Leu Pro Val Asp His Thr Ile His His Ser Glu Ser Gly His Gln
                85                  90                  95

Glu Pro Asp Val Lys Thr Val Val His Leu His Gly Gly Ala Thr Pro
            100                 105                 110

Pro Asp Ser Asp Gly Tyr Pro Glu Ala Trp Phe Thr Lys Asp Phe Lys
        115                 120                 125

Glu Thr Gly Pro Tyr Phe Glu Arg Glu Val Tyr Tyr Pro Asn Lys
    130                 135                 140

Gln Arg Gly Ala Leu Leu Trp Tyr His Asp His Ala Met Ala Ile Thr
145                 150                 155                 160

Arg Leu Asn Val Tyr Ala Gly Leu Ala Gly Met Tyr Ile Ile Arg Glu
```

```
                    165                 170                 175
Arg Lys Glu Lys Gln Leu Lys Leu Pro Ser Gly Glu Tyr Asp Val Pro
                180                 185                 190

Leu Met Ile Leu Asp Arg Thr Leu Asn Asp Asp Gly Ser Leu Ser Tyr
            195                 200                 205

Pro Ser Gly Pro Ala Thr Pro Ser Glu Thr Leu Pro Asp Pro Ser Ile
        210                 215                 220

Val Pro Phe Phe Cys Gly Asn Thr Ile Leu Val Asn Gly Lys Ala Trp
225                 230                 235                 240

Pro Tyr Met Glu Val Glu Pro Arg Thr Tyr Arg Phe Arg Ile Leu Asn
                245                 250                 255

Ala Ser Asn Thr Arg Thr Phe Ser Leu Ser Leu Asn Asn Gly Gly Lys
            260                 265                 270

Phe Ile Gln Ile Gly Ser Asp Gly Gly Leu Leu Pro Arg Ser Val Lys
        275                 280                 285

Thr Gln Ser Ile Ser Leu Ala Pro Ala Glu Arg Tyr Asp Val Leu Ile
        290                 295                 300

Asp Phe Ser Ala Phe Asp Gly Glu His Ile Ile Leu Thr Asn Gly Thr
305                 310                 315                 320

Gly Cys Gly Gly Asp Ala Asp Pro Asp Thr Asp Ala Asn Val Met Gln
                325                 330                 335

Phe Arg Val Thr Lys Ala Leu Lys Gly Ala Asp Thr Ser Arg Lys Pro
            340                 345                 350

Lys Tyr Leu Ser Thr Met Pro Asn Val Thr Ser Lys Arg Ile His Asn
        355                 360                 365

Ile Arg Thr Leu Lys Leu Thr Asn Thr Gln Asp Lys Tyr Gly Arg Pro
    370                 375                 380

Val Leu Thr Leu Asn Asn Lys Arg Trp His Asp Pro Val Thr Glu Ala
385                 390                 395                 400

Pro Lys Leu Gly Thr Thr Glu Ile Trp Ser Ile Ile Asn Pro Met Gly
                405                 410                 415

Gly Thr His Pro Ile His Leu His Leu Val Ser Phe Gln Ile Leu Asp
            420                 425                 430

Arg Arg Pro Phe Asp Leu Glu Arg Tyr Asn Lys Phe Gly Asp Ile Val
        435                 440                 445

Tyr Thr Gly Pro Ala Val Pro Pro Pro Ser Glu Lys Gly Trp Lys
        450                 455                 460

Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
                485                 490                 495

His Glu Asp Tyr Asp Met Met Arg Pro Met Asp Val Thr Asp Lys Gln
            500                 505                 510

<210> SEQ ID NO 93
<211> LENGTH: 512
<212> TYPE: PRT
<213> ORGANISM: Bacillus spec

<400> SEQUENCE: 93

Met Ala Leu Glu Lys Phe Ala Asp Glu Leu Pro Ile Ile Glu Thr Leu
1               5                   10                  15

Lys Pro Gln Lys Thr Ser Asn Gly Ser Thr Tyr Tyr Glu Val Thr Met
            20                  25                  30
```

-continued

Lys Glu Cys Phe His Lys Leu His Arg Asp Leu Pro Pro Thr Arg Leu
             35                  40                  45

Trp Gly Tyr Asn Gly Leu Phe Pro Gly Pro Thr Ile Asp Val Asn Gln
 50                  55                  60

Asp Glu Asn Val Tyr Ile Lys Trp Met Asn Asp Leu Pro Asp Lys His
 65                  70                  75                  80

Phe Leu Pro Val Asp His Thr Ile His Ser Glu Gly Gly His Gln
                 85                  90                  95

Glu Pro Asp Val Lys Thr Val Val His Leu His Gly Gly Ala Thr Pro
                100                 105                 110

Pro Asp Ser Asp Gly Tyr Pro Glu Ala Trp Phe Thr Arg Asp Phe Lys
            115                 120                 125

Glu Lys Gly Pro Tyr Phe Glu Lys Glu Val Tyr His Tyr Pro Asn Lys
        130                 135                 140

Gln Arg Gly Ala Leu Leu Trp Tyr His Asp His Ala Met Ala Ile Thr
145                 150                 155                 160

Arg Leu Asn Val Tyr Ala Gly Leu Ala Gly Met Tyr Ile Ile Arg Glu
                165                 170                 175

Arg Lys Glu Lys Gln Leu Lys Leu Pro Ala Gly Glu Tyr Asp Val Pro
            180                 185                 190

Leu Met Ile Met Asp Arg Thr Leu Asn Asp Asp Gly Ser Leu Phe Tyr
        195                 200                 205

Pro Ser Gly Pro Asp Asn Pro Ser Glu Thr Leu Pro Asn Pro Ser Ile
    210                 215                 220

Val Pro Phe Leu Cys Gly Asn Thr Ile Leu Val Asn Gly Lys Ala Trp
225                 230                 235                 240

Pro Tyr Met Glu Val Glu Pro Arg Thr Tyr Arg Phe Arg Ile Leu Asn
                245                 250                 255

Ala Ser Asn Thr Arg Thr Phe Ser Leu Ser Leu Asn Asn Gly Gly Arg
            260                 265                 270

Phe Ile Gln Ile Gly Ser Asp Gly Gly Leu Leu Pro Arg Ser Val Lys
        275                 280                 285

Thr Gln Ser Ile Ser Leu Ala Pro Ala Glu Arg Tyr Asp Val Leu Ile
    290                 295                 300

Asp Phe Ser Ala Phe Asp Gly Glu His Ile Ile Leu Thr Asn Gly Thr
305                 310                 315                 320

Gly Cys Gly Gly Asp Val Asn Pro Asp Thr Asp Ala Asn Val Met Gln
                325                 330                 335

Phe Arg Val Thr Lys Pro Leu Lys Gly Glu Asp Thr Ser Arg Lys Pro
            340                 345                 350

Lys Tyr Leu Ser Ala Met Pro Asp Met Thr Ser Lys Arg Ile His Asn
        355                 360                 365

Ile Arg Thr Leu Lys Leu Thr Asn Thr Gln Asp Lys Tyr Gly Arg Pro
    370                 375                 380

Val Leu Thr Leu Asn Asn Lys Arg Trp His Asp Pro Val Thr Glu Ala
385                 390                 395                 400

Pro Arg Leu Gly Ser Thr Glu Ile Trp Ser Ile Ile Asn Pro Thr Arg
                405                 410                 415

Gly Thr His Pro Ile His Leu His Leu Val Ser Phe Gln Val Leu Asp
            420                 425                 430

Arg Arg Pro Phe Asp Leu Glu Arg Tyr Asn Lys Phe Gly Asp Ile Val
        435                 440                 445

Tyr Thr Gly Pro Ala Val Pro Pro Pro Ser Glu Lys Gly Trp Lys

```
              450                 455                 460
Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
                485                 490                 495

His Glu Asp Tyr Asp Met Met Arg Pro Met Asp Val Thr Glu Lys Gln
                500                 505                 510

<210> SEQ ID NO 94
<211> LENGTH: 512
<212> TYPE: PRT
<213> ORGANISM: Bacillus spec

<400> SEQUENCE: 94

Met Ala Leu Glu Lys Phe Ala Asp Glu Leu Pro Ile Ile Glu Thr Leu
1               5                   10                  15

Lys Pro Gln Lys Lys Ser Asp Gly Ser Thr Tyr Tyr Glu Val Thr Met
                20                  25                  30

Lys Glu Cys Phe His Lys Leu His Arg Asp Leu Pro Pro Thr Arg Leu
            35                  40                  45

Trp Gly Tyr Asn Gly Leu Phe Pro Gly Pro Thr Ile Asp Val Asn Gln
    50                  55                  60

Gly Glu Ser Ile Tyr Val Lys Trp Met Asn Asp Leu Pro Asp Lys His
65                  70                  75                  80

Phe Leu Pro Val Asp His Thr Ile His His Ser Glu Ser Gly His Gln
                85                  90                  95

Glu Pro Asp Val Arg Thr Val Val His Leu His Gly Gly Glu Thr Pro
            100                 105                 110

Pro Asp Ser Asp Gly Tyr Pro Glu Ala Trp Phe Thr Arg Asp Phe Lys
        115                 120                 125

Glu Thr Gly Pro Tyr Phe Glu Lys Glu Val Tyr His Tyr Pro Asn Lys
130                 135                 140

Gln Arg Gly Ala Leu Leu Trp Tyr His Asp His Ala Met Ala Ala Thr
145                 150                 155                 160

Arg Leu Asn Val Tyr Ala Gly Leu Ala Gly Met Tyr Ile Ile Arg Glu
                165                 170                 175

Arg Lys Glu Lys Gln Leu Lys Leu Pro Ala Gly Glu Tyr Asp Val Pro
            180                 185                 190

Leu Met Ile Leu Asp Arg Thr Leu Asn Asp Asp Gly Ser Leu Ser Tyr
        195                 200                 205

Pro Ser Gly Pro Asp Asn Pro Ser Glu Thr Leu Pro Thr Pro Ser Ile
210                 215                 220

Val Pro Phe Leu Cys Gly Asn Thr Ile Leu Val Asn Gly Lys Ala Trp
225                 230                 235                 240

Pro Tyr Met Glu Val Glu Pro Arg Thr Tyr Arg Phe Arg Ile Leu Asn
                245                 250                 255

Ala Ser Asn Met Arg Ser Phe Thr Leu Ser Leu Asn Asn Gly Gly Arg
            260                 265                 270

Phe Ile Gln Ile Gly Ser Asp Gly Gly Leu Leu Pro Arg Ser Val Arg
        275                 280                 285

Thr Gln Thr Ile Ser Leu Ala Pro Ala Glu Arg Tyr Asp Val Leu Ile
        290                 295                 300

Asp Phe Ser Ala Phe Asp Gly Glu His Ile Ile Leu Thr Asn Gly Thr
305                 310                 315                 320
```

Gly Cys Gly Gly Asp Val Asp Pro Asp Thr Asp Ala Asn Val Met Gln
            325                 330                 335

Phe Arg Val Thr Lys Pro Leu Lys Gly Glu Asp Thr Ser Arg Lys Pro
        340                 345                 350

Lys Tyr Leu Ser Ala Met Pro Asp Met Thr Ser Lys Arg Ile His Asn
    355                 360                 365

Ile Arg Thr Leu Lys Leu Thr Asn Thr Gln Asp Lys Tyr Gly Arg Pro
370                 375                 380

Val Leu Thr Leu Asn Asn Lys Arg Trp His Asp Pro Val Thr Glu Ala
385                 390                 395                 400

Pro Lys Leu Gly Thr Thr Glu Ile Trp Ser Ile Ile Asn Pro Met Gly
            405                 410                 415

Gly Thr His Pro Ile His Leu His Leu Val Ser Phe Gln Val Leu Asp
            420                 425                 430

Arg Arg Pro Phe Asp Leu Glu Arg Tyr Asn Lys Phe Gly Asp Ile Val
        435                 440                 445

Tyr Thr Gly Pro Ala Val Pro Pro Pro Ser Glu Lys Gly Trp Lys
    450                 455                 460

Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
            485                 490                 495

His Glu Asp Tyr Asp Met Met Arg Pro Met Asp Val Thr Asp Lys Gln
            500                 505                 510

<210> SEQ ID NO 95
<211> LENGTH: 28
<212> TYPE: PRT
<213> ORGANISM: Bacillus spec

<400> SEQUENCE: 95

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 96
<211> LENGTH: 28
<212> TYPE: PRT
<213> ORGANISM: Bacillus spec

<400> SEQUENCE: 96

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 97
<211> LENGTH: 28
<212> TYPE: PRT
<213> ORGANISM: Bacillus spec

<400> SEQUENCE: 97

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 98
<211> LENGTH: 28
<212> TYPE: PRT
<213> ORGANISM: Bacillus spec

<400> SEQUENCE: 98

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 99
<211> LENGTH: 28
<212> TYPE: PRT
<213> ORGANISM: Bacillus spec

<400> SEQUENCE: 99

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 100
<211> LENGTH: 28
<212> TYPE: PRT
<213> ORGANISM: Bacillus spec

<400> SEQUENCE: 100

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 101
<211> LENGTH: 28
<212> TYPE: PRT
<213> ORGANISM: Bacillus spec

<400> SEQUENCE: 101

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 102
<211> LENGTH: 28
<212> TYPE: PRT
<213> ORGANISM: Bacillus spec

<400> SEQUENCE: 102

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 103
<211> LENGTH: 28
<212> TYPE: PRT
<213> ORGANISM: Bacillus spec

<400> SEQUENCE: 103

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 104
<211> LENGTH: 28
<212> TYPE: PRT
<213> ORGANISM: Bacillus spec

<400> SEQUENCE: 104

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 105
<211> LENGTH: 28
<212> TYPE: PRT
<213> ORGANISM: Bacillus spec

<400> SEQUENCE: 105

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 106
<211> LENGTH: 28
<212> TYPE: PRT
<213> ORGANISM: Bacillus spec

<400> SEQUENCE: 106

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 107
<211> LENGTH: 28
<212> TYPE: PRT
<213> ORGANISM: Bacillus spec

<400> SEQUENCE: 107

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 108
<211> LENGTH: 28
<212> TYPE: PRT
<213> ORGANISM: Bacillus spec

<400> SEQUENCE: 108

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 109
<211> LENGTH: 28
<212> TYPE: PRT
<213> ORGANISM: Bacillus spec

<400> SEQUENCE: 109

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 110
<211> LENGTH: 28
<212> TYPE: PRT
<213> ORGANISM: Bacillus spec

<400> SEQUENCE: 110

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 111
<211> LENGTH: 28
<212> TYPE: PRT
<213> ORGANISM: Bacillus spec

<400> SEQUENCE: 111

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 112
<211> LENGTH: 28
<212> TYPE: PRT
<213> ORGANISM: Bacillus spec

<400> SEQUENCE: 112

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 113
<211> LENGTH: 28
<212> TYPE: PRT
<213> ORGANISM: Bacillus spec

<400> SEQUENCE: 113

Lys Asp Leu Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 114
<211> LENGTH: 28
<212> TYPE: PRT
<213> ORGANISM: Bacillus spec

<400> SEQUENCE: 114

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 115
<211> LENGTH: 28
<212> TYPE: PRT
<213> ORGANISM: Bacillus spec

<400> SEQUENCE: 115

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 116
<211> LENGTH: 28
<212> TYPE: PRT
<213> ORGANISM: Bacillus spec

<400> SEQUENCE: 116

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 117
<211> LENGTH: 28
<212> TYPE: PRT
<213> ORGANISM: Bacillus spec

<400> SEQUENCE: 117

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 118
<211> LENGTH: 28
<212> TYPE: PRT
<213> ORGANISM: Bacillus spec

<400> SEQUENCE: 118

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 119
<211> LENGTH: 28
<212> TYPE: PRT
<213> ORGANISM: Bacillus spec

<400> SEQUENCE: 119

Lys Asp Phe Glu Gln Thr Gly Pro Tyr Phe Lys Arg Glu Val Tyr His
1               5                   10                  15

Tyr Pro Asn Gln Gln Arg Gly Ala Ile Leu Trp Tyr
            20                  25

<210> SEQ ID NO 120
<211> LENGTH: 28
<212> TYPE: PRT
<213> ORGANISM: Bacillus spec

<400> SEQUENCE: 120

Lys Asp Phe Glu Gln Thr Gly Pro Tyr Phe Lys Arg Glu Ile Tyr His

```
                1               5                  10                  15
Tyr Pro Asn Gln Gln Arg Gly Ala Ile Leu Trp Tyr
            20                  25

<210> SEQ ID NO 121
<211> LENGTH: 28
<212> TYPE: PRT
<213> ORGANISM: Bacillus spec

<400> SEQUENCE: 121

Lys Asp Phe Glu Gln Thr Gly Pro Tyr Phe Lys Arg Glu Val Tyr His
1               5                  10                  15

Tyr Pro Asn Gln Gln Arg Gly Ala Ile Leu Trp Tyr
            20                  25

<210> SEQ ID NO 122
<211> LENGTH: 28
<212> TYPE: PRT
<213> ORGANISM: Bacillus spec

<400> SEQUENCE: 122

Lys Asp Phe Glu Gln Thr Gly Pro Tyr Phe Lys Arg Glu Val Tyr His
1               5                  10                  15

Tyr Pro Asn Gln Gln Arg Gly Ala Ile Leu Trp Tyr
            20                  25

<210> SEQ ID NO 123
<211> LENGTH: 28
<212> TYPE: PRT
<213> ORGANISM: Bacillus spec

<400> SEQUENCE: 123

Lys Asp Phe Glu Gln Thr Gly Pro Tyr Phe Lys Arg Glu Val Tyr His
1               5                  10                  15

Tyr Pro Asn Gln Gln Arg Gly Ala Ile Leu Trp Tyr
            20                  25

<210> SEQ ID NO 124
<211> LENGTH: 28
<212> TYPE: PRT
<213> ORGANISM: Bacillus spec

<400> SEQUENCE: 124

Lys Asp Phe Glu Gln Thr Gly Pro Tyr Phe Lys Arg Glu Val Tyr His
1               5                  10                  15

Tyr Pro Asn Gln Gln Arg Gly Ala Ile Leu Trp Tyr
            20                  25

<210> SEQ ID NO 125
<211> LENGTH: 28
<212> TYPE: PRT
<213> ORGANISM: Bacillus spec

<400> SEQUENCE: 125

Lys Gly Phe Gln Glu Thr Gly Pro Tyr Phe Ser Arg Glu Ile Tyr His
1               5                  10                  15

Tyr Pro Asn Gln Gln Arg Gly Ala Ile Leu Trp Tyr
            20                  25

<210> SEQ ID NO 126
<211> LENGTH: 28
<212> TYPE: PRT
```

<213> ORGANISM: Bacillus spec

<400> SEQUENCE: 126

Lys Gly Phe Gln Glu Thr Gly Pro Tyr Phe Ser Arg Glu Ile Tyr His
1               5                   10                  15
Tyr Pro Asn Gln Gln Arg Gly Ala Ile Leu Trp Tyr
            20                  25

<210> SEQ ID NO 127
<211> LENGTH: 28
<212> TYPE: PRT
<213> ORGANISM: Bacillus spec

<400> SEQUENCE: 127

Lys Asp Phe Lys Glu Thr Gly Pro Tyr Phe Glu Lys Glu Val Tyr His
1               5                   10                  15
Tyr Pro Asn Lys Gln Arg Gly Ala Leu Leu Trp Tyr
            20                  25

<210> SEQ ID NO 128
<211> LENGTH: 28
<212> TYPE: PRT
<213> ORGANISM: Bacillus spec

<400> SEQUENCE: 128

Lys Asp Phe Lys Glu Thr Gly Pro Tyr Phe Glu Arg Glu Val Tyr His
1               5                   10                  15
Tyr Pro Asn Lys Gln Arg Gly Ala Leu Leu Trp Tyr
            20                  25

<210> SEQ ID NO 129
<211> LENGTH: 28
<212> TYPE: PRT
<213> ORGANISM: Bacillus spec

<400> SEQUENCE: 129

Lys Asp Phe Lys Glu Thr Gly Pro Tyr Phe Glu Lys Glu Val Tyr His
1               5                   10                  15
Tyr Pro Asn Lys Gln Arg Gly Ala Leu Leu Trp Tyr
            20                  25

<210> SEQ ID NO 130
<211> LENGTH: 28
<212> TYPE: PRT
<213> ORGANISM: Bacillus spec

<400> SEQUENCE: 130

Lys Asp Phe Lys Glu Thr Gly Pro Tyr Phe Glu Lys Glu Val Tyr His
1               5                   10                  15
Tyr Pro Asn Lys Gln Arg Gly Ala Leu Leu Trp Tyr
            20                  25

<210> SEQ ID NO 131
<211> LENGTH: 28
<212> TYPE: PRT
<213> ORGANISM: Bacillus spec

<400> SEQUENCE: 131

Lys Asp Phe Lys Glu Thr Gly Pro Tyr Phe Glu Arg Glu Val Tyr His
1               5                   10                  15
Tyr Pro Asn Lys Gln Arg Gly Ala Leu Leu Trp Tyr
            20                  25

<210> SEQ ID NO 132
<211> LENGTH: 28
<212> TYPE: PRT
<213> ORGANISM: Bacillus spec

<400> SEQUENCE: 132

Lys Asp Phe Lys Glu Thr Gly Pro Tyr Phe Glu Arg Glu Val Tyr His
1               5                   10                  15

Tyr Pro Asn Lys Gln Arg Gly Ala Leu Leu Trp Tyr
            20                  25

<210> SEQ ID NO 133
<211> LENGTH: 28
<212> TYPE: PRT
<213> ORGANISM: Bacillus spec

<400> SEQUENCE: 133

Lys Asp Phe Lys Glu Thr Gly Pro Tyr Phe Glu Lys Glu Val Tyr His
1               5                   10                  15

Tyr Pro Asn Lys Gln Arg Gly Ala Leu Leu Trp Tyr
            20                  25

<210> SEQ ID NO 134
<211> LENGTH: 28
<212> TYPE: PRT
<213> ORGANISM: Bacillus spec

<400> SEQUENCE: 134

Lys Asp Phe Lys Glu Thr Gly Pro Tyr Phe Glu Arg Glu Val Tyr His
1               5                   10                  15

Tyr Pro Asn Lys Gln Arg Gly Ala Leu Leu Trp Tyr
            20                  25

<210> SEQ ID NO 135
<211> LENGTH: 28
<212> TYPE: PRT
<213> ORGANISM: Bacillus spec

<400> SEQUENCE: 135

Lys Asp Phe Lys Glu Thr Gly Pro Tyr Phe Glu Lys Glu Val Tyr His
1               5                   10                  15

Tyr Pro Asn Lys Gln Arg Gly Ala Leu Leu Trp Tyr
            20                  25

<210> SEQ ID NO 136
<211> LENGTH: 28
<212> TYPE: PRT
<213> ORGANISM: Bacillus spec

<400> SEQUENCE: 136

Lys Asp Phe Lys Glu Thr Gly Pro Tyr Phe Glu Lys Glu Val Tyr His
1               5                   10                  15

Tyr Pro Asn Lys Gln Arg Gly Ala Leu Leu Trp Tyr
            20                  25

<210> SEQ ID NO 137
<211> LENGTH: 28
<212> TYPE: PRT
<213> ORGANISM: Bacillus spec

<400> SEQUENCE: 137

-continued

```
Lys Asp Phe Lys Glu Thr Gly Pro Tyr Phe Arg Glu Val Tyr His
1               5                   10                  15

Tyr Pro Asn Lys Gln Arg Gly Ala Leu Leu Trp Tyr
                20                  25

<210> SEQ ID NO 138
<211> LENGTH: 28
<212> TYPE: PRT
<213> ORGANISM: Bacillus spec

<400> SEQUENCE: 138

Arg Asp Phe Lys Glu Lys Gly Pro Tyr Phe Glu Lys Glu Val Tyr His
1               5                   10                  15

Tyr Pro Asn Lys Gln Arg Gly Ala Leu Leu Trp Tyr
                20                  25

<210> SEQ ID NO 139
<211> LENGTH: 28
<212> TYPE: PRT
<213> ORGANISM: Bacillus spec

<400> SEQUENCE: 139

Arg Asp Phe Lys Glu Thr Gly Pro Tyr Phe Glu Lys Glu Val Tyr His
1               5                   10                  15

Tyr Pro Asn Lys Gln Arg Gly Ala Leu Leu Trp Tyr
                20                  25
```